US010005824B2

(12) United States Patent
Oestergaard et al.

(10) Patent No.: US 10,005,824 B2
(45) Date of Patent: Jun. 26, 2018

(54) SELECTIVE PYY COMPOUNDS AND USES THEREOF

(71) Applicant: Novo Nordisk A/S, Bagsvaerd (DK)

(72) Inventors: Soeren Oestergaard, Broenshoej (DK); Carsten Jessen, Birkeroed (DK); Birgitte Schjellerup Wulff, Virum (DK); Annika Sanfridson, Bjaerred (SE)

(73) Assignee: Novo Nordisk A/S, Bagsvaerd (DK)

( * ) Notice: Subject to any disclaimer, the term of this patent is extended or adjusted under 35 U.S.C. 154(b) by 0 days. days.

(21) Appl. No.: 15/635,456

(22) Filed: Jun. 28, 2017

(65) Prior Publication Data

US 2017/0313750 A1 Nov. 2, 2017

Related U.S. Application Data

(63) Continuation of application No. PCT/EP2016/063429, filed on Jun. 13, 2016.

(30) Foreign Application Priority Data

Jun. 12, 2015 (EP) ..................... 15171785

(51) Int. Cl.
*A61K 38/00* (2006.01)
*A61P 3/04* (2006.01)
*C07K 14/47* (2006.01)

(52) U.S. Cl.
CPC .............. *C07K 14/47* (2013.01); *A61K 38/00* (2013.01)

(58) Field of Classification Search
CPC ................................ A61K 38/00; C07K 14/47
See application file for complete search history.

(56) References Cited

U.S. PATENT DOCUMENTS

| | | | |
|---|---|---|---|
| 5,574,010 A | 11/1996 | McFadden | |
| 5,604,203 A | 2/1997 | Balasubramaniam | |
| 6,046,167 A | 4/2000 | Balasubramaniam | |
| 8,901,073 B2 | 12/2014 | Bloom | |
| 9,085,637 B2* | 7/2015 | Oestergaard | C07K 14/575 |
| 2002/0141985 A1 | 10/2002 | Pittner et al. | |
| 2005/0176630 A1 | 8/2005 | Cowley et al. | |
| 2006/0135747 A1 | 6/2006 | Levy et al. | |
| 2006/0211610 A1 | 9/2006 | Dong | |
| 2007/0135351 A1 | 6/2007 | Conde-Knape et al. | |
| 2007/0197445 A1 | 8/2007 | Balasubramaniam | |
| 2007/0203058 A1 | 8/2007 | Lau et al. | |
| 2008/0194486 A1 | 8/2008 | Bridon et al. | |
| 2008/0221038 A1 | 9/2008 | Balasubramaniam | |
| 2008/0269114 A1 | 10/2008 | Schwartz | |
| 2009/0099074 A1 | 4/2009 | Bridon et al. | |
| 2009/0111730 A1 | 4/2009 | Dorwald et al. | |
| 2009/0186811 A1 | 7/2009 | Schwartz | |
| 2009/0215682 A1 | 8/2009 | Moore et al. | |
| 2010/0069307 A1 | 3/2010 | Danho et al. | |
| 2010/0331245 A1 | 12/2010 | Dong | |
| 2011/0275559 A1 | 11/2011 | Ostergaard et al. | |
| 2012/0040893 A1* | 2/2012 | Cowley | A61K 38/22 514/4.9 |
| 2013/0040877 A1* | 2/2013 | Kofoed | C07K 14/575 514/6.9 |
| 2013/0096055 A1 | 4/2013 | Kofoed et al. | |
| 2015/0141336 A1 | 5/2015 | Joergensen et al. | |
| 2016/0289283 A1* | 10/2016 | Oestergaard | C07K 14/575 |

FOREIGN PATENT DOCUMENTS

| | | |
|---|---|---|
| CN | 1867360 A | 11/2006 |
| CN | 101005857 A | 7/2007 |
| EP | 0908515 A2 | 4/1999 |
| RU | 2275207 C2 | 4/2006 |
| WO | 9614854 A1 | 5/1996 |
| WO | 9820885 A1 | 5/1998 |
| WO | 9964394 A1 | 12/1999 |
| WO | 03/002158 A1 | 1/2003 |
| WO | 04066966 A2 | 8/2004 |
| WO | 2005/005667 A2 | 1/2005 |
| WO | 2005/027978 A2 | 3/2005 |
| WO | 2005/028516 A2 | 3/2005 |
| WO | 2005/058958 A2 | 6/2005 |
| WO | 2005/077072 A2 | 8/2005 |
| WO | 2005/077094 A2 | 8/2005 |
| WO | 2005/089786 A2 | 9/2005 |
| WO | 2005/089789 A2 | 9/2005 |
| WO | 2005/089790 A2 | 9/2005 |
| WO | 2005/117984 A2 | 12/2005 |

(Continued)

OTHER PUBLICATIONS

Betts et al., Chapter 14, "Amino Acid Properties and Consequences of Substitutions," Bioinformatics for Geneticists (2003) ed. By Barnes and Gray, John Wiley & Sons, Ltd., 289-316.*
Kojima S et al. A role for pancreatic polypeptide in feeding and body weight regulation, "Peptides", Year 2007, vol. 28, No. 2, pp. 459-463.
Lin Shu et al. Critical Role of Arcuate Y4 Receptors and the Melanocortin System in Pancreatic Polypeptide-Induced Reduction in Food Intake in Mice, "PLOS ONE" Year 2009, vol. 4, No. 12, pp. e8488-e8488.
Ito T et al, Effects of peripheral administration of PYY3-36 on feed intake and; plasma acyl-ghrelin levels in pigs, Journal of Endocrinology, Year 2006, vol. 191, pp. 113-119.
Ortiz A. et al, A Novel Long-Acting Selective Neuropeptide Y2 Receptor Polyethylene Glycol-Conjugated Peptide Agonist Reduces Food Intake and Body Weight and Improves Glucose Metabolism in Rodents , The Journal of Pharmacology and Experimental Therapeutics (2007), vol. 323, No. 2, pp. 692-700.

(Continued)

*Primary Examiner* — Marcela M Cordero Garcia
(74) *Attorney, Agent, or Firm* — Rosemarie R. Wilk-Orescan

(57) ABSTRACT

The invention relates to PYY compounds with the amino acid modifications 7Lys, 30Trp, and 31Leu, and in addition to these, 22Ile and/or 28Tyr, and derivatives thereof. The compounds of the invention are selective Y2 receptor agonists. The invention also relates to pharmaceutical compositions comprising such PYY compounds and pharmaceutically acceptable excipients, as well as the medical use of the PYY compounds.

34 Claims, No Drawings

(56) References Cited

FOREIGN PATENT DOCUMENTS

| WO | 2006/005667 A2 | 1/2006 |
| WO | 06020207 A2 | 2/2006 |
| WO | 06/049681 A2 | 5/2006 |
| WO | 2006/077035 A1 | 7/2006 |
| WO | 2007/009894 A2 | 1/2007 |
| WO | 2007008778 A2 | 1/2007 |
| WO | 2007/038943 A1 | 4/2007 |
| WO | 2007038942 A1 | 4/2007 |
| WO | 2007/068718 A1 | 6/2007 |
| WO | 07065808 A2 | 6/2007 |
| WO | 07109354 A2 | 9/2007 |
| WO | 2008/003947 A1 | 1/2008 |
| WO | 08/053360 A2 | 5/2008 |
| WO | 2008/087186 A2 | 7/2008 |
| WO | 2008/087190 A2 | 7/2008 |
| WO | 2008132435 A1 | 11/2008 |
| WO | 2009007714 A2 | 1/2009 |
| WO | 2009/030771 A1 | 3/2009 |
| WO | 2009033710 A1 | 3/2009 |
| WO | 2009/042922 A2 | 4/2009 |
| WO | 09042922 A2 | 4/2009 |
| WO | 2009/138511 A1 | 11/2009 |
| WO | 10031707 A1 | 3/2010 |
| WO | 2010031521 A2 | 3/2010 |
| WO | 2010052144 A2 | 5/2010 |
| WO | 2010096175 A1 | 8/2010 |
| WO | 11033068 A1 | 3/2011 |
| WO | 2011033068 A1 | 3/2011 |
| WO | 11045232 A2 | 4/2011 |
| WO | 2011058165 A1 | 5/2011 |
| WO | 2011131646 A1 | 10/2011 |
| WO | 2014178018 A1 | 11/2014 |
| WO | 2015071355 A1 | 5/2015 |

OTHER PUBLICATIONS

Roger Reidelberger et al., Effects of Glycine-Extended and Serine13-Phosphorylated Forms of Peptide YY on Food Intake in Rats, Peptides, Year 2011; vol. 32, No. 4, pp. 770-775.
Adrian et al., GUT, 1978, vol. 19, No. 10, pp. 907-909.
Heizmann et al., Peptide Research, "Synthesis of an N-3-guanidinopropylglycine (Narg) Derivative as a Versatile Building Block for Solid-Phase Peptide and Peptoid Synthesis", 1994, vol. 7, No. 6, pp. 328-332.
Batterham, R.L. et al., "Gut Hormone PYY3-36 Physiologically Inhibits Food Intake", Nature, 2002, vol. 418, pp. 650-654.
Bowie et al. (Science, 1990, 247:1306-1310).
Burgess et al. (J. Cell Biol. 111:2129-2138, 1990).
Lazar et al. (Mol. Cel. Biol., 8:1247-1252, 1988).
Bork (Genome Research, 2000, 10:398-400).
T.W. Schwartz., "Pancreatic Polypeptide: A Hormone Under Vagal Control", Gastroenterology. 1983, vol. 85, pp. 1411-1425.
Whitcomb. Am. J. Physiol. "Characterization of saturable binding sites for circulating pancreatic polypeptide in rat brain." 1990 vol. 259 G687-G691.
Jorgensen, J. Ch. Et al. Euro. J. Pharmacol. "Structure-function studies on neuropeptide Y and pancreatic polypeptide—evidence for two PP-fold receptors in vas deferens" 1990 vol. 186: 105-114.
Cooke, D et al. Nature Reviews. "The obesity pipeline: current strategies in the development of anti-obesity drugs" 2006 vol. 5: 919-930.
Kamiji, M.M et al. Current Topics in Medical Chemistry "NPY Y2 and Y4 receptors selective ligands: promising anti-obesity drugs?" 3008 vol. 7: 1734-1742.
Sainsbury, A. et al. Mol Nad Cell Biol "Synergistic Effects of Y2 and Y4 Receptors on Adiposity and Bone Mass Revealed in Double Knockout Mice" vol. 23: 5225-5233.
Sampson, W.R. J. Pep. Sci. "The Synthesis of 'Difficult' Peptides Using 2-Hydroxy-4-Methoxybenzyl or Pseudoproline Amino Acid Building Blocks: a Comparative Study" 1999 vol. 5: 403.
Knudsen et al. J Med Chem. "Potent Derivatives of Glucagon-Like Peptide-1 with Pharmacokinetic Properties Suitable for Once Daily Administration" 2000. vol. 43(9). p. 1664-1669.
Boggiano, M.M. et al, "PYY3-36 as an anti-obesity drug target", Obesity Reviews. 2005 vol. 6: 307-322.
Dodson, Shontelle et al "Muscle Wasting in Cancer Cachexia: Clinical Implications, Diagnosis, and Emerging Treatment Strategies" Annu. Rev. Med. 2011 vol. 62 pp. 265-79.
Muscaritoli, Maurizio et al "Prevention and Treatment of Cancer Cachexia: New Insights into an Old Problem." European Journal of Cancer, 2006 vol. 42 pp. 31-41.
Soeren L. Pedersen et al., Peptide hormone isoforms: N-terminally branched PYY3-36 isoforms give improved lipid and fat-cell metabolism in diet-induced obese mice, Journal of Peptide Science, Year 2010, vol. 16, Issue 11, pp. 664-673.
van den Hoek A. et al., Chronic PYY3-36 treatment promotes fat oxidation and ameliorates insulin resistance in C57BL6 mice, American Journal of Physiology-Endocrinology and Metabolism, Year 2007, vol. 292, No. 1 pp. E238-E245.
Kouki Kitagawa et al: Solution synthesis of human peptide YY(hPYY),Chemical & Pharmaceutical Bulletin,Year Jun. 1, 1990 vol. 38, No. 6, pp. 1731-1734.
Balasubramaniam et al., "Structure-Activity Studies Including a psi(CH2-NH) Scan of Peptide YY (PYY) Active Site, PYY(22-36), for Interaction with Rat Intestinal PYY Receptors: Development of Analogues with Potent in Vivo Activity in the Intestine," J. Med. Chem., 2000, vol. 43, pp. 3420-3427.

\* cited by examiner

SELECTIVE PYY COMPOUNDS AND USES THEREOF

CROSS-REFERENCE TO RELATED APPLICATIONS

This application is a continuation of International Application PCT/EP2016/063429 (WO 2016/198682), filed Jun. 13, 2016, which claims priority to European Patent Application 15171785.7, filed Jun. 12, 2015; the contents of all above-named applications are incorporated herein by reference.

TECHNICAL FIELD

The present invention relates to analogues and/or derivatives of Peptide YY (PYY), and their pharmaceutical use.

SEQUENCE LISTING

The instant application contains a Sequence Listing which has been submitted in ASCII format via EFS-Web and is hereby incorporated by reference in its entirety. Said ASCII copy, created on Jun. 13, 2017, is named 150019US01 SeqList.txt and is 14 kilobytes in size.

BACKGROUND OF THE INVENTION

PYY is released during a meal from L-cells in the distal small intestine and the colon. PYY is known to have peripheral effects in the gastrointestinal (GI) tract and also act centrally as a satiety signal. PYY is naturally secreted as a 36 amino acid peptide (PYY(1-36)) with a C-terminal amide but is cleaved to PYY(3-36) which constitutes approximately 50% of the circulating PYY. The enzyme responsible for the degradation is dipeptidyl peptidase IV (DPPIV). PYY(3-36) is rapidly eliminated by proteases and other clearance mechanisms. The half-life of PYY(3-36) has been reported to be <30 minutes in pigs. Thus, PYY displays suboptimal pharmacokinetic properties, meaning that the peptide has to be administered at least twice daily.

Whereas PYY(1-36) activates Y1, Y2 and Y5 receptors with very little selectivity and the Y4 receptor slightly less, the DPPIV processed PYY(3-36) displays increased selectivity for the Y2 receptor over Y1, Y4 and Y5 receptors, albeit some Y1 and Y5 affinity is retained. Y2 receptor activation is known to decrease appetite and food intake whereas Y1 and Y5 receptor activation leads to an increase in appetite and food intake. Furthermore, Y1 and Y5 receptor activation may lead to an increase in blood pressure.

PYY(3-36) has been suggested for use in the treatment of obesity and associated diseases based on the demonstrated effects of certain of these peptides in animal models and in man, and on the fact that obese people have low basal levels of PYY as well as lower meal responses of this peptide. Furthermore, Y2 agonists have been demonstrated to have anti-secretory and pro-absorptive effects in the gastro-intestinal (GI) tract. The potential use of Y2 agonists in the treatment of a number of gastro-intestinal disorders has been suggested.

Based on demonstrated effects in e.g. Zucker rats and Diet-Induced Obese (DIO) mice Y2 selective PYY(3-36) analogues have a positive effect on glucose metabolism and are thus suggested to be used for the treatment of diabetes.

WO 2009/138511 relates to long-acting Y2 and/or Y4 receptor agonists. WO 2011/033068 relates to PYY analogues stabilised against C-terminal proteolytic breakdown. WO 2011/058165 relates to Y2 receptor agonists with protracted pharmacokinetic properties.

For the treatment of conditions responsive to Y receptor modulation such as obesity and diabetes it would be attractive to use PYY analogues which are specific for the Y receptor subtype Y2 and importantly also display protracted pharmacokinetic properties and as such can be used in a dosing regimen with lower frequency of administration than PYY or PYY(3-36).

SUMMARY

The invention relates to PYY compounds. In one aspect, the PYY compounds of the present invention have i) lysine at the position corresponding to position 7 or 10 of hPYY (1-36) (SEQ ID NO:1); ii) tryptophan at the position corresponding to position 30 of hPYY(1-36) (SEQ ID NO:1); iii) leucine at the position corresponding to position 31 of hPYY(1-36) (SEQ ID NO:1); iv) tyrosine at the position corresponding to position 28 of hPYY(1-36) (SEQ ID NO:1) and/or isoleucine at the position corresponding to position 22 of hPYY(1-36) (SEQ ID NO:1); and v) a modifying group attached to the epsilon amino group of said lysine at the position corresponding to position 7 or 10 of hPYY(1-36) (SEQ ID NO:1), and may comprise up to 10 amino acid modifications as compared to human PYY(3-36) (hPYY(3-36), SEQ ID NO:2).

In another aspect, the PYY compounds of the present invention have i) lysine at the position corresponding to position 7 or 10 of hPYY(1-36) (SEQ ID NO:1); ii) tryptophan at the position corresponding to position 30 of hPYY(1-36) (SEQ ID NO:1); iii) leucine at the position corresponding to position 31 of hPYY(1-36) (SEQ ID NO:1); iv) tyrosine at the position corresponding to position 28 of hPYY(1-36) (SEQ ID NO:1); and v) a modifying group attached to the epsilon amino group of said lysine at the position corresponding to position 7 or 10 of hPYY(1-36) (SEQ ID NO:1), and may comprise up to 10 amino acid modifications as compared to human PYY(3-36) (hPYY(3-36), SEQ ID NO:2).

In another aspect, the PYY compounds of the present invention have i) lysine at the position corresponding to position 7 or 10 of hPYY(1-36) (SEQ ID NO:1); ii) tryptophan at the position corresponding to position 30 of hPYY(1-36) (SEQ ID NO:1); iii) leucine at the position corresponding to position 31 of hPYY(1-36) (SEQ ID NO:1); iv) tyrosine at the position corresponding to position 28 of hPYY(1-36) (SEQ ID NO:1); v) isoleucine at the position corresponding to position 22 of hPYY(1-36) (SEQ ID NO:1); and vi) a modifying group attached to the epsilon amino group of said lysine at the position corresponding to position 7 or 10 of hPYY(1-36) (SEQ ID NO:1), and may comprise up to 10 amino acid modifications as compared to human PYY(3-36) (hPYY(3-36), SEQ ID NO:2).

In one aspect, the invention also relates to pharmaceutical compositions comprising such PYY compounds and pharmaceutically acceptable excipients, as well as the medical use of the PYY compounds.

Also or alternatively, in one aspect, the invention relates to PYY compounds being Y2 receptor agonists.

Also or alternatively, in one aspect, the invention relates to PYY compounds displaying selectivity towards the Y receptor subtype Y2 as compared to Y receptor subtypes Y1, Y4 and Y5.

Also or alternatively, in one aspect, the invention relates to PYY compounds with longer half-life than the half-life of hPYY(3-36). Also or alternatively, in one aspect, the invention relates to PYY compounds with longer half-life than the half-life of hPYY(1-36).

DESCRIPTION OF THE INVENTION

The invention relates to PYY compounds. In one aspect, the PYY compounds of the present invention have i) lysine at the position corresponding to position 7 or 10 of hPYY (1-36) (SEQ ID NO:1); ii) tryptophan at the position corresponding to position 30 of hPYY(1-36) (SEQ ID NO:1); iii) leucine at the position corresponding to position 31 of hPYY(1-36) (SEQ ID NO:1); iv) tyrosine at the position corresponding to position 28 of hPYY(1-36) (SEQ ID NO:1) and/or isoleucine at the position corresponding to position 22 of hPYY(1-36) (SEQ ID NO:1); and v) a modifying group attached to the epsilon amino group of said lysine at the position corresponding to position 7 or 10 of hPYY(1-36) (SEQ ID NO:1).

In another aspect, the PYY compounds of the present invention have i) lysine at the position corresponding to position 7 or 10 of hPYY(1-36) (SEQ ID NO:1); ii) tryptophan at the position corresponding to position 30 of hPYY(1-36) (SEQ ID NO:1); iii) leucine at the position corresponding to position 31 of hPYY(1-36) (SEQ ID NO:1); iv) tyrosine at the position corresponding to position 28 of hPYY(1-36) (SEQ ID NO:1); and v) a modifying group attached to the epsilon amino group of said lysine at the position corresponding to position 7 or 10 of hPYY(1-36) (SEQ ID NO:1).

In another aspect, the PYY compounds of the present invention have i) lysine at the position corresponding to position 7 or 10 of hPYY(1-36) (SEQ ID NO:1); ii) tryptophan at the position corresponding to position 30 of hPYY(1-36) (SEQ ID NO:1); iii) leucine at the position corresponding to position 31 of hPYY(1-36) (SEQ ID NO:1); iv) tyrosine at the position corresponding to position 28 of hPYY(1-36) (SEQ ID NO:1); v) isoleucine at the position corresponding to position 22 of hPYY(1-36) (SEQ ID NO:1); and vi) a modifying group attached to the epsilon amino group of said lysine at the position corresponding to position 7 or 10 of hPYY(1-36) (SEQ ID NO:1).

The PYY compounds of the present invention may comprise up to 10 amino acid modifications as compared to human PYY(3-36) (hPYY(3-36), SEQ ID NO:2).

In one aspect, the invention relates to PYY compounds being Y receptor subtype Y2 agonists.

Also or alternatively, in one aspect, the invention relates to PYY compounds displaying selectivity towards the Y receptor subtype Y2 as compared to Y receptor subtypes Y1, Y4 and Y5.

In one aspect peptides being "selective" for specific receptors over other receptors refers to peptides that display at least 10 fold, such as at least 20 fold, at least 50 fold, or at least 100 fold higher potency for one Y receptor over other Y receptors as measured in vitro in an assay for receptor function, such as an Actone functional potency assay, and compared by EC50 values, or a Scintillation Proximity Assay (SPA) measuring receptor binding affinity, and compared by Ki values.

In what follows, Greek letters may be represented by their symbol or the corresponding written name, for example: α=alpha; β=beta; ε=epsilon; γ=gamma; ω=omega; etc.

PYY Compounds

The term "hPYY(1-36)" as used herein refers to the human Peptide YY, the sequence of which is included in the sequence listing as SEQ ID NO:1. The peptide having the sequence of SEQ ID NO:1 may also be designated native hPYY.

The term "PYY compound" as used herein refers to a peptide, or a compound, which is a variant of hPYY(1-36). The term "PYY compound" as used herein may also refer to a peptide, or a compound, which is a variant of hPYY(3-36) (SEQ ID NO:2). The term "PYY compound" as used herein may also refer to a peptide, or a compound, which is a variant of hPYY(4-36).

The C-terminal of the PYY compounds of the present invention is an amide, as is the C-terminal of native hPYY (1-36) (SEQ ID NO:1) and hPYY(3-36) (SEQ ID NO:2), respectively.

The PYY compounds of the present invention can be PYY analogues and/or derivatives thereof.

The term "PYY analogue" is used for PYY compounds, where at least one amino acid modification in the backbone is present.

The term "PYY derivative" is used for PYY compounds comprising at least one non-amino acid substituent covalently attached.

A derivative of a PYY analogue is thus a PYY compound comprising at least one amino acid modification and at least one non-amino acid substituent covalently attached. The PYY compounds of the present invention may comprise up to 10 amino acid modifications as compared to hPYY(3-36) (SEQ ID NO:2).

The term "amino acid modification" used throughout this application is used in the meaning of a modification to an amino acid as compared to hPYY(3-36). This modification can be the result of a deletion of an amino acid, addition of an amino acid, or substitution of one amino acid with another.

In one aspect, the PYY compounds of the present invention comprise i) lysine at the position corresponding to position 7 or 10 of hPYY(1-36) (SEQ ID NO:1); ii) tryptophan at the position corresponding to position 30 of hPYY(1-36) (SEQ ID NO:1); iii) leucine at the position corresponding to position 31 of hPYY(1-36) (SEQ ID NO:1); and iv) tyrosine at the position corresponding to position 28 of hPYY(1-36) (SEQ ID NO:1), meaning that the PYY compounds of this aspect of the invention may comprise up to 6 amino acid modifications as compared to hPYY(3-36) in addition to these modification in the positions corresponding to positions 7, 30, 28, and 31 of hPYY (1-36) (SEQ ID NO:1).

In another aspect, the PYY compounds of the present invention comprise i) lysine at the position corresponding to position 7 or 10 of hPYY(1-36) (SEQ ID NO:1); ii) tryptophan at the position corresponding to position 30 of hPYY(1-36) (SEQ ID NO:1); iii) leucine at the position corresponding to position 31 of hPYY(1-36) (SEQ ID NO:1); iv) tyrosine at the position corresponding to position 28 of hPYY(1-36) (SEQ ID NO:1); and v) isoleucine at the position corresponding to position 22 of hPYY(1-36) (SEQ ID NO:1), meaning that the PYY compounds of this aspect of the invention may comprise up to 5 amino acid modifications as compared to hPYY(3-36) in addition to these modification in the positions corresponding to positions 7, 30, 22, 28, and 31 of hPYY(1-36) (SEQ ID NO:1).

As an example, [Arg4,Lys7,Gln18,Tyr28,Trp30,Leu31] hPYY(3-36) comprises 6 amino acid substitutions as compared to hPYY(3-36). As another example, [Arg4,Lys7, Gln18,Tyr28,Trp30,Leu31]hPYY(4-36) comprises 6 amino acid substitutions and 1 deletion as compared to hPYY(3-

36), meaning that this compound has 7 amino acid modifications as compared to hPYY(3-36).

PYY compounds or PYY analogues of the invention may be described by reference to i) the number of the amino acid residue in hPYY(1-36) (SEQ ID NO:1) which corresponds to the amino acid residue which is changed (i.e., the corresponding position in hPYY(1-36), and to ii) the actual change.

The expressions "a position equivalent to" or "corresponding position" are used to characterise the site of change in a variant PYY sequence by reference to hPYY (1-36).

In general throughout the application, when referring to a particular position of a PYY analogue, the position referred to is the position of the PYY analogue corresponding to that particular position of hPYY(1-36).

In the sequence listing, the first amino acid residue of a given sequence is assigned no. 1. This means that e.g. the first amino acid residue of hPYY(3-36), which is isoleucine, is assigned no. 3 in the sequence listings. Throughout this application however, this position is referred to as the position corresponding to position 3 of hPYY(1-36).

The expression used throughout this application, that a PYY compound comprises a particular amino acid at a position corresponding to a certain position of hPYY(1-36), means that the native amino acid in that position has been replaced with that particular amino acid.

The following is a non-limiting example of suitable analogue nomenclature. [Lys7,Tyr28,Trp30,Leu31]hPYY (3-36) designates an analogue of the human PYY(1-36), wherein the naturally occurring alanine in position 7 has been substituted with lysine, the naturally occurring leucine in position 28 has been substituted with tyrosine, the naturally occurring leucine in position 30 has been substituted with tryptophan, the naturally occurring valine in position 31 has been substituted with leucine, and tyrosine and proline in position 1 and 2, respectively, have been deleted. Likewise, [Lys7,Tyr28,Trp30,Leu31]hPYY(3-36) can also be said to designate an analogue of the human PYY(3-36), wherein the naturally occurring alanine in position 7 has been substituted with lysine, the naturally occurring leucine in position 28 has been substituted with tyrosine, the naturally occurring leucine in position 30 has been substituted with tryptophan, and the naturally occurring valine in position 31 has been substituted with leucine.

The following is a non-limiting example of suitable nomenclature for a derivative of a PYY analogue. N{alpha-4}-(3-Methylbutanoyl)-N{Epsilon-7}-[(4S)-4-carboxy-4-(17-carboxyheptadecanoylamino)butanoyl]-[Arg4,Lys7,Gln18,Tyr28,Trp30,Leu31]hPYY(4-36) designates a derivative of an analogue of hPYY(4-36), wherein [Arg4,Lys7,Gln18,Tyr28,Trp30,Leu31] designate the amino acid changes as compared to human PYY(4-36) with the numbers referring to the corresponding positions of PYY(1-36), and wherein the substituent 3-methylbutanoyl is attached to the alpha amino group of the N-terminal amino acid residue, and the substituent [(4S)-4-carboxy-4-(17-carboxyheptadecanoylamino)butanoyl] is attached to the epsilon amino group of the lysine in the position corresponding to position 7 in hPYY(1-36).

Amino acid residues may be identified by their full name, their one-letter code, and/or their three-letter code. These three ways are fully equivalent. Analogues "comprising" certain specified changes may comprise further changes, when compared to hPYY(1-36). In one aspect, the analogue "has" the specified changes.

PYY Analogues

A PYY analogue is a PYY peptide in which a number of amino acid residues have been modified when compared to hPYY(1-36) or hPYY(3-36). These modifications include substitutions, insertions, and/or deletions, alone or in combination.

In a specific aspect, the PYY analogues of the invention include one or more modifications of a "non-essential" amino acid residue. In the context of the invention, a "non-essential" amino acid residue is a residue that can be altered, i.e., deleted or substituted in the human PYY amino acid sequence without abolishing or substantially reducing the activity of the PYY analogue towards the Y2 receptor.

Substitutions.

In one aspect amino acids may be substituted by conservative substitution. The term "conservative substitution" as used herein denotes that one or more amino acids are replaced by another, biologically similar residue. Examples include substitution of amino acid residues with similar characteristics, e.g. small amino acids, acidic amino acids, polar amino acids, basic amino acids, hydrophobic amino acids and aromatic amino acids.

In one aspect, the PYY analogues of the invention may comprise substitutions of one or more unnatural and/or non-amino acids, e.g., amino acid mimetics, into the sequence of PYY.

Deletions and Truncations.

In one aspect, the PYY analogues of the invention may have one or more amino acid residues deleted from the amino acid sequence of human PYY, alone or in combination with one or more insertions or substitutions.

Insertions.

In one aspect, the PYY analogues of the invention may have one or more amino acid residues inserted into the amino acid sequence of human PYY, alone or in combination with one or more deletions and/or substitutions.

In one aspect, the PYY analogues of the invention may include insertions of one or more unnatural amino acids and/or non-amino acids into the sequence of PYY.

The PYY peptide may be derived from vertebrates, such as human, mouse, sheep, goat, cow, or horse. The term "vertebrate" means members of the subphylum Vertebrata, a primary division of the phylum Chordata that includes the fish, amphibians, reptiles, birds, and mammals, all of which are characterized by a segmented spinal column and a distinct well-differentiated head. The term "mammal" means humans as well as all other warm-blooded members of the animal kingdom possessed of a homeostatic mechanism in the class Mammalia, e.g., companion mammals, zoo mammals, and food-source mammals. Some examples of companion mammals are canines (e.g., dogs), felines (e.g., cats) and horses; some examples of food-source mammals are pigs, cattle, sheep, and the like. In one aspect the mammal is a human or a companion mammal. In one aspect the mammal is a human, male or female.

The term "peptide", as e.g. used in the context of the PYY compounds of the invention, refers to a compound which comprises a series of amino acids interconnected by amide (or peptide) bonds.

Amino acids are molecules containing an amine group and a carboxylic acid group, and, optionally, one or more additional groups, often referred to as a side chain.

The term "amino acid" includes proteinogenic (or coded or natural) amino acids (amongst the 20 standard amino acids), as well as non-proteinogenic (or non-coded or non-natural) amino acids. Proteinogenic amino acids are those which are naturally incorporated into proteins. The standard amino acids are those encoded by the genetic code. Non-proteinogenic amino acids are either not found in proteins, or not produced by standard cellular machinery (e.g., they may have been subject to post-translational modification). Non-limiting examples of non-proteinogenic amino acids are the D-isomers of the proteinogenic amino acids. One example of a D-isomer of a proteinogenic amino acid is the D-isomer of aspartic acid, which can also be written as D-Asp.

In what follows, all amino acids of the PYY compound for which the optical isomer is not stated is to be understood to mean the L-isomer (unless otherwise specified).

PYY Derivatives

The term "derivative" as used herein in the context of a PYY peptide or analogue means a chemically modified PYY peptide, in which one or more substituents have been covalently attached to the peptide.

In one aspect of the invention, the substituent may be an N-terminal substituent.

Also or alternatively, in one aspect, the substituent may be a modifying group or alternatively, referred to as a protracting moiety.

N-Terminal Substituent

In one aspect of the invention, the PYY compound comprises a substituent covalently attached to the alpha-amino group in the amino acid residue in the N-terminus of the PYY compound. In one aspect, the amino acid residues in the positions corresponding to positions 1-3 of hPYY(1-36) are absent, and the N-terminal substituent is covalently attached to the amino acid residue in the position corresponding to position 4 of hPYY(1-36).

In one aspect, the N-terminal substituent is an alkoxy group. In one aspect, the N-terminal substituent is an alkoxy group comprising up to 12 carbon atoms. In another aspect, the N-terminal substituent is an alkoxy group comprising up to 6 carbon atoms.

Modifying Group/Protracting Moiety

In one aspect, the PYY compound comprises a substituent or modifying group covalently attached to the amino acid residue in the position corresponding to position 7 or 10 of hPYY(1-36). In one further aspect, the substituent or modifying group is capable of forming non-covalent conjugates with proteins, thereby promoting the circulation of the derivative with the blood stream, and also having the effect of protracting the time of action of the derivative, due to the fact that the conjugate of the PYY derivative and albumin is only slowly removed by renal clearance. Thus, the substituent, or modifying group, as a whole may also be referred to as a protracting moiety.

The modifying group may be covalently attached to a lysine residue of the PYY peptide by acylation, i.e., via an amide bond formed between a carboxylic acid group of the modifying group and the epsilon amino group of the lysine residue. The amino group of lysine could also be coupled to an aldehyde of the modifying group by reductive amination. In another aspect the thiol group of cysteine could by coupled to a maleiimido group of the modifying group by Michael addition or coupled to the chloro- or iodoacetyl group of the modifying group by nucleophilic substitution.

In one aspect, the modifying group is covalently attached to a lysine residue in a position corresponding to position 7 or 10 of hPYY(1-36) by acylation, i.e., via an amide bond formed between a carboxylic acid group of the modifying group and the epsilon amino group of the lysine residue.

The derivatives of the invention may exist in different stereoisomeric forms having the same molecular formula and sequence of bonded atoms, but differing only in the three-dimensional orientation of their atoms in space. The stereoisomerism of the exemplified derivatives of the invention is indicated in the experimental section, in the names as well as the structures, using standard nomenclature. Unless otherwise stated the invention relates to all stereoisomeric forms of the claimed derivative.

Herein, all amino acids of the PYY compound for which the optical isomer is not stated are to be understood to mean the L-isomer (unless otherwise specified).

Pharmaceutically Acceptable Salts

The PYY compounds of the invention may be in the form of a pharmaceutically acceptable salt.

Salts are e.g. formed by a chemical reaction between a base and an acid, e.g.: $2NH_3 + H_2SO_4 \rightarrow (NH_4)_2SO_4$.

The salt may be a basic salt, an acidic salt, or it may be neither nor (i.e. a neutral salt). Basic salts produce hydroxide ions and acid salts hydronium ions in water.

The salts of the derivatives of the invention may be formed with added cations or anions between anionic or cationic groups, respectively. These groups may be situated in the peptide moiety, and/or in the side chain of the derivatives of the invention.

Non-limiting examples of anionic groups of the derivatives of the invention include free carboxylic groups in the side chain, if any, as well as in the peptide moiety. The peptide moiety often includes free carboxylic groups at internal acid amino acid residues such as Asp and Glu.

Non-limiting examples of cationic groups in the peptide moiety include the free amino group at the N-terminus, if present, as well as any free amino group of internal basic amino acid residues such as His, Arg, and Lys.

Functional Properties

In a first functional aspect, the PYY compounds of the invention have a good Y2 receptor potency. Also, or alternatively, in a second aspect, they bind very well to the Y2 receptor. Preferably they are full Y2 receptor agonists as is reflected by their ability to bind strongly to the Y2 receptor combined with the capacity to fully activate the receptor compared to hPYY(1-36) and hPYY(3-36).

Also or alternatively, in a second functional aspect, the invention relates to PYY compounds displaying selectivity towards the Y receptor subtype Y2 as compared to Y receptor subtypes Y1, Y4 and Y5.

Also, or alternatively, in a third functional aspect, the PYY compounds of the invention have improved pharmacokinetic properties. Also, or alternatively, in a fourth functional aspect, the PYY compounds of the invention have increased half-life and/or a decreased clearance. Also, or alternatively, in a fifth functional aspect, they have the effect in vivo of decreasing the blood glucose. Also, or alternatively, in a sixth functional aspect, they have the effect in vivo of decreasing food intake. Also, or alternatively, in a seventh functional aspect, they have the effect in vivo of decreasing body weight.

Biological Activity—In Vitro Potency

According to the first functional aspect, the PYY compounds of the invention are biologically active, or potent.

In a particular embodiment, potency and/or activity refers to in vitro potency, i.e. performance in a functional Y2 receptor assay, more in particular to the capability of activating the human Y2 receptor.

The term half maximal effective concentration ($EC_{50}$) generally refers to the concentration which induces a response halfway between the baseline and maximum, by reference to the dose response curve. $EC_{50}$ is used as a measure of the potency of a compound and represents the concentration where 50% of its maximal effect is observed.

The in vitro potency of the derivatives of the invention may be determined as described in Example 2, and the $EC_{50}$ of the derivative in question determined. The lower the $EC_{50}$ value, the better the potency.

In one aspect of the invention, the derivative of the invention has an in vitro potency determined using the method of Example 2 corresponding to an $EC_{50}$ at or below 10 nM. In one aspect, the derivative of the invention has an in vitro potency determined using the method of Example 2 corresponding to an $EC_{50}$ at or below 5 nM. In one aspect, the derivative of the invention has an in vitro potency determined using the method of Example 2 corresponding to an $EC_{50}$ at or below 1 nM.

Biological Activity—In Vitro Receptor Binding

According to the second functional aspect, the PYY compounds of the invention bind very well to the Y2 receptor. This may be determined as described in Example 3.

Generally, the binding to the Y2 receptor should be as good as possible, corresponding to a low Ki value. The Ki value is determined by the Cheng-Prusoff equation Ki=IC50/(1+[L]/Kd), wherein IC50 is the half maximal inhibitory concentration of the agonist, [L] is the concentration of the radioligand and Kd is the dissociation constant for binding.

As an example, in a particular aspect, the Y2 receptor binding affinity (Ki) is below 10 nM. In one aspect of the invention, the Y2 receptor binding affinity (Ki) is below 5 nM. In one aspect of the invention, the Y2 receptor binding affinity (Ki) is below 1 nM.

Biological Activity—In Vivo Pharmacology

In another particular embodiment the PYY compounds of the invention are potent in vivo, which may be determined as is known in the art in any suitable animal model, as well as in clinical trials.

The diabetic db/db mouse is one example of a suitable animal model, and the blood glucose lowering effect may be determined in such mice in vivo, e.g. as described in Example 5.

In addition, inhibition of food intake in the db/db mice is a suitable model for determination of effect on food intake and body weight as also described in Example 5.

Generally, the glucose lowering effect of a 5, 10 or 30 nmol/kg dose should be as good as possible corresponding to a low relative % glucose level.

As an example, in a particular aspect of the invention, 23 or 40 hours after dosing (5, 10 or 30 nmol/kg) the relative % glucose level is below 90%.

As an example, in a particular aspect of the invention, 23 or 40 hours after dosing 5 nmol/kg the % relative food intake is below 75%. As an example, in a particular aspect of the invention, 23 or 40 hours after dosing 10 nmol/kg the % relative food intake is below 65%. As an example, in a particular aspect of the invention, 23 or 40 hours after dosing 5 nmol/kg) the % relative food intake is below 50%.

Pharmacokinetics Profile

According to the third functional aspect, the PYY compounds of the invention have improved pharmacokinetic properties such as increased terminal half-life and/or decreased clearance.

Increasing terminal half-life and/or decreasing of the clearance means that the compound in question is eliminated slower from the body. For the compounds of the invention this entails an extended duration of pharmacological effect.

The pharmacokinetic properties of the derivatives of the invention may suitably be determined in-vivo in pharmacokinetic (PK) studies. Such studies are conducted to evaluate how pharmaceutical compounds are absorbed, distributed, and eliminated in the body, and how these processes affect the concentration of the compound in the body, over the course of time.

In the discovery and preclinical phase of pharmaceutical drug development, animal models such as the mouse, rat, monkey, dog, or pig, may be used to perform this characterisation. Any of these models can be used to test the pharmacokinetic properties of the derivatives of the invention.

The estimate of terminal half-life and/or clearance is relevant for evaluation of dosing regimens and an important parameter in drug development, in the evaluation of new drug compounds.

Pharmacokinetics Profile—Half Life In Vivo in Minipigs

According to the third functional aspect, the derivatives of the invention have improved pharmacokinetic properties.

In a particular embodiment, the pharmacokinetic properties may be determined as terminal half-life ($T_{1/2}$) in vivo in minipigs after i.v. administration, e.g. as described in Example 4 herein.

In one aspect of the invention, the terminal half-life in minipigs is at least 15 hours. In one aspect of the invention, the terminal half-life in minipigs is at least 20 hours. In yet another aspect of the invention, the terminal half-life in minipigs is at least 40 hours.

Production of PYY Compounds

The production of peptides like the PYY compounds of the present invention is well known in the art.

The PYY moiety of the derivatives of the invention may for instance be produced by classical peptide synthesis, e.g., solid phase peptide synthesis using t-Boc or Fmoc chemistry or other well established techniques, see, e.g., Greene and Wuts, "Protective Groups in Organic Synthesis", John Wiley & Sons, 1999, Florencio Zaragoza Dörwald, "Organic Synthesis on solid Phase", Wiley-VCH Verlag GmbH, 2000, and "Fmoc Solid Phase Peptide Synthesis", Edited by W. C. Chan and P. D. White, Oxford University Press, 2000.

Also, or alternatively, they may be produced by recombinant methods, viz. by culturing a host cell containing a DNA sequence encoding the analogue and capable of expressing the peptide in a suitable nutrient medium under conditions permitting the expression of the peptide. Non-limiting examples of host cells suitable for expression of these peptides are: *Escherichia coli, Saccharomyces cerevisiae*, as well as mammalian BHK or CHO cell lines.

The PYY compounds of the invention which include non-natural amino acids and/or covalently attached substituents may e.g. be produced as described in the experimental part.

Specific examples of methods of preparing a number of the PYY compounds of the invention are included in the experimental part.

Protein Purification

The PYY compounds of the present invention may be purified by a variety of procedures known in the art including, but not limited to, chromatography (e.g., ion exchange, affinity, hydrophobic, and reverse-phase high performance liquid chromatography (RP-HPLC)), electrophoretic procedures, or extraction (see, e.g., Protein Purification, J.-C. Janson and Lars Ryden, editors, VCH Publishers, New York, 1989).

Mode of Administration

The term "treatment" is meant to include both the prevention and minimization of the referenced disease, disorder, or condition (i.e., "treatment" refers to both prophylactic and therapeutic administration of the PYY compounds of the invention or composition comprising the PYY compounds of the invention) unless otherwise indicated or clearly contradicted by context.

The route of administration may be any route which effectively transports a compound of this invention to the desired or appropriate place in the body, such as parenterally, for example, subcutaneously, intramuscularly or intravenously. Alternatively, a compound of this invention can be administered orally, pulmonary, rectally, transdermally, buccally, sublingually, or nasally.

Pharmaceutical Compositions

Injectable compositions comprising PYY compounds of the present invention can be prepared using the conventional techniques of the pharmaceutical industry which involve dissolving and mixing the ingredients as appropriate to give the desired end product. Thus, according to one procedure, a PYY compound of this invention is dissolved in a suitable buffer at a suitable pH so precipitation is minimised or avoided. The injectable composition is made sterile, for example, by sterile filtration.

A composition may be a stabilised formulation. The term "stabilised formulation" refers to a formulation with increased physical and/or chemical stability, preferably both. In general, a formulation must be stable during use and storage (in compliance with recommended use and storage conditions) until the expiration date is reached.

The term "physical stability" refers to the tendency of the polypeptide to form biologically inactive and/or insoluble aggregates as a result of exposure to thermo-mechanical stress, and/or interaction with destabilising interfaces and surfaces (such as hydrophobic surfaces). The physical stability of an aqueous polypeptide formulation may be evaluated by means of visual inspection, and/or by turbidity measurements after exposure to mechanical/physical stress (e.g. agitation) at different temperatures for various time periods. Alternatively, the physical stability may be evaluated using a spectroscopic agent or probe of the conformational status of the polypeptide such as e.g. Thioflavin T or "hydrophobic patch" probes.

The term "chemical stability" refers to chemical (in particular covalent) changes in the polypeptide structure leading to formation of chemical degradation products potentially having a reduced biological potency, and/or increased immunogenic effect as compared to the intact polypeptide. The chemical stability can be evaluated by measuring the amount of chemical degradation products at various time-points after exposure to different environmental conditions, e.g. by SEC-HPLC, and/or RP-HPLC.

In one aspect, the invention provides PYY compounds with improved physical stability. In one aspect, the invention provides PYY compounds with improved chemical stability.

Combination Treatment

The treatment with a PYY compound according to the present invention may also be combined with one or more additional pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity.

Examples of these pharmacologically active substances are: GLP-1 receptor agonists, insulin, DPP-IV (dipeptidyl peptidase-IV) inhibitors, amylin agonists and leptin receptor agonists.

In one aspect of the invention, a PYY compound according to the present invention is combined with a GLP-1 agonist. The compounds may be supplied in a single-dosage form wherein the single-dosage form contains both compounds, or in the form of a kit-of-parts comprising a preparation of the PYY compound as a first unit dosage form and a preparation of the GLP-1 agonist as a second unit dosage form.

Non-limiting examples of GLP-1 agonists to be combined with the PYY compounds of the present invention are liraglutide, semaglutide, exenatide, dulaglutide, lixisenatide, taspoglutide, and albiglutide.

Liraglutide, a mono-acylated GLP-1 derivative for once daily administration which is marketed as of 2009 by Novo Nordisk A/S, is disclosed in WO 98/08871.

WO 2006/097537 discloses additional GLP-1 derivatives including semaglutide, a mono-acylated GLP-1 derivative for once weekly administration which is under development by Novo Nordisk A/S.

Exenatide is a synthetic version of exendin-4, a hormone found in the saliva of the Gila monster. It displays biological properties similar to GLP-1.

Dulaglutide is a GLP-1-Fc construct (GLP-1-linker-Fc from IgG4).

Lixisenatide is based on exendin-4 (1-39) modified C-terminally with six Lys residues.

Taspoglutide is the 8-(2-methylalanine)-35-(2-methylalanine)-36-L-argininamide derivative of the amino acid sequence 7-36 of human GLP-1.

Albiglutide is a recombinant human serum albumin (HSA)-GLP-1 hybrid protein, likely a GLP-1 dimer fused to HSA. The constituent GLP-1 peptide is an analogue, in which Ala at position 8 has been substituted by Gly.

Pharmaceutical Indications

The present invention also relates to a PYY compound of the invention for use as a medicament.

In particular aspects of the invention, the PYY compounds of the invention may be used for the following medical treatments:

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(v) prevention and/or treatment of diabetic complications, such as angiopathy; neuropathy, including peripheral neuropathy; nephropathy; and/or retinopathy;

(vi) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(vii) prevention and/or treatment of cardiovascular diseases; and/or (viii) prevention and/or treatment of sleep apnoea.

(ix) weight maintenance after successful weight loss (either drug induced or by diet and exercise)—i.e. prevention of weight gain after successful weight loss.

The following indications are particularly preferred: Type 2 diabetes, and/or obesity.

In one aspect, a method is disclosed herein for altering energy metabolism in a subject. The method includes administering a therapeutically effective amount of a PYY compound of the invention to the subject, thereby altering energy expenditure. Energy is burned in all physiological processes. The body can alter the rate of energy expenditure directly, by modulating the efficiency of those processes, or changing the number and nature of processes that are occurring. For example, during digestion the body expends energy moving food through the bowel, and digesting food, and within cells, the efficiency of cellular metabolism can be altered to produce more or less heat.

In one aspect a method is disclosed herein for any and all manipulations of the accurate circuitry described in this application, which alter food intake co-ordinately and reciprocally alter energy expenditure. Energy expenditure is a result of cellular metabolism, protein synthesis, metabolic rate, and calorie utilization. Thus, in this embodiment, peripheral administration results in increased energy expenditure, and decreased efficiency of calorie utilization. In one aspect, a therapeutically effective amount of a PYY compound according to the invention is administered to a subject, thereby increasing energy expenditure.

In some embodiments the invention relates to a method for weight management. In some embodiments the invention relates to a method for reduction of appetite. In some embodiments the invention relates to a method for reduction of food intake.

Generally, all subjects suffering from obesity are also considered to be suffering from overweight. In some embodiments the invention relates to a method for treatment or prevention of obesity. In some embodiments the invention relates to use of the PYY compounds of the present invention for treatment or prevention of obesity. In some embodiments the subject suffering from obesity is human, such as an adult human or a paediatric human (including infants, children, and adolescents). Body mass index (BMI) is a measure of body fat based on height and weight. The formula for calculation is BMI=weight in kilograms/(height in meters)$^2$. A human subject suffering from obesity may have a BMI of ≥30; this subject may also be referred to as obese. In some embodiments the human subject suffering from obesity may have a BMI of ≥35 or a BMI in the range of ≥30 to <40. In some embodiments the obesity is severe obesity or morbid obesity, wherein the human subject may have a BMI of ≥40.

In some embodiments the invention relates to a method for treatment or prevention of overweight, optionally in the presence of at least one weight-related comorbidity. In some embodiments the invention relates to use of the PYY compounds of the present invention for treatment or prevention of overweight, optionally in the presence of at least one weight-related comorbidity.

In some embodiments the subject suffering from overweight is human, such as an adult human or a paediatric human (including infants, children, and adolescents). In some embodiments a human subject suffering from overweight may have a BMI of ≥25, such as a BMI of ≥27. In some embodiments a human subject suffering from overweight has a BMI in the range of 25 to <30 or in the range of 27 to <30. In some embodiments the weight-related comorbidity is selected from the group consisting of hypertension, diabetes (such as type 2 diabetes), dyslipidaemia, high cholesterol, and obstructive sleep apnoea.

In some embodiments the invention relates to a method for reduction of body weight. In some embodiments the invention relates to use of the PYY compounds of the present invention for reduction of body weight. A human to be subjected to reduction of body weight according to the present invention may have a BMI of ≥25, such as a BMI of ≥27 or a BMI of ≥30. In some embodiments the human to be subjected to reduction of body weight according to the present invention may have a BMI of ≥35 or a BMI of ≥40. The term "reduction of body weight" may include treatment or prevention of obesity and/or overweight.

Particular Embodiments

The invention is further described by the following non-limiting embodiments of the invention:

1. A PYY compound having a maximum of 10 amino acid modifications as compared to hPYY(3-36) (SEQ ID NO:2), wherein the PYY compound comprises i) lysine at the position corresponding to position 7 or 10 of hPYY(1-36) (SEQ ID NO: 1);

ii) tryptophan at the position corresponding to position 30 of hPYY(1-36) (SEQ ID NO: 1);

iii) leucine at the position corresponding to position 31 of hPYY(1-36) (SEQ ID NO: 1);

iv) tyrosine at the position corresponding to position 28 of hPYY(1-36) (SEQ ID NO:1) and/or isoleucine at the position corresponding to position 22 of hPYY(1-36) (SEQ ID NO:1); and v) a modifying group attached to the epsilon amino group of said lysine at the position corresponding to position 7 or 10 of hPYY(1-36) (SEQ ID NO:1), wherein said modifying group is defined by A-[B]$_r$—C— or A-[B]$_r$—C—[B]$_w$—, wherein A- is selected from Chem. 1 and Chem. 2

$$HOOC-(CH_2)_p-CO-*, \qquad \text{Chem. 1:}$$

$$HO_3S-(CH_2)_q-CO-* \qquad \text{Chem. 2:}$$

wherein p is an integer in the range of 12-18, and q is an integer in the range of 15-17;

B— is Chem. 3

$$*[NH-CH(COOH)-(CH_2)_2-CO-]-*, \qquad \text{Chem. 3:}$$

r is an integer in the range of 1-3;
w is an integer in the range of 1-3;
and
C— is absent or selected from Chem. 4 and Chem. 5

$$*[NH-(CH_2)_2-[O-(CH_2)_2]_s-O-(CH_2)_t-CO-]_u-* \qquad \text{Chem. 4:}$$

$$*[NH-(CH_2)_v-CO-]_x-* \qquad \text{Chem. 5:}$$

wherein s is an integer in the range of 1-3, t is an integer in the range of 1-3, u is an integer in the range of 1-4, v is an integer in the range of 3-7, and x is an integer in the range of 1-3;

wherein * denotes the points of attachment, wherein A, B, and C are interconnected via amide bonds and in the sequence indicated via said point of attachments; or a pharmaceutically acceptable salt, amide, or ester of said PYY compound; and wherein if the modifying group is A-B—C—B, C cannot be absent.

2. A PYY compound having a maximum of 10 amino acid modifications as compared to hPYY(3-36) (SEQ ID NO:2), wherein the PYY compound comprises
i) lysine at the position corresponding to position 7 or 10 of hPYY(1-36) (SEQ ID NO: 1);
ii) tryptophan at the position corresponding to position 30 of hPYY(1-36) (SEQ ID NO: 1);
iii) leucine at the position corresponding to position 31 of hPYY(1-36) (SEQ ID NO: 1);
iv) tyrosine at the position corresponding to position 28 of hPYY(1-36) (SEQ ID NO:1); and
v) a modifying group attached to the epsilon amino group of said lysine at the position corresponding to position 7 or 10 of hPYY(1-36) (SEQ ID NO:1),
wherein said modifying group is defined by A-[B]$_r$—C— or A-[B]$_r$—C—[B]$_w$—, wherein
A- is selected from Chem. 1 and Chem. 2

HOOC—(CH$_2$)$_p$—CO—*,    Chem. 1:

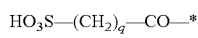
HO$_3$S—(CH$_2$)$_q$—CO—*    Chem. 2:

wherein p is an integer in the range of 12-18, and q is an integer in the range of 15-17;
B— is Chem. 3

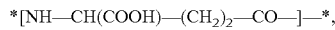
*[NH—CH(COOH)—(CH$_2$)$_2$—CO—]—*,    Chem. 3:

r is an integer in the range of 1-3;
w is an integer in the range of 1-3;
and
C— is absent or selected from Chem. 4 and Chem. 5

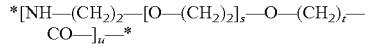
*[NH—(CH$_2$)$_2$—[O—(CH$_2$)$_2$]$_s$—O—(CH$_2$)$_t$—CO—]$_u$—*    Chem. 4:

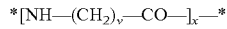
*[NH—(CH$_2$)$_v$—CO—]$_x$—*    Chem. 5:

wherein s is an integer in the range of 1-3, t is an integer in the range of 1-3, u is an integer in the range of 1-4, v is an integer in the range of 3-7, and x is an integer in the range of 1-3;
wherein * denotes the points of attachment,
wherein A, B, and C are interconnected via amide bonds and in the sequence indicated via said point of attachments; or a pharmaceutically acceptable salt, amide, or ester of said PYY compound; and
wherein if the modifying group is A-B—C—B, C cannot be absent.

3. A PYY compound having a maximum of 10 amino acid modifications as compared to hPYY(3-36) (SEQ ID NO:2), wherein the PYY compound comprises
i) lysine at the position corresponding to position 7 or 10 of hPYY(1-36) (SEQ ID NO: 1);
ii) tryptophan at the position corresponding to position 30 of hPYY(1-36) (SEQ ID NO: 1);
iii) leucine at the position corresponding to position 31 of hPYY(1-36) (SEQ ID NO: 1);
iv) tyrosine at the position corresponding to position 28 of hPYY(1-36) (SEQ ID NO: 1);
v) isoleucine at the position corresponding to position 22 of hPYY(1-36) (SEQ ID NO:1); and
vi) a modifying group attached to the epsilon amino group of said lysine at the position corresponding to position 7 or 10 of hPYY(1-36) (SEQ ID NO:1), wherein said modifying group is defined by A-[B]$_r$—C— or A-[B]$_r$—C—[B]$_w$—, wherein
A- is selected from Chem. 1 and Chem. 2

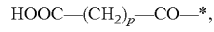
HOOC—(CH$_2$)$_p$—CO—*,    Chem. 1:

HO$_3$S—(CH$_2$)$_q$—CO—*    Chem. 2:

wherein p is an integer in the range of 12-18, and q is an integer in the range of 15-17;
B— is Chem. 3

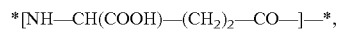
*[NH—CH(COOH)—(CH$_2$)$_2$—CO—]—*,    Chem. 3:

r is an integer in the range of 1-3;
w is an integer in the range of 1-3;
and
C— is absent or selected from Chem. 4 and Chem. 5

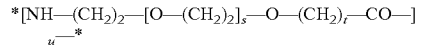
*[NH—(CH$_2$)$_2$—[O—(CH$_2$)$_2$]$_s$—O—(CH$_2$)$_t$—CO—]$_u$—*    Chem. 4:

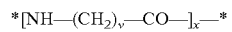
*[NH—(CH$_2$)$_v$—CO—]$_x$—*    Chem. 5:

wherein s is an integer in the range of 1-3, t is an integer in the range of 1-3, u is an integer in the range of 1-4, v is an integer in the range of 3-7, and x is an integer in the range of 1-3;
wherein * denotes the points of attachment,
wherein A, B, C and D are interconnected via amide bonds and in the sequence indicated via said point of attachments; or a pharmaceutically acceptable salt, amide, or ester of said PYY compound; and wherein if the modifying group is A-B—C—B, C cannot be absent.

4. A PYY compound according to any one of the preceding embodiments, wherein
A- is selected from Chem. 1 and Chem. 2

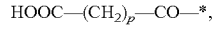
HOOC—(CH$_2$)$_p$—CO—*,    Chem. 1:

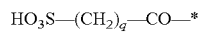
HO$_3$S—(CH$_2$)$_q$—CO—*    Chem. 2:

and wherein p is an integer in the range of 16-18, and q is 15.

5. A PYY compound according to any one of the preceding embodiments, wherein
A- is Chem. 1

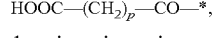
HOOC—(CH$_2$)$_p$—CO—*,    Chem. 1:

and wherein p is an integer in the range of 12-18.

6. A PYY compound according to any one of the preceding embodiments, wherein
A- is Chem. 1

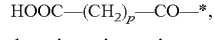
HOOC—(CH$_2$)$_p$—CO—*,    Chem. 1:

and wherein p is an integer in the range of 14-18.

7. A PYY compound according to any one of the preceding embodiments, wherein
A- is Chem. 1

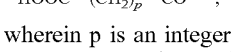
HOOC—(CH$_2$)$_p$—CO—*,    Chem. 1:

and wherein p is an integer in the range of 16-18.

8. A PYY compound according to any one of the preceding embodiments, wherein
A- is Chem. 1

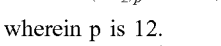
HOOC—(CH$_2$)$_p$—CO—*,    Chem. 1:

and wherein p is 12.

9. A PYY compound according to any one of the preceding embodiments, wherein
A- is Chem. 1

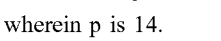
HOOC—(CH$_2$)$_p$—CO—*,    Chem. 1:

and wherein p is 14.

10. A PYY compound according to any one of the preceding embodiments, wherein
A- is Chem. 1

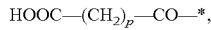    Chem. 1:

and wherein p is 16.

11. A PYY compound according to any one of the preceding embodiments, wherein
A- is Chem. 1

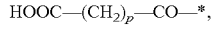    Chem. 1:

and wherein p is 18.

12. A PYY compound according to any one of the preceding embodiments, wherein
A- is Chem. 2

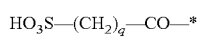    Chem. 2:

wherein q is an integer in the range of 15-17.

13. A PYY compound according to any one of the preceding embodiments, wherein
A- is Chem. 2

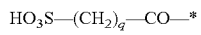    Chem. 2:

wherein q is 15.

14. A PYY compound according to any one of the preceding embodiments, wherein
A- is Chem. 2

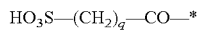    Chem. 2:

wherein q is 16.

15. A PYY compound according to any one of the preceding embodiments, wherein
A- is Chem. 2

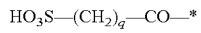    Chem. 2:

wherein q is 17.

16. A PYY compound according to any one of the preceding embodiments, wherein
B— is Chem. 3

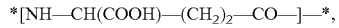    Chem. 3:

r is an integer in the range of 1-2;
w is an integer in the range of 1-2.

17. A PYY compound according to any one of the preceding embodiments, wherein
B— is Chem. 3

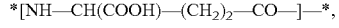    Chem. 3:

r is an integer in the range of 1-2.

18. A PYY compound according to any one of the preceding embodiments, wherein
B— is Chem. 3

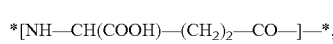    Chem. 3:

r is 1; w is 1.

19. A PYY compound according to any one of the preceding embodiments, wherein
B— is Chem. 3

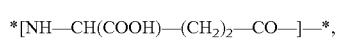    Chem. 3:

r is 1.

20. A PYY compound according to any one of the preceding embodiments, wherein
B— is Chem. 3

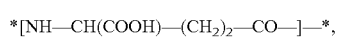    Chem. 3:

r is 2; w is 2.

21. A PYY compound according to any one of the preceding embodiments, wherein
B— is Chem. 3

    Chem. 3:

r is 2.

22. A PYY compound according to any one of the preceding embodiments, wherein
B— is Chem. 3

    Chem. 3:

r is 1; w is 2.

23. A PYY compound according to any one of the preceding embodiments, wherein
B— is Chem. 3

    Chem. 3:

r is 2; w is 1.

24. A PYY compound according to any one of the preceding embodiments, wherein
C— is absent or selected from Chem. 4a and Chem. 5a

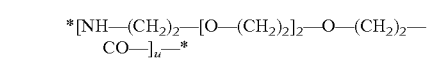    Chem. 4a:

    Chem. 5a:

wherein u is an integer in the range of 1-4, and x is an integer in the range of 1-3.

25. A PYY compound according to any one of the preceding embodiments, wherein
C— is absent or selected from Chem. 4a and Chem. 5a

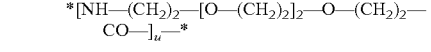    Chem. 4a:

    Chem. 5a:

wherein u is an integer in the range of 1-2, and x is 1.

26. A PYY compound according to any one of the preceding embodiments, wherein
C— is absent.

27. A PYY compound according to any one of the preceding embodiments, wherein
C— is Chem. 4a

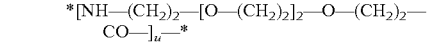    Chem. 4a:

wherein u is an integer in the range of 1-2.

28. A PYY compound according to any one of the preceding embodiments, wherein
C— is Chem. 4a

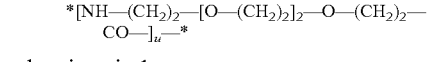    Chem. 4a:

wherein u is 1.

29. A PYY compound according to any one of the preceding embodiments, wherein
C— is Chem. 4a

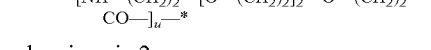    Chem. 4a:

wherein u is 2.

30. A PYY compound according to any one of the preceding embodiments, wherein
C— is Chem. 5a

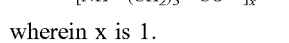    Chem. 5a:

wherein x is 1.

31. A PYY compound according to any one of the preceding embodiments, wherein
C— is Chem. 5a $$*[NH-(CH_2)_5-CO-]_x-*  \quad\quad \text{Chem. 5a:}$$

wherein x is 2.

32. A PYY compound according to any one of the preceding embodiments, wherein
A- is Chem. 1

$$HOOC-(CH_2)_p-CO-*, \quad\quad \text{Chem. 1:}$$

wherein p is an integer in the range of 16-18;
B— is Chem. 3

$$*[NH-CH(COOH)-(CH_2)_2-CO-]-*, \quad\quad \text{Chem. 3:}$$

r is 1; and
C— is absent.

33. A PYY compound according to any one of the preceding embodiments, wherein
A- is Chem. 1

$$HOOC-(CH_2)_p-CO-*, \quad\quad \text{Chem. 1:}$$

wherein p is an integer in the range of 16-18;
B— is Chem. 3

$$*[NH-CH(COOH)-(CH_2)_2-CO-]-*, \quad\quad \text{Chem. 3:}$$

wherein r is 2; and
C— is absent.

34. A PYY compound according to any one of the preceding embodiments, wherein
A- is Chem. 2

$$HO_3S-(CH_2)_q-CO-* \quad\quad \text{Chem. 2:}$$

wherein q is an integer in the range of 15-17;
B— is Chem. 3

$$*[NH-CH(COOH)-(CH_2)_2-CO-]-*, \quad\quad \text{Chem. 3:}$$

wherein r is 1; and
C— is absent.

35. A PYY compound according to any one of the preceding embodiments, wherein
A- is Chem. 2

$$HO_3S-(CH_2)_q-CO-* \quad\quad \text{Chem. 2:}$$

wherein q is 15;
B— is Chem. 3

$$*[NH-CH(COOH)-(CH_2)_2-CO-]-*, \quad\quad \text{Chem. 3:}$$

wherein r is 1; and
C— is absent.

36. A PYY compound according to any one of the preceding embodiments, wherein
A- is Chem. 2

$$HO_3S-(CH_2)_q-CO-* \quad\quad \text{Chem. 2:}$$

wherein q is 15;
B— is Chem. 3

$$*[NH-CH(COOH)-(CH_2)_2-CO-]-*, \quad\quad \text{Chem. 3:}$$

wherein r is 2; and
C— is absent.

37. A PYY compound according to any one of the preceding embodiments, wherein
A- is Chem. 1

$$HOOC-(CH_2)_p-CO-*, \quad\quad \text{Chem. 1:}$$

wherein p is an integer in the range of 12-18;
B— is Chem. 3

$$*[NH-CH(COOH)-(CH_2)_2-CO-]-*, \quad\quad \text{Chem. 3:}$$

wherein r is an integer in range of 1-3; and
C— is Chem. 4

$$*[NH-(CH_2)_2-[O-(CH_2)_2]_s-O-(CH_2)_t-CO-]_u-* \quad\quad \text{Chem. 4:}$$

wherein s is an integer in the range of 1-3, t is an integer in the range of 1-3, u is an integer in the range of 1-4.

38. A PYY compound according to any one of the preceding embodiments, wherein
A- is Chem 2: $HO_3S-(CH_2)_q-CO-*$
wherein q is an integer in the range of 15-17;
B— is Chem. 3

$$*[NH-CH(COOH)-(CH_2)_2-CO-]-*, \quad\quad \text{Chem. 3:}$$

wherein r is an integer in range of 1-3; and
C— is Chem. 4

$$*[NH-(CH_2)_2-[O-(CH_2)_2]_s-O-(CH_2)_t-CO-]_u-* \quad\quad \text{Chem. 4:}$$

wherein s is an integer in the range of 1-3, t is an integer in the range of 1-3, u is an integer in the range of 1-4.

39. A PYY compound according to any one of the preceding embodiments, wherein
A- is Chem. 1

$$HOOC-(CH_2)_p-CO-*, \quad\quad \text{Chem. 1:}$$

wherein p is an integer in the range of 12-18;
B— is Chem. 3

$$*[NH-CH(COOH)-(CH_2)_2-CO-]-*, \quad\quad \text{Chem. 3:}$$

wherein r is an integer in range of 1-3; and
C— is Chem. 5

$$*[NH-(CH_2)_v-CO-]_x-* \quad\quad \text{Chem. 5:}$$

wherein v is an integer in the range of 3-7, and x is an integer in the range of 1-3.

40. A PYY compound according to any one of the preceding embodiments, wherein
A- is Chem 2: $HO_3S-(CH_2)_q-CO-*$
wherein q is an integer in the range of 15-17;
B— is Chem. 3

$$*[NH-CH(COOH)-(CH_2)_2-CO-]-*, \quad\quad \text{Chem. 3:}$$

wherein r is an integer in range of 1-3; and
C— is Chem. 5

$$*[NH-(CH_2)_v-CO-]_x-* \quad\quad \text{Chem. 5:}$$

wherein v is an integer in the range of 3-7, and x is an integer in the range of 1-3.

41. A PYY compound according to any one of the preceding embodiments, wherein
A- is Chem. 1

$$HOOC-(CH_2)_p-CO-*, \quad\quad \text{Chem. 1:}$$

and wherein p is an integer in the range of 16-18;
B— is Chem. 3

$$*[NH-CH(COOH)-(CH_2)_2-CO-]-*, \quad\quad \text{Chem. 3:}$$

wherein r is 1; and
C— is Chem. 4a $$*[NH-(CH_2)_2-[O-(CH_2)_2]_2-O-(CH_2)_2-CO-]_u-* \quad\quad \text{Chem. 4a:}$$

wherein u is 1.

42. A PYY compound according to any one of the preceding embodiments, wherein
A— is Chem. 1

$$HOOC—(CH_2)_p—CO—*, \quad \text{Chem. 1:}$$

and wherein p is an integer in the range of 16-18;
B— is Chem. 3

$$*[NH—CH(COOH)—(CH_2)_2—CO—]—*, \quad \text{Chem. 3:}$$

wherein r is 1; and
C— is Chem. 4a $$*[NH—(CH_2)_2—[O—(CH_2)_2]_2—O—(CH_2)_2—CO—]_u—* \quad \text{Chem. 4a:}$$

wherein u is 2.

43. A PYY compound according to any one of the preceding embodiments, wherein
A— is Chem. 1

$$HOOC—(CH_2)_p—CO—*, \quad \text{Chem. 1:}$$

and wherein p is an integer in the range of 16-18;
B— is Chem. 3

$$*[NH—CH(COOH)—(CH_2)_2—CO—]—*, \quad \text{Chem. 3:}$$

and wherein r is 1; and
C— is Chem. 5a $$*[NH—(CH_2)_5—CO—]_x—* \quad \text{Chem. 5a:}$$

wherein x is 1.

44. A PYY compound according to any one of the preceding embodiments, wherein
A— is Chem 2: $HO_3S—(CH_2)_q—CO—*$
wherein q is an integer in the range of 15-17;
B— is Chem. 3

$$*[NH—CH(COOH)—(CH_2)_2—CO—]—*, \quad \text{Chem. 3:}$$

wherein r is 1; and
C— is Chem. 4a $$*[NH—(CH_2)_2—[O—(CH_2)_2]_2—O—(CH_2)_2—CO—]_u—* \quad \text{Chem. 4a:}$$

wherein u is 1.

45. A PYY compound according to any one of the preceding embodiments, wherein
A— is Chem 2: $HO_3S—(CH_2)_q—CO—*$
wherein q is an integer in the range of 15-17;
B— is Chem. 3

$$*[NH—CH(COOH)—(CH_2)_2—CO—]—*, \quad \text{Chem. 3:}$$

wherein r is 1; and
and
C— is Chem. 5a $$*[NH—(CH_2)_5—CO—]_x—* \quad \text{Chem. 5a:}$$

wherein x is 1.

46. A PYY compound according to any one of the preceding embodiments, wherein the PYY compound comprises glutamine at the position corresponding to position 18 of hPYY(1-36) (SEQ ID NO:1).

47. A PYY compound according to any one of the preceding embodiments, wherein the PYY compound comprises arginine or glycine at the position corresponding to position 4 of hPYY(1-36) (SEQ ID NO: 1).

48. A PYY compound according to any one of the preceding embodiments, wherein the PYY compound comprises arginine at the position corresponding to position 4 of hPYY (1-36) (SEQ ID NO:1).

49. A PYY compound according to any one of the preceding embodiments, wherein the PYY compound comprises proline, serine, or threonine at the position corresponding to position 9 of hPYY(1-36) (SEQ ID NO:1).

50. A PYY compound according to any one of the preceding embodiments, wherein the PYY compound comprises threonine at the position corresponding to position 13 of hPYY (1-36) (SEQ ID NO:1).

51. A PYY compound according to any one of the preceding embodiments, wherein the PYY compound comprises glutamic acid or valine at the position corresponding to position 22 of hPYY(1-36) (SEQ ID NO:1).

52. A PYY compound according to any one of the preceding embodiments, wherein the PYY compound comprises glutamic acid at the position corresponding to position 23 of hPYY(1-36) (SEQ ID NO:1)

53. A PYY compound according to any one of the preceding embodiments, wherein the PYY compound comprises alanine or isoleucine at the position corresponding to position 24 of hPYY(1-36) (SEQ ID NO:1).

54. A PYY compound according to any one of the preceding embodiments, wherein the positions corresponding to positions 1 and 2 of hPYY(1-36) (SEQ ID NO:1) are absent.

55. A PYY compound according to any one of the preceding embodiments, wherein the positions corresponding to positions 1-3 of hPYY(1-36) (SEQ ID NO:1) are absent.

56. A PYY compound according to any one of the preceding embodiments, wherein the positions corresponding to positions 1-3 of hPYY(1-36) (SEQ ID NO:1) are absent, and wherein the PYY compound further comprises an N-terminal substituent, wherein the N-terminal substituent is an alkoxy group comprising up to 12 carbon atoms.

57. A PYY compound according to embodiment 56, wherein the N-terminal substituent is an alkoxy group comprising up to 10 carbon atoms.

58. A PYY compound according to embodiment 56, wherein the N-terminal substituent is an alkoxy group comprising up to 8 carbon atoms.

59. A PYY compound according to embodiment 56, wherein the N-terminal substituent is an alkoxy group comprising up to 6 carbon atoms.

60. A PYY compound according to embodiment 56, wherein the N-terminal substituent is 3-methylbutanoyl.

61. A PYY compound according to embodiment 56, wherein the N-terminal substituent is acetyl.

62. A PYY compound according to any one of the preceding embodiments, wherein the PYY compound has a maximum of 9 amino acid modifications as compared to hPYY(3-36) (SEQ ID NO:2).

63. A PYY compound according to any one of the preceding embodiments, wherein the PYY compound has a maximum of 8 amino acid modifications as compared to hPYY(3-36) (SEQ ID NO:2).

64. A PYY compound according to any one of the preceding embodiments, wherein the PYY compound has a maximum of 7 amino acid modifications as compared to hPYY(3-36) (SEQ ID NO:2).

65. A PYY compound according to any one of the preceding embodiments, wherein the PYY compound has a maximum of 6 amino acid modifications as compared to hPYY(3-36) (SEQ ID NO:2).

66. A PYY compound according to any one of the preceding embodiments, wherein the PYY compound has a maximum of 5 amino acid modifications as compared to hPYY(3-36) (SEQ ID NO:2).

67. A PYY compound according to any one of the preceding embodiments, wherein the PYY compound has a minimum of 2 amino acid modifications as compared to hPYY(3-36) (SEQ ID NO:2).

68. A PYY compound according to any one of the preceding embodiments, wherein the PYY compound has a minimum of 3 amino acid modifications as compared to hPYY(3-36) (SEQ ID NO:2).
69. A PYY compound according to any one of the preceding embodiments, wherein the PYY compound has a minimum of 4 amino acid modifications as compared to hPYY(3-36) (SEQ ID NO:2).
70. A PYY compound according to any one of the preceding embodiments, wherein the PYY compound has a minimum of 5 amino acid modifications as compared to hPYY(3-36) (SEQ ID NO:2).
71. A PYY compound according to any one of the preceding embodiments, wherein the PYY compound has a minimum of 6 amino acid modifications as compared to hPYY(3-36) (SEQ ID NO:2).
72. A PYY compound according to any one of the preceding embodiments, wherein the PYY compound has a minimum of 7 amino acid modifications as compared to hPYY(3-36) (SEQ ID NO:2).
73. A PYY compound according to any one of the preceding embodiments, wherein the PYY compound has a minimum of 8 amino acid modifications as compared to hPYY(3-36) (SEQ ID NO:2).
74. A PYY compound according to any one of the preceding embodiments, wherein the PYY compound has in the range of 4 to 10 amino acid modifications as compared to hPYY (3-36) (SEQ ID NO:2).
75. A PYY compound according to any one of the preceding embodiments, wherein the PYY compound has in the range of 6 to 8 amino acid modifications as compared to hPYY (3-36) (SEQ ID NO:2).
76. A PYY compound according to any one of the preceding embodiments, wherein the PYY compound has in the range of 4 to 6 amino acid modifications as compared to hPYY (3-36) (SEQ ID NO:2).
77. A PYY compound according to any one of the preceding embodiments, wherein the PYY compound has 4 amino acid modifications as compared to hPYY(3-36) (SEQ ID NO:2).
78. A PYY compound according to any one of the preceding embodiments, wherein the PYY compound has 5 amino acid modifications as compared to hPYY(3-36) (SEQ ID NO:2).
79. A PYY compound according to any one of the preceding embodiments, wherein the PYY compound has 6 amino acid modifications as compared to hPYY(3-36) (SEQ ID NO:2).
80. A PYY compound according to any one of the preceding embodiments, wherein the PYY compound has 7 amino acid modifications as compared to hPYY(3-36) (SEQ ID NO:2).
81. A PYY compound according to any one of the preceding embodiments, wherein the PYY compound has 8 amino acid modifications as compared to hPYY(3-36) (SEQ ID NO:2).
82. A PYY compound according to any one of the preceding embodiments, wherein the PYY compound has 9 amino acid modifications as compared to hPYY(3-36) (SEQ ID NO:2).
83. A PYY compound according to any one of the preceding embodiments selected from the following:
N{Epsilon-7}-[(4S)-4-carboxy-4-[[(4S)-4-carboxy-4-(17-carboxyheptadecanoylamino)-butanoyl]amino]butanoyl]-[Arg4,Lys7,Gln18,Tyr28,Trp30,Leu31]hPYY(3-36) (Compound 1);
N{alpha-4}-(3-Methylbutanoyl)-N{Epsilon-7}-[(4S)-4-carboxy-4-(17-carboxy-heptadecanoylamino)butanoyl]-[Arg4,Lys7,Gln18,Tyr28,Trp30,Leu31]hPYY(4-36) (Compound 2);
N{alpha-4}-(3-Methylbutanoyl)-N{Epsilon-7}-[2-[2-[2-[[2-[2-[2-[[(4S)-4-carboxy-4-(17-carboxyheptadecanoylamino)butanoyl]amino]ethoxy]ethoxy]acetyl]amino]-ethoxy]ethoxy]acetyl]-[Arg4,Lys7,Gln18,Tyr28,Trp30,Leu31]hPYY(4-36) (Compound 3);
N{alpha-4}-(3-Methylbutanoyl)-N{Epsilon-7}-6-[[(4S)-4-carboxy-4-(17-carboxy-heptadecanoylamino)butanoyl]amino]hexanoyl-[Arg4,Lys7,Pro9,Gln18,Tyr28, Trp30, Leu31]hPYY(4-36) (Compound 4);
N{alpha-4}-(3-Methylbutanoyl)-N{Epsilon-7}-[2-[2-[2-[[2-[2-[2-[[(4S)-4-carboxy-4-[[(4S)-4-carboxy-4-(17-carboxyheptadecanoylamino)butanoyl]amino]butanoyl]amino]-ethoxy]ethoxy]-acetyl]amino]ethoxy]ethoxy]acetyl]-[Arg4,Lys7,Gln18,Tyr28,Trp30, Leu31]hPYY(4-36) (Compound 5);
N{alpha-4}-(3-Methylbutanoyl)-N{Epsilon-7}-[(4S)-4-carboxy-4-(15-carboxy-pentadecanoylamino) butanoyl]-[Arg4,Lys7,Gln18,Tyr28,Trp30,Leu31]hPYY(4-36) (Compound 6);
N{alpha-4}-(3-Methylbutanoyl)-N{Epsilon-7}-[(4S)-4-carboxy-4-(19-carboxy-nonadecanoylamino)butanoyl]-[Arg4,Lys7,Gln18,Tyr28,Trp30,Leu31]hPYY(4-36) (Compound 7);
N{alpha-4}-(3-Methylbutanoyl)-N{Epsilon-7}-[2-[2-[2-[[(4S)-4-carboxy-4-(17-carboxy-heptadecanoylamino) butanoyl]amino]ethoxy]ethoxy]acetyl]-[Arg4,Lys7, Gln18,Tyr28, Trp30,Leu31]hPYY(4-36) (Compound 8);
N{alpha-4}-(3-Methylbutanoyl)-N{Epsilon-7}-[(4S)-4-carboxy-4-(16-sulfohexadecanoyl-amino)butanoyl]-[Arg4,Lys7,Gln18,Tyr28,Trp30,Leu31]hPYY(4-36) (Compound 9);
N{alpha-4}-(3-Methylbutanoyl)-N{Epsilon-7}-6-[[(4S)-4-carboxy-4-(19-carboxy-nonadecanoylamino)butanoyl]amino]hexanoyl-[Arg4,Lys7,Gln18,Tyr28,Trp30, Leu31] hPYY(4-36) (Compound 10);
N{alpha-4}-(3-Methylbutanoyl)-N{Epsilon-7}-[(4S)-4-carboxy-4-[[(4S)-4-carboxy-4-(17-carboxyheptadecanoylamino)butanoyl]amino]butanoyl]-[Arg4,Lys7,Pro9, Gln18, Tyr28,Trp30,Leu31]hPYY(4-36) (Compound 11);
N{alpha-4}-(3-Methylbutanoyl)-N{Epsilon-7}-[(4S)-4-carboxy-4-[[(4S)-4-carboxy-4-(19-carboxynonadecanoylamino)butanoyl]amino]butanoyl]-[Arg4,Lys7,Pro9, Gln18, Tyr28,Trp30,Leu31]hPYY(4-36) (Compound 12);
N{alpha-4}-(3-Methylbutanoyl)-N{Epsilon-7}-[2-[2-[2-[[2-[2-[2-[[(4S)-4-carboxy-4-(17-carboxyheptadecanoylamino)butanoyl]amino]ethoxy]ethoxy]acetyl]amino]-ethoxy]ethoxy]acetyl]-[Arg4,Lys7,Ser9,Gln18,Tyr28, Trp30,Leu31]hPYY(4-36) (Compound 13);
N{alpha-4}-(3-Methylbutanoyl)-N{Epsilon-7}-[2-[2-[2-[[2-[2-[2-[[(4S)-4-carboxy-4-(17-carboxyheptadecanoylamino)butanoyl]amino]ethoxy]ethoxy]acetyl]amino]-ethoxy]ethoxy]acetyl]-[Arg4,Lys7,Thr9,Gln18,Tyr28, Trp30,Leu31]hPYY(4-36) (Compound 14);
N{alpha-4}-(3-Methylbutanoyl)-N{Epsilon-7}-[(4S)-4-carboxy-4-(17-carboxy-heptadecanoylamino)butanoyl]-[Arg4,Lys7,Thr13,Gln18,Tyr28,Trp30,Leu31]hPYY(4-36) (Compound 15);
N{alpha-4}-(3-Methylbutanoyl)-N{Epsilon-7}-[2-[2-[2-[[2-[2-[2-[[(4S)-4-carboxy-4-(17-carboxyheptadecanoylamino)butanoyl]amino]ethoxy]ethoxy]acetyl]amino]-ethoxy]ethoxy]acetyl]-[Arg4,Lys7,Thr13,Gln18,Tyr28, Trp30,Leu31]hPYY(4-36) (Compound 16);
N{alpha-4}-(3-Methylbutanoyl)-N{Epsilon-7}-[(4S)-4-carboxy-4-(17-carboxy-heptadecanoylamino)butanoyl]-[Arg4,Lys7,Gln18,Ala24,Tyr28,Trp30,Leu31]hPYY(4-36) (Compound 17);
N{alpha-4}-(3-Methylbutanoyl)-N{Epsilon-7}-[(4S)-4-carboxy-4-(17-carboxy-heptadecanoylamino)butanoyl]-[Arg4,Lys7,Gln18,Ile24,Tyr28,Trp30,Leu31]hPYY(4-36) (Compound 18);

N{alpha-4}-(3-Methylbutanoyl)-N{Epsilon-7}-6-[[(4S)-4-carboxy-4-(19-carboxy-nonadecanoylamino)butanoyl]amino]hexanoyl-[Arg4,Lys7,Gln18,Ile24,Tyr28,Trp30,Leu31]hPYY(4-36) (Compound 19);

N{alpha-4}-(3-Methylbutanoyl)-N{Epsilon-7}-6-[[(4S)-4-carboxy-4-(17-carboxy-heptadecanoylamino)butanoyl]amino]hexanoyl-[Arg4,Lys7,Gln18,Ile24, Tyr28,Trp30,Leu31]hPYY(4-36) (Compound 20);

N{alpha-4}-1-(3-Methylbutanoyl)-N{Epsilon-7}-[2-[2-[2-[[2-[2-[2-[[(4S)-4-carboxy-4-(17-carboxy heptadecanoylamino)butanoyl]amino]ethoxy]ethoxy]acetyl]amino]ethoxy]ethoxy]acetyl]-[Arg4,Lys7,Pro9,Gln18,Tyr28,Trp30,Leu31]hPYY(4-36) (Compound 21);

N{Alpha-4}-acetyl,N{Epsilon-7}-[(4S)-4-carboxy-4-(17-carboxyheptadecanoylamino)-butanoyl]-[Arg4,Lys7,Gln18,Ile24,Tyr28,Trp30,Leu31]hPYY(4-36) (Compound 22);

N{Epsilon-7}-[(4S)-4-carboxy-4-[[(4S)-4-carboxy-4-(17-carboxyheptadecanoylamino)-butanoyl]amino]butanoyl]-[Arg4,Lys7,Gln18,Ile22,Trp30,Leu31]hPYY(3-36) (Compound 23);

N{Epsilon-7}-[2-[2-[2-[[2-[2-[2-[[(4S)-4-carboxy-4-(17-carboxyheptadecanoylamino)-butanoyl]amino]ethoxy]ethoxy]acetyl]amino]ethoxy]ethoxy]acetyl]-[Arg4,Lys7,Gln18, Ile22,Trp30,Leu31]hPYY(3-36) (Compound 24);

N{alpha-4}-(3-Methylbutanoyl)-N{Epsilon-7}-[(4S)-4-carboxy-4-(17-carboxy-heptadecanoylamino)butanoyl]-[Arg4,Lys7,Gln18,Ile22,Trp30,Leu31]hPYY(4-36) (Compound 25);

N{alpha-4}-(3-Methylbutanoyl)-N{Epsilon-7}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Arg4,Lys7,Gln18,Ile22,Trp30,Leu31]hPYY(4-36) (Compound 26);

N{alpha-4}-(3-Methylbutanoyl)-N{Epsilon-7}-[(4S)-4-carboxy-4-(17-carboxy-heptadecanoylamino)butanoyl]-[Arg4,Lys7,Pro9,Gln18,Ile22,Trp30,Leu31]hPYY(4-36) (Compound 27);

N{alpha-4}-(3-Methylbutanoyl)-N{Epsilon-7}-[2-[2-[2-[[2-[2-[2-[[(4S)-4-carboxy-4-[[(4S)-4-carboxy-4-(17-carboxyheptadecanoylamino)butanoyl]amino]butanoyl]amino]-ethoxy]ethoxy]acetyl]amino]ethoxy]ethoxy]acetyl]-[Arg4,Lys7,Gln18,Ile22,Trp30, Leu31]hPYY(4-36) (Compound 28);

N{alpha-4}-(3-Methylbutanoyl)-N{Epsilon-7}-[(4S)-4-carboxy-4-[[(4S)-4-carboxy-4-(17-carboxyheptadecanoylamino)butanoyl]amino]butanoyl]-[Arg4,Lys7,Gln18,Ile22, Tyr28,Trp30,Leu31]hPYY(4-36) (Compound 29);

N{alpha-4}-(3-Methylbutanoyl)-N{Epsilon-7}-[2-[2-[2-[[2-[2-[2-[[(4S)-4-carboxy-4-[[(4S)-4-carboxy-4-(17-carboxyheptadecanoylamino)butanoyl]amino]butanoyl]amino]-ethoxy]ethoxy]acetyl]amino]ethoxy]ethoxy]acetyl]-[Arg4,Lys7,Gln18,Ile22,Tyr28, Trp30,Leu31]hPYY(4-36) (Compound 30);

N{alpha-4}-(3-Methylbutanoyl)-N{Epsilon-7}-[2-[2-[2-[[2-[2-[2-[[(4S)-4-carboxy-4-(17-carboxyheptadecanoylamino)butanoyl]amino]ethoxy]ethoxy]acetyl]-amino]ethoxy]ethoxy]acetyl]-[Arg4,Lys7,Gln18,Ile22,Tyr28,Trp30,Leu31]hPYY(4-36) (Compound 31);

N{alpha-4}-(3-Methylbutanoyl)-N{Epsilon-7}-6-[[(4S)-4-carboxy-4-(17-carboxy-heptadecanoylamino)butanoyl]amino]hexanoyl-[Arg4,Lys7,Gln18,Ile22,Tyr28, Trp30,Leu31]hPYY(4-36) (Compound 32);

N{alpha-4}-(3-Methylbutanoyl)-N{Epsilon-7}-[(4S)-4-carboxy-4-[[(4S)-4-carboxy-4-(19-carboxynonadecanoylamino)butanoyl]amino]butanoyl]-[Arg4,Lys7,Gln18,Ile22,Tyr28,Trp30,Leu31]hPYY(4-36) (Compound 33);

N{alpha-4}-(3-Methylbutanoyl)-N{Epsilon-7}-[(4S)-4-carboxy-4-(17-carboxy-heptadecanoylamino)butanoyl]-[Arg4,Lys7,Gln18,Ile22,Ala24,Tyr28,Trp30, Leu31]hPYY(4-36) (Compound 34);

N{alpha-4}-(3-Methylbutanoyl)-N{Epsilon-7}-[(4S)-4-carboxy-4-(17-carboxy-heptadecanoylamino)butanoyl]-[Arg4,Lys7,Gln18,Gln22,Tyr28,Trp30,Leu31]hPYY(4-36) (Compound 35);

N{alpha-4}-(3-Methylbutanoyl)-N{Epsilon-7}-[2-[2-[2-[[2-[2-[2-[[(4S)-4-carboxy-4-(17-carboxyheptadecanoylamino)butanoyl]amino]ethoxy]ethoxy]acetyl]-amino]ethoxy]ethoxy]acetyl]-[Arg4,Lys7,Gln18,Gln22,Tyr28,Trp30,Leu31]hPYY(4-36) (Compound 36);

N{alpha-4}-(3-Methylbutanoyl)-N{Epsilon-7}-[2-[2-[2-[[2-[2-[2-[[(4S)-4-carboxy-4-[[(4S)-4-carboxy-4-(17-carboxyheptadecanoylamino)butanoyl]amino]butanoyl]amino]-ethoxy]ethoxy]acetyl]amino]ethoxy]ethoxy]acetyl]-[Arg4,Lys7,Gln18,Gln22,Tyr28, Trp30,Leu31]hPYY(4-36) (Compound 37);

N{alpha-4}-(3-Methylbutanoyl)-N{Epsilon-7}-[2-[2-[2-[[2-[2-[2-[[(4S)-4-carboxy-4-(17-carboxyheptadecanoylamino)butanoyl]amino]ethoxy]ethoxy]acetyl]amino]-ethoxy]ethoxy]acetyl]-[Arg4,Lys7,Gln18,Val22,Tyr28,Trp30,Leu31]hPYY(4-36) (Compound 38);

N{alpha-4}-(3-Methylbutanoyl)-N{Epsilon-7}-[2-[2-[2-[[2-[2-[2-[[(4S)-4-carboxy-4-[[(4S)-4-carboxy-4-(17-carboxyheptadecanoylamino)butanoyl]amino]butanoyl]-amino]ethoxy]ethoxy]acetyl]amino]ethoxy]ethoxy]acetyl]-[Arg4,Lys7,Gln18,Val22, Tyr28,Trp30,Leu31]hPYY(4-36) (Compound 39);

N{alpha-4}-(3-Methylbutanoyl)-N{Epsilon-7}-[(4S)-4-carboxy-4-(17-carboxy-heptadecanoylamino)butanoyl]-[Arg4,Lys7,Gln18,Val22,Tyr28,Trp30,Leu31]hPYY(4-36) (Compound 40);

N{alpha-4}-1-(3-Methylbutanoyl)-(N{Epsilon-7}-[(4S)-4-carboxy-4-[[(4S)-4-carboxy-4-(17-carboxy-heptadecanoylamino)butanoyl]amino]butanoyl]-[Arg4,Lys7, Gln18,Val22, Tyr28,Trp30,Leu31]hPYY(4-36) (Compound 41);

N{alpha-4}-(3-Methylbutanoyl)-N{Epsilon-7}-[(4S)-4-carboxy-4-(17-carboxy-heptadecanoylamino)butanoyl]-[Arg4,Lys7,Thr9,Gln18,Tyr28,Trp30,Leu31]hPYY(4-36) (Compound 42);

N{alpha-4}-(3-Methylbutanoyl)-N{Epsilon-7}-[(4S)-4-carboxy-4-(17-carboxy-heptadecanoylamino)butanoyl]-[Arg4,Lys7,Thr9,Gln18,Gln22,Tyr28,Trp30,Leu31]hPYY(4-36) (Compound 43);

N{alpha-4}-(3-Methylbutanoyl)-N{Epsilon-7}-[(4S)-4-carboxy-4-(17-carboxy-heptadecanoylamino)butanoyl]-[Arg4,Lys7,Thr9,Gln18,Val22,Tyr28,Trp30, Leu31]hPYY(4-36) (Compound 44);

N{alpha-4}-(3-Methylbutanoyl)-N{Epsilon-7}-[(4S)-4-carboxy-4-(17-carboxy-heptadecanoylamino)butanoyl]-[Arg4,Lys7,Thr13,Gln18,Gln22,Tyr28, Trp30,Leu31]hPYY(4-36) (Compound 45);

N{alpha-4}-(3-Methylbutanoyl)-N{Epsilon-7}-[2-[2-[2-[[2-[2-[2-[[(4S)-4-carboxy-4-(17-carboxyheptadecanoylamino)butanoyl]amino]ethoxy]ethoxy]acetyl]-amino]-ethoxy]ethoxy]acetyl]-[Arg4,Lys7,Thr13,Gln18,Val22,Tyr28,Trp30,Leu31]hPYY(4-36) (Compound 46);

N{alpha-4}-(3-Methylbutanoyl)-N{Epsilon-7}-[(4S)-4-carboxy-4-(17-carboxy-heptadecanoylamino)butanoyl]-[Arg4,Lys7,Thr13,Gln18,Val22,Tyr28, Trp30,Leu31]hPYY(4-36) (Compound 47);

N{alpha-4}-(3-Methylbutanoyl)-N{Epsilon-7}-[(4S)-4-carboxy-4-(19-carboxy-nonadecanoylamino)butanoyl]-[Arg4,Lys7,Gln18,Tyr28,Trp30,Leu31]hPYY(4-36) (Compound 48);

N{alpha-4}-(3-Methylbutanoyl)-N{Epsilon-7}-[(4S)-4-carboxy-4-(17-carboxy-heptadecanoylamino)butanoyl]-[Arg4,Lys7,Gln18,Ile22,Tyr28,Trp30, Leu31]hPYY(4-36) (Compound 49);

N{alpha-4}-(3-Methylbutanoyl)-N{Epsilon-10}-[(4S)-4-carboxy-4-[[2-[2-[2-[[(4S)-4-carboxy-4-(17-carboxyheptadecanoylamino)butanoyl]amino]ethoxy]ethoxy]-acetyl]amino]butanoyl]-[Arg4,Lys10,Gln18,Glu22,Tyr28,Trp30,Leu31]-PYY(4-36) (Compound 50);

N{alpha-4}-(3-Methylbutanoyl)-N{Epsilon-10}-[2-[2-[2-[[2-[2-[2-[[(4S)-4-carboxy-4-(17-carboxyheptadecanoylamino)butanoyl]amino]ethoxy]ethoxy]acetyl]-amino]ethoxy]ethoxy]acetyl]-[Arg4,Lys10,Gln18,Glu22,Tyr28,Trp30,Leu31]-PYY(4-36) (Compound 51);

N{alpha-4}-(3-Methylbutanoyl)-N{Epsilon-10}-[2-[2-[2-[[2-[2-[2-[[(4S)-4-carboxy-4-(17-carboxyheptadecanoylamino)butanoyl]amino]ethoxy]ethoxy]acetyl]amino]-ethoxy]ethoxy]acetyl]-[Arg4,Lys10,Gln18,Glu23,Tyr28,Trp30,Leu31]-PYY(4-36) (Compound 52);

N{alpha-4}-(3-Methylbutanoyl)-N{Epsilon-10}-[(4S)-4-carboxy-4-[[2-[2-[2-[[(4S)-4-carboxy-4-(17-carboxyheptadecanoylamino)butanoyl]amino]ethoxy]ethoxy]-acetyl]amino]butanoyl]-[Arg4,Lys10,Gln18,Glu23,Tyr28,Trp30,Leu31]-PYY(4-36) (Compound 53);

N{alpha-4}-(3-Methylbutanoyl)-N{Epsilon-10}-[(4S)-4-carboxy-4-[[2-[2-[2-[[(4S)-4-carboxy-4-(17-carboxyheptadecanoylamino)butanoyl]amino]ethoxy]ethoxy]-acetyl]amino]butanoyl]-[Arg4,Pro9,Lys10,Gln18,Glu22,Tyr28,Trp30,Leu31]-PYY(4-36) (Compound 54);

N{alpha-4}-(3-Methylbutanoyl)-N{Epsilon-7}-[(4S)-4-carboxy-4-(16-sulfohexadecanoylamino)butanoyl]-[Arg4,Lys7,Gln18,Tyr28,Trp30,Leu31]-PYY(4-36) (Compound 55);

N{alpha-4}-(3-Methylbutanoyl)-N{Epsilon-10}-[(4S)-4-carboxy-4-[[2-[2-[2-[[(4S)-4-carboxy-4-(17-carboxyheptadecanoylamino)butanoyl]amino]ethoxy]ethoxy]-acetyl]amino]butanoyl]-[Arg4,Pro9,Lys10,Gln18,Tyr28,Trp30,Leu31]-PYY(4-36) (Compound 56);

N{alpha-4}-(3-Methylbutanoyl)-N{Epsilon-7}-[2-[2-[2-[[(4S)-4-carboxy-4-(17-carboxyheptadecanoylamino)butanoyl]amino]ethoxy]ethoxy]acetyl]-[Arg4,Lys7,Gln18,Val22,Tyr28,Trp30,Leu31]-PYY(4-36) (Compound 57);

N{alpha-4}-(3-Methylbutanoyl)-N{Epsilon-7}-[2-[2-[2-[[(4S)-4-carboxy-4-(15-carboxypentadecanoylamino)butanoyl]amino]ethoxy]ethoxy]acetyl]-[Arg4,Lys7,Gln18,Tyr28,Trp30,Leu31]-PYY(4-36) (Compound 58);

N{alpha-4}-(3-Methylbutanoyl)-N{Epsilon-10}-[(4S)-4-carboxy-4-[[2-[2-[2-[[(4S)-4-carboxy-4-(17-carboxyheptadecanoylamino)butanoyl]amino]ethoxy]ethoxy]-acetyl]amino]butanoyl]-[Arg4,Lys10,Gln18,Tyr28,Trp30,Leu31]-PYY(4-36) (Compound 59);

N{alpha-4}-(3-Methylbutanoyl)-N{Epsilon-7}-[2-[2-[2-[[(4S)-4-carboxy-4-(17-carboxyheptadecanoylamino)butanoyl]amino]ethoxy]ethoxy]acetyl]-[Arg4,Lys7,Gln18,Ala24,Tyr28,Trp30,Leu31]-PYY(4-36) (Compound 60);

N{alpha-4}-(3-Methylbutanoyl)-N{Epsilon-7}-[2-[2-[2-[[2-[2-[2-[[(4S)-4-carboxy-4-(15-carboxypentadecanoylamino)butanoyl]amino]ethoxy]ethoxy]acetyl]-amino]ethoxy]ethoxy]acetyl]-[Arg4,Lys7,Pro9,Gln18,Tyr28,Trp30,Leu31]-PYY-(4-36) (Compound 61);

N{alpha-4}-(3-Methylbutanoyl)-N{Epsilon-7}-[2-[2-[2-[[(4S)-4-carboxy-4-(13-carboxytridecanoylamino)butanoyl]amino]ethoxy]ethoxy]acetyl]-[Arg4,Lys7,Gln18,Tyr28,Trp30,Leu31]-PYY(4-36) (Compound 62);

N{alpha-4}-(3-Methylbutanoyl)-N{Epsilon-7}-[2-[2-[2-[[2-[2-[2-[[(4S)-4-carboxy-4-(15-carboxypentadecanoylamino)butanoyl]amino]ethoxy]ethoxy]acetyl]-amino]ethoxy]ethoxy]acetyl]-[Arg4,Lys7,Gln18,Tyr28,Trp30,Leu31]-PYY(3-36) (Compound 63);

N{alpha-4}-(3-Methylbutanoyl)-N{Epsilon-7}-[2-[2-[2-[[2-[2-[2-[[2-[2-[2-[[(4S)-4-carboxy-4-(17-carboxyheptadecanoylamino)butanoyl]amino]-ethoxy]ethoxy]acetyl]amino]ethoxy]ethoxy]acetyl]amino]ethoxy]ethoxy]acetyl]amino]ethoxy]ethoxy]acetyl]-[Arg4,Lys7,Pro9,Gln18,Tyr28,Trp30,Leu31]-PYY(4-36) (Compound 65);

N{alpha-4}-(3-Methylbutanoyl)-N{Epsilon-7}-[2-[2-[2-[[2-[2-[2-[[(4S)-4-carboxy-4-(16-sulfohexadecanoylamino)butanoyl]amino]ethoxy]ethoxy]acetyl]-amino]ethoxy]ethoxy]acetyl]-[Arg4,Lys7,Pro9,Gln18,Tyr28,Trp30,Leu31]-PYY(4-36) (Compound 66);

N{alpha-4}-(3-Methylbutanoyl)-N{Epsilon-7}-[2-[2-[2-[[(4S)-4-carboxy-4-(16-sulfohexadecanoylamino)butanoyl]amino]ethoxy]ethoxy]acetyl]-[Arg4,Lys7,Gln18,Tyr28,Trp30,Leu31]-PYY(4-36) (Compound 67);

N{alpha-4}-(3-Methylbutanoyl)-N{Epsilon-7}-[2-[2-[2-[[(4S)-4-carboxy-4-(16-sulfohexadecanoylamino)butanoyl]amino]ethoxy]ethoxy]acetyl]-amino]ethoxy]ethoxy]acetyl]-[Arg4,Lys7,Gln18,Tyr28,Trp30,Leu31]-PYY(4-36) (Compound 68);

N{alpha-4}-(3-Methylbutanoyl)-N{Epsilon-10}-[(4S)-4-carboxy-4-[[2-[2-[2-[[(4S)-4-carboxy-4-(16-sulfohexadecanoylamino)butanoyl]amino]ethoxy]-ethoxy]acetyl]amino]butanoyl]-[Arg4,Pro9,Lys10,Gln18,Tyr28,Trp30,Leu31]-PYY-(4-36) (Compound 69);

N{alpha-4}-(3-Methylbutanoyl)-N{Epsilon-7}-[(4S)-4-carboxy-4-(13-carboxytridecanoylamino)butanoyl]-[Arg4, Lys7, Pro9,Gln18,Tyr28,Trp30,Leu31]-PYY-(4-36) (Compound 70); and N{alpha-4}-(3-Methylbutanoyl)-N{Epsilon-7}-[2-[2-[2-[[(4S)-4-carboxy-4-(13-carboxytridecanoylamino)butanoyl]amino]ethoxy]ethoxy]acetyl]-[Arg4,Lys7,Pro9,Gln18,Tyr28,Trp30,Leu31]-PYY-(4-36) (Compound 71).

84. A PYY compound according to any one of the preceding embodiments selected from the following:

N{alpha-4}-(3-Methylbutanoyl)-N{Epsilon-7}-[(4S)-4-carboxy-4-(17-carboxy-heptadecanoylamino)butanoyl]-[Arg4,Lys7,Gln18,Tyr28,Trp30,Leu31]hPYY(4-36) (Compound 2);

N{alpha-4}-(3-Methylbutanoyl)-N{Epsilon-7}-[2-[2-[2-[[2-[2-[2-[[(4S)-4-carboxy-4-(17-carboxyheptadecanoylamino)butanoyl]amino]ethoxy]ethoxy]acetyl]amino]-ethoxy]ethoxy]acetyl]-[Arg4,Lys7,Gln18,Tyr28,Trp30,Leu31]hPYY(4-36) (Compound 3);

N{alpha-4}-(3-Methylbutanoyl)-N{Epsilon-7}-6-[[(4S)-4-carboxy-4-(17-carboxy-heptadecanoylamino)butanoyl]amino]hexanoyl-[Arg4,Lys7,Pro9,Gln18,Tyr28, Trp30,Leu31]hPYY(4-36) (Compound 4);

N{alpha-4}-(3-Methylbutanoyl)-N{Epsilon-7}-[2-[2-[2-[[(4S)-4-carboxy-4-(17-carboxy-heptadecanoylamino)butanoyl]amino]ethoxy]ethoxy]acetyl]-[Arg4,Lys7,Gln18,Tyr28, Trp30,Leu31]hPYY(4-36) (Compound 8);

N{alpha-4}-(3-Methylbutanoyl)-N{Epsilon-7}-[2-[2-[2-[[2-[2-[2-[[(4S)-4-carboxy-4-(17-carboxyheptadecanoylamino)butanoyl]amino]ethoxy]ethoxy]acetyl]amino]-ethoxy]ethoxy]acetyl]-[Arg4,Lys7,Thr9,Gln18,Tyr28,Trp30,Leu31]hPYY(4-36) (Compound 14);

N{alpha-4}-(3-Methylbutanoyl)-N{Epsilon-7}-[2-[2-[2-[[2-[2-[2-[[(4S)-4-carboxy-4-(17-carboxyheptadecanoylamino)butanoyl]amino]ethoxy]ethoxy]acetyl]amino]-ethoxy]ethoxy]acetyl]-[Arg4,Lys7,Thr13,Gln18,Tyr28, Trp30,Leu31]hPYY(4-36) (Compound 16);

N{alpha-4}-(3-Methylbutanoyl)-N{Epsilon-7}-6-[[(4S)-4-carboxy-4-(19-carboxy-nonadecanoylamino) butanoyl] amino]hexanoyl-[Arg4,Lys7,Gln18,Ile24,Tyr28,Trp30, Leu31]hPYY(4-36) (Compound 19);

N{alpha-4}-1-(3-Methylbutanoyl)-N{Epsilon-7}-[2-[2-[2-[[2-[2-[2-[[(4S)-4-carboxy-4-(17-carboxy-heptadecanoylamino)butanoyl]amino]ethoxy]ethoxy]acetyl]amino] ethoxy]ethoxy]acetyl]-[Arg4,Lys7,Pro9,Gln18,Tyr28, Trp30,Leu31]hPYY(4-36) (Compound 21);

N{Alpha-4}-acetyl,N{Epsilon-7}-[(4S)-4-carboxy-4-(17-carboxyheptadecanoylamino)-butanoyl]-[Arg4,Lys7, Gln18,Ile24,Tyr28,Trp30,Leu31]hPYY(4-36) (Compound 22);

N{alpha-4}-(3-Methylbutanoyl)-N{Epsilon-7}-6-[[(4S)-4-carboxy-4-(17-carboxy-heptadecanoylamino)butanoyl] amino]hexanoyl-[Arg4,Lys7,Gln18,Ile22,Tyr28, Trp30, Leu31]hPYY(4-36) (Compound 32);

N{alpha-4}-(3-Methylbutanoyl)-N{Epsilon-7}-[2-[2-[2-[[2-[2-[2-[[(4S)-4-carboxy-4-(17-carboxyheptadecanoylamino)butanoyl]amino]ethoxy]ethoxy]acetyl]-amino] ethoxy]ethoxy]acetyl]-[Arg4,Lys7,Gln18,Gln22,Tyr28, Trp30,Leu31]hPYY(4-36) (Compound 36);

N{alpha-4}-(3-Methylbutanoyl)-N{Epsilon-7}-[2-[2-[2-[[2-[2-[2-[[(4S)-4-carboxy-4-(17-carboxyheptadecanoylamino)butanoyl]amino]ethoxy]ethoxy]acetyl]amino]-ethoxy]ethoxy]acetyl]-[Arg4,Lys7,Gln18,Val22,Tyr28, Trp30,Leu31]hPYY(4-36) (Compound 38);

N{alpha-4}-(3-Methylbutanoyl)-N{Epsilon-7}-[(4S)-4-carboxy-4-(17-carboxy-heptadecanoylamino)butanoyl]-[Arg4,Lys7,Gln18,Val22,Tyr28,Trp30,Leu31]hPYY(4-36) (Compound 40);

N{alpha-4}-1-(3-Methylbutanoyl)-(N{Epsilon-7}-[(4S)-4-carboxy-4-[[(4S)-4-carboxy-4-(17-carboxy-heptadecanoylamino)butanoyl]amino]butanoyl]-[Arg4,Lys7, Gln18,Val22, Tyr28,Trp30,Leu31]hPYY(4-36) (Compound 41); and N{alpha-4}-(3-Methylbutanoyl)-N{Epsilon-7}-[(4S)-4-carboxy-4-(19-carboxy-nonadecanoylamino)butanoyl]-[Arg4,Lys7,Gln18,Tyr28,Trp30,Leu31]hPYY(4-36) (Compound 48).

85. A PYY compound according to any one of the preceding embodiments selected from the following:

N{alpha-4}-(3-Methylbutanoyl)-N{Epsilon-7}-6-[[(4S)-4-carboxy-4-(17-carboxy-heptadecanoylamino)butanoyl] amino]hexanoyl-[Arg4,Lys7,Pro9,Gln18,Tyr28, Trp30, Leu31]hPYY(4-36) (Compound 4);

N{alpha-4}-(3-Methylbutanoyl)-N{Epsilon-7}-[2-[2-[2-[[(4S)-4-carboxy-4-(17-carboxyheptadecanoylamino) butanoyl]amino]ethoxy]ethoxy]acetyl]-[Arg4,Lys7, Gln18,Tyr28, Trp30,Leu31]hPYY(4-36) (Compound 8);

N{alpha-4}-N{Epsilon-7}-[2-[2-[2-[[2-[2-[2-[[(4S)-4-carboxy-4-(17-carboxy-heptadecanoylamino)butanoyl] amino]ethoxy]ethoxy]acetyl]amino]ethoxy]ethoxy] acetyl]-[Arg4,Lys7,Pro9,Gln18,Tyr28,Trp30,Leu31] hPYY(4-36) (Compound 21);

N{alpha-4}-(3-Methylbutanoyl)-N{Epsilon-7}-6-[[(4S)-4-carboxy-4-(17-carboxy-heptadecanoylamino)butanoyl] amino]hexanoyl-[Arg4,Lys7,Gln18,Ile22,Tyr28, Trp30, Leu31]hPYY(4-36) (Compound 32); and N{alpha-4}-(3-Methylbutanoyl)-N{Epsilon-7}-[(4S)-4-carboxy-4-(17-carboxy-heptadecanoylamino)butanoyl]-[Arg4,Lys7,Gln18,Val22,Tyr28,Trp30,Leu31]hPYY(4-36) (Compound 40).

86. A PYY compound according to embodiment 1, wherein the PYY compound is
N{alpha-4}-(3-Methylbutanoyl)-N{Epsilon-7}-[(4S)-4-carboxy-4-(17-carboxy-heptadecanoylamino)butanoyl]-[Arg4,Lys7,Gln18,Tyr28,Trp30,Leu31]hPYY(4-36) (Compound 2).

87. A PYY compound according to embodiment 1, wherein the PYY compound is
N{alpha-4}-(3-Methylbutanoyl)-N{Epsilon-7}-[2-[2-[2-[[2-[2-[2-[[(4S)-4-carboxy-4-(17-carboxyheptadecanoylamino)butanoyl]amino]ethoxy]ethoxy]acetyl]amino]-ethoxy]ethoxy]acetyl]-[Arg4,Lys7,Gln18,Tyr28,Trp30, Leu31]hPYY(4-36) (Compound 3).

88. A PYY compound according to embodiment 1, wherein the PYY compound is
N{alpha-4}-(3-Methylbutanoyl)-N{Epsilon-7}-6-[[(4S)-4-carboxy-4-(17-carboxy-heptadecanoylamino)butanoyl] amino]hexanoyl-[Arg4,Lys7,Pro9,Gln18,Tyr28, Trp30, Leu31]hPYY(4-36) (Compound 4).

89. A PYY compound according to embodiment 1, wherein the PYY compound is
N{alpha-4}-(3-Methylbutanoyl)-N{Epsilon-7}-[2-[2-[2-[[(4S)-4-carboxy-4-(17-carboxyheptadecanoylamino) butanoyl]amino]ethoxy]ethoxy]acetyl]-[Arg4,Lys7, Gln18,Tyr28, Trp30,Leu31]hPYY(4-36) (Compound 8).

90. A PYY compound according to embodiment 1, wherein the PYY compound is
N{alpha-4}-(3-Methylbutanoyl)-N{Epsilon-7}-[2-[2-[2-[[2-[2-[2-[[(4S)-4-carboxy-4-(17-carboxyheptadecanoylamino)butanoyl]amino]ethoxy]ethoxy]acetyl]amino]-ethoxy]ethoxy]acetyl]-[Arg4,Lys7,Thr9,Gln18,Tyr28, Trp30,Leu31]hPYY(4-36) (Compound 14).

91. A PYY compound according to embodiment 1, wherein the PYY compound is
N{alpha-4}-(3-Methylbutanoyl)-N{Epsilon-7}-[2-[2-[2-[[2-[2-[2-[[(4S)-4-carboxy-4-(17-carboxyheptadecanoylamino)butanoyl]amino]ethoxy]ethoxy]acetyl]amino]-ethoxy]ethoxy]acetyl]-[Arg4,Lys7,Thr13,Gln18,Tyr28, Trp30,Leu31]hPYY(4-36) (Compound 16).

92. A PYY compound according to embodiment 1, wherein the PYY compound is
N{alpha-4}-(3-Methylbutanoyl)-N{Epsilon-7}-6-[[(4S)-4-carboxy-4-(19-carboxy-nonadecanoylamino)butanoyl] amino]hexanoyl-[Arg4,Lys7,Gln18,Ile24,Tyr28,Trp30, Leu31]hPYY(4-36) (Compound 19).

93. A PYY compound according to embodiment 1, wherein the PYY compound is
N{alpha-4}-N{Epsilon-7}-[2-[2-[2-[[2-[2-[2-[[(4S)-4-carboxy-4-(17-carboxy-heptadecanoylamino)butanoyl] amino]ethoxy]ethoxy]acetyl]amino]ethoxy]ethoxy] acetyl]-[Arg4,Lys7,Pro9,Gln18,Tyr28,Trp30,Leu31] hPYY(4-36) (Compound 21).

94. A PYY compound according to embodiment 1, wherein the PYY compound is
N{Alpha-4}-acetyl,N{Epsilon-7}-[(4S)-4-carboxy-4-(17-carboxyheptadecanoylamino)-butanoyl]-[Arg4,Lys7, Gln18,Ile24,Tyr28,Trp30,Leu31]hPYY(4-36) (Compound 22).

95. A PYY compound according to embodiment 1, wherein the PYY compound is
N{alpha-4}-(3-Methylbutanoyl)-N{Epsilon-7}-6-[[(4S)-4-carboxy-4-(17-carboxy-heptadecanoylamino)butanoyl] amino]hexanoyl-[Arg4,Lys7,Gln18,Ile22,Tyr28, Trp30, Leu31]hPYY(4-36) (Compound 32).

96. A PYY compound according to embodiment 1, wherein the PYY compound is

N{alpha-4}-(3-Methylbutanoyl)-N{Epsilon-7}-[2-[2-[2-[[2-[2-[2-[[(4S)-4-carboxy-4-(17-carboxyheptadecanoylamino)butanoyl]amino]ethoxy]ethoxy]acetyl]-amino]ethoxy]ethoxy]acetyl]-[Arg4,Lys7,Gln18,Gln22,Tyr28,Trp30,Leu31]hPYY(4-36) (Compound 36).

97. A PYY compound according to embodiment 1, wherein the PYY compound is
N{alpha-4}-(3-Methylbutanoyl)-N{Epsilon-7}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Arg4,Lys7,Gln18,Val22,Tyr28,Trp30,Leu31]hPYY(4-36) (Compound 38).

98. A PYY compound according to embodiment 1, wherein the PYY compound is
N{alpha-4}-(3-Methylbutanoyl)-N{Epsilon-7}-[(4S)-4-carboxy-4-(17-carboxy-heptadecanoylamino)butanoyl]-[Arg4,Lys7,Gln18,Val22,Tyr28,Trp30,Leu31]hPYY(4-36) (Compound 40).

99. A PYY compound according to embodiment 1, wherein the PYY compound is
N{alpha-4}-1-(3-Methylbutanoyl)-(N{Epsilon-7}-[(4S)-4-carboxy-4-[[(4S)-4-carboxy-4-(17-carboxy-heptadecanoylamino)butanoyl]amino]butanoyl]-[Arg4,Lys7,Gln18,Val22,Tyr28,Trp30,Leu31]hPYY(4-36) (Compound 41).

100. A PYY compound according to embodiment 1, wherein the PYY compound is
N{alpha-4}-(3-Methylbutanoyl)-N{Epsilon-7}-[(4S)-4-carboxy-4-(19-carboxy-nonadecanoylamino)butanoyl]-[Arg4,Lys7,Gln18,Tyr28,Trp30,Leu31]hPYY(4-36) (Compound 48).

101. A PYY compound having a maximum of 10 amino acid changes as compared to hPYY(3-36) (SEQ ID NO:2), wherein the PYY compound comprises
i) tryptophan at the position corresponding to position 30 of hPYY(1-36) (SEQ ID NO:1);
ii) leucine at the position corresponding to position 31 of hPYY(1-36) (SEQ ID NO:1);
iii) tyrosine at the position corresponding to position 28 of hPYY(1-36) (SEQ ID NO:1) and/or isoleucine at the position corresponding to position 22 of hPYY(1-36) (SEQ ID NO:1); or a pharmaceutically acceptable salt, amide, or ester of said PYY compound.

102. A PYY compound having a maximum of 10 amino acid changes as compared to hPYY(3-36) (SEQ ID NO:2), wherein the PYY compound comprises
i) tryptophan at the position corresponding to position 30 of hPYY(1-36) (SEQ ID NO:1);
ii) leucine at the position corresponding to position 31 of hPYY(1-36) (SEQ ID NO:1);
iii) tyrosine at the position corresponding to position 28 of hPYY(1-36) (SEQ ID NO:1); or a pharmaceutically acceptable salt, amide, or ester of said PYY compound.

103. A PYY compound having a maximum of 10 amino acid modifications as compared to hPYY(3-36) (SEQ ID NO:2), wherein the PYY compound comprises
i) tryptophan at the position corresponding to position 30 of hPYY(1-36) (SEQ ID NO:1);
ii) leucine at the position corresponding to position 31 of hPYY(1-36) (SEQ ID NO:1);
iii) tyrosine at the position corresponding to position 28 of hPYY(1-36) (SEQ ID NO:1);
iv) isoleucine at the position corresponding to position 22 of hPYY(1-36) (SEQ ID NO:1);
or a pharmaceutically acceptable salt, amide, or ester of said PYY compound.

104. A PYY compound according to any one of the embodiments 101-103, comprising lysine at the position corresponding to position 7 or 10 of hPYY(1-36) (SEQ ID NO:1).

105. A PYY compound according to any of the embodiments 101-103, wherein the PYY compound comprises arginine at the position corresponding to position 4 of hPYY(1-36) (SEQ ID NO:1).

106. A PYY compound according to any of the embodiments 101-103, wherein the PYY compound comprises proline, serine, or threonine at the position corresponding to position 9 of hPYY(1-36) (SEQ ID NO:1).

107. A PYY compound according to any of the embodiments 101-103, wherein the PYY compound comprises threonine at the position corresponding to position 13 of hPYY(1-36) (SEQ ID NO:1).

108. A PYY compound according to any of the embodiments 101-103, wherein the PYY compound comprises glutamine at the position corresponding to position 18 of hPYY(1-36) (SEQ ID NO:1).

109. A PYY compound according to any of the embodiments 101-103, wherein the PYY compound comprises glutamic acid or valine at the position corresponding to position 22 of hPYY(1-36) (SEQ ID NO:1).

110. A PYY compound according to any of the embodiments 101-103, wherein the PYY compound comprises glutamic acid at the position corresponding to position 23 of hPYY(1-36) (SEQ ID NO:1)

111. A PYY compound according to any of the embodiments 101-103, wherein the PYY compound comprises alanine or isoleucine at the position corresponding to position 24 of hPYY(1-36) (SEQ ID NO:1).

112. A PYY compound according to any of the embodiments 101-103, wherein the positions corresponding to positions 1 and 2 of hPYY(1-36) (SEQ ID NO:1) are absent.

113. A PYY compound according to any of the embodiments 101-103, wherein the positions corresponding to positions 1-3 of hPYY(1-36) (SEQ ID NO:1) are absent.

114. A PYY compound according to any of the embodiments 101-103, wherein the positions corresponding to positions 1-3 of hPYY(1-36) (SEQ ID NO:1) are absent, and wherein the PYY compound further comprises an N-terminal substituent, wherein the N-terminal substituent is an alkoxy group comprising up to 12 carbon atoms.

115. A PYY compound according to any of the embodiments 101-103, wherein the N-terminal substituent is an alkoxy group comprising up to 10 carbon atoms.

116. A PYY compound according to any of the embodiments 101-103, wherein the N-terminal substituent is an alkoxy group comprising up to 8 carbon atoms.

117. A PYY compound according to any of the embodiments 101-103, wherein the N-terminal substituent is an alkoxy group comprising up to 6 carbon atoms.

118. A PYY compound according to any of the embodiments 101-103, wherein the N-terminal substituent is 3-methylbutanoyl.

119. A PYY compound according any of the embodiments 101-103, wherein the N-terminal substituent is acetyl.

120. A PYY compound according to any of the embodiments 101-103, wherein the PYY compound has a maximum of 9 amino acid modifications as compared to hPYY(3-36) (SEQ ID NO:2).

121. A PYY compound according to any of the embodiments 101-103, wherein the PYY compound has a maximum of 8 amino acid modifications as compared to hPYY(3-36) (SEQ ID NO:2).

122. A PYY compound according to any of the embodiments 101-103, wherein the PYY compound has a maximum of 7 amino acid modifications as compared to hPYY(3-36) (SEQ ID NO:2).
123. A PYY compound according to any of the embodiments 101-103, wherein the PYY compound has a maximum of 6 amino acid modifications as compared to hPYY(3-36) (SEQ ID NO:2).
124. A PYY compound according to any of the embodiments 101-103, wherein the PYY compound has a maximum of 5 amino acid modifications as compared to hPYY(3-36) (SEQ ID NO:2).
125. A PYY compound according to any of the embodiments 101-103, wherein the PYY compound has a minimum of 2 amino acid modifications as compared to hPYY(3-36) (SEQ ID NO:2).
126. A PYY compound according to any of the embodiments 101-103, wherein the PYY compound has a minimum of 3 amino acid modifications as compared to hPYY(3-36) (SEQ ID NO:2).
127. A PYY compound according to any of the embodiments 101-103, wherein the PYY compound has a minimum of 4 amino acid modifications as compared to hPYY(3-36) (SEQ ID NO:2).
128. A PYY compound according to any of the embodiments 101-103, wherein the PYY compound has a minimum of 5 amino acid modifications as compared to hPYY(3-36) (SEQ ID NO:2).
129. A PYY compound according to any of the embodiments 101-103, wherein the PYY compound has a minimum of 6 amino acid modifications as compared to hPYY(3-36) (SEQ ID NO:2).
130. A PYY compound according any of the embodiments 101-103, wherein the PYY compound has a minimum of 7 amino acid modifications as compared to hPYY(3-36) (SEQ ID NO:2).
131. A PYY compound according to any of the embodiments 101-103, wherein the PYY compound has a minimum of 8 amino acid modifications as compared to hPYY(3-36) (SEQ ID NO:2).
132. A PYY compound according to any of the embodiments 101-103, wherein the PYY compound has in the range of 4 to 10 amino acid modifications as compared to hPYY(3-36) (SEQ ID NO:2).
133. A PYY compound according to any of the embodiments 101-103, wherein the PYY compound has in the range of 6 to 8 amino acid modifications as compared to hPYY(3-36) (SEQ ID NO:2).
134. A PYY compound according to any of the embodiments 101-103, wherein the PYY compound has in the range of 4 to 6 amino acid modifications as compared to hPYY(3-36) (SEQ ID NO:2).
135. A PYY compound according to any of the embodiments 101-103, wherein the PYY compound has 4 amino acid modifications as compared to hPYY(3-36) (SEQ ID NO:2).
136. A PYY compound according to any of the embodiments 101-103, wherein the PYY compound has 5 amino acid modifications as compared to hPYY(3-36) (SEQ ID NO:2).
137. A PYY compound according to any of the embodiments 101-103, wherein the PYY compound has 6 amino acid modifications as compared to hPYY(3-36) (SEQ ID NO:2).
138. A PYY compound according to any of the embodiments 101-103, wherein the PYY compound has 7 amino acid modifications as compared to hPYY(3-36) (SEQ ID NO:2).
139. A PYY compound according to any of the embodiments 101-103, wherein the PYY compound has 8 amino acid modifications as compared to hPYY(3-36) (SEQ ID NO:2).
140. A PYY compound according to any of the embodiments 101-103, wherein the PYY compound has 9 amino acid modifications as compared to hPYY(3-36) (SEQ ID NO:2).
141. A PYY compound according to any of the embodiments 101-103, selected from the following:
N{alpha-4}-(3-Methylbutanoyl)-[Arg4,Gln18,Tyr28,Trp30, Leu31]-PYY(4-36) (Compound 64); and
N{alpha-4}-(3-Methylbutanoyl)-[Arg4,Gln18,Val22,Tyr28, Trp30,Leu31]-PYY-(4-36) (Compound 72).
142. A PYY compound according to any of the embodiments 101-103, wherein the PYY compound is N{alpha-4}-(3-Methylbutanoyl)-[Arg4,Gln18,Tyr28,Trp30,Leu31]-PYY (4-36) (Compound 64).
143. A PYY compound according to any one of embodiments 101-103, wherein the PYY compound is N{alpha-4}-(3-Methylbutanoyl)-[Arg4,Gln18,Val22,Tyr28,Trp30, Leu31]-PYY-(4-36) (Compound 72).
144. A PYY compound according to any one of the preceding embodiments which is a human Y2 receptor agonist.
145. A PYY compound according to any one of the preceding embodiments which is a full human Y2 receptor agonist.
146. A PYY compound according to any one of the preceding embodiments which is a selective human Y2 receptor agonist.
147. A PYY compound according to any one of the preceding embodiments which is a selective full human Y2 receptor agonist.
148. A PYY compound according to any one of the preceding embodiments which is capable of activating the human Y2 receptor.
149. A PYY compound according to any one of the preceding embodiments which is capable of activating the human Y2 receptor in an assay with whole cells expressing the human Y2 receptor.
150. A PYY compound according to any one of the preceding embodiments which is capable of activating the human Y2 receptor in the Actone functional potency assay of Example 2.
151. A PYY compound according to any one of the preceding embodiments which is capable of binding to the human Y2 receptor.
152. A PYY compound according to any one of the preceding embodiments which is capable of binding to the human Y2 receptor, wherein the binding to the human Y2 receptor is measured in a competitive binding assay, such as the assay of Example 3.
153. A PYY compound according to any one of the preceding embodiments which has improved pharmacokinetic properties.
154. A PYY compound according to any one of the preceding embodiments which has an increased half-life and/or a decreased clearance.
155. A PYY compound according to any one of the preceding embodiments which has the effect in vivo of decreasing the blood glucose determined in a single-dose study in a db/db mouse model.
156. A PYY compound according to any one of the preceding embodiments which has the effect in vivo of decreasing food intake determined in a single-dose study in a db/db mouse model.
157. A pharmaceutical composition comprising a PYY compound according to any one of embodiments 1-143, and at least one pharmaceutically acceptable excipient.
158. A PYY compound according to any one of embodiments 1-143, for use as a medicament.
159. A PYY compound according to any one of embodiments 1-143, for use in the treatment and/or prevention of all forms of diabetes and related diseases, such as eating disorders, diabetic complications, cardiovascular diseases and/or sleep apnoea; and/or for improving lipid parameters, improving β-cell function, and/or for delaying or preventing diabetic disease progression.

160. A PYY compound according to any one of embodiments 1-143, for use in the treatment and/or prevention of diabetes.

161. A PYY compound according to any one of embodiments 1-143, for use in the treatment and/or prevention of type 2 diabetes.

162. Use of a PYY compound according to any one of embodiments 1-143, for the manufacture of a medicament for the treatment and/or prevention of all forms of diabetes and related diseases, such as eating disorders, diabetic complications, cardiovascular diseases and/or sleep apnoea; and/or for improving lipid parameters, improving β-cell function, and/or for delaying or preventing diabetic disease progression.

163. Use of a PYY compound according to any one of embodiments 1-143, for the manufacture of a medicament for the treatment and/or prevention of diabetes.

164. Use of a PYY compound according to any one of embodiments 1-143, for the manufacture of a medicament for the treatment and/or prevention of type 2 diabetes.

165. A method of treatment and/or prevention of all forms of diabetes and related diseases, such as eating disorders, diabetic complications, cardiovascular diseases and/or sleep apnoea; and/or for improving lipid parameters, improving β-cell function, and/or for delaying or preventing diabetic disease progression by administering a pharmaceutically active amount of a PYY compound according to any one of embodiments 1-143.

166. A method of treatment and/or prevention of diabetes by administering a pharmaceutically active amount of a PYY compound according to any one of embodiments 1-143.

167. A method of treatment and/or prevention of type 2 diabetes by administering a pharmaceutically active amount of a PYY compound according to any one of embodiments 1-143.

168. A PYY compound according to any one of embodiments 1-143, for use in the treatment and/or prevention of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence.

169. A PYY compound according to any one of embodiments 1-143, for use in the treatment and/or prevention of obesity.

170. Use of a PYY compound according to any one of embodiments 1-143, in the manufacture of a medicament for the treatment and/or prevention of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence.

171. Use of a PYY compound according to any one of embodiments 1-143, in the manufacture of a medicament for the treatment and/or prevention of obesity.

172. A method of treatment and/or prevention of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence by administering a pharmaceutically active amount of a PYY compound according to any one of embodiments 1-143.

173. A method of treatment and/or prevention of obesity, by administering a pharmaceutically active amount of a PYY compound according to any one of embodiments 1-143.

EXAMPLES

This experimental part starts with a list of abbreviations, and is followed by a section including general methods for synthesising and characterising compounds of the invention. Then follows a number of Examples which relate to the preparation of specific PYY compounds, and at the end a number of examples have been included relating to the activity and properties of these compounds (section headed pharmacological methods). The examples serve to illustrate the invention.

LIST OF ABBREVIATIONS

ACN: acetonitrile
Ahx: 6-amino-hexanoic acid
Aib: alpha-aminoisobutanoic acid
Boc: tert butyloxycarbonyl
$CH_3CN$: acetonitrile
cpm: counts per minute
DCM: dichloromethane
DIC: Diisopropylcarbodiimide
DIPEA: diisopropylethylamine
DMF: N,N-dimethylformamide
Et2O: diethyl ether
Fmoc: 9H-fluoren-9-ylmethoxycarbonyl
HFIP: Hexafluoroisopropanol
HMWP: High molecular weight proteins
h: hours
$H_2O$: water
HOAc: acetic acid
HOBt: 1-Hydroxybenzotriazole
Min: minutes
Mtt: 4-methyltrityl
MW: Molecular weight
NMeArg: N(alpha)-methyl-L-arginine
NMF: 1-Methyl-formamide
NMP: 1-Methyl-pyrrolidin-2-one
OtBu: tert butyl ester
Pbf: 2,2,4,6,7-pentamethyldihydrobenzofuran-5-sulfonyl
PyBOP: benzotriazol-1-yl-oxytripyrrolidinophosphonium hexafluorophosphate
rpm: rounds per minute
r.t: Room temperature
tBu: tert butyl
TFA: trifluoroacetic acid
TIPS: triisopropylsilane
Trt: triphenylmethyl
Materials and Methods
General Methods of Preparation This section relates to methods for solid phase synthesis of peptide backbone and synthesis of side chain attached to backbone (SPPS methods, including methods for the coupling of amino acids, the de-protection of Fmoc-amino acids, methods for cleaving the peptide from the resin, and for its purification).

1. Synthesis of Resin Bound Protected Peptide Backbone

Procedure for the Automatic Step-Wise Assembly of Peptide Backbone.

The protected peptidyl resin was synthesized according to the Fmoc strategy on a solid phase peptide synthesiser Prelude (Protein Technologies, Tucson, USA) either 0.25 mmol scale or 0.4 mmol scale using the manufacturer supplied machine protocols. The Fmoc-protected amino acid derivatives used were the standard recommended: Fmoc-Ala-OH, Fmoc-Arg(Pbf)-OH, Fmoc-Asn(Trt)-OH, Fmoc-Asp(OtBu)-OH, Fmoc-Cys(Trt)-OH, Fmoc-Gln(Trt)-OH, Fmoc-Glu(OtBu)-OH, Fmoc-Glu-Otbu, Fmoc-Gly-OH, Fmoc-His(Trt)-OH, Fmoc-Ile-OH, Fmoc-Leu-OH, Fmoc-Lys(Boc)-OH, Fmoc-Lys(Mtt)-OH, Fmoc-Met-OH, Fmoc-Phe-OH, Fmoc-Pro-OH, Fmoc-Ser(tBu)-OH, Fmoc-Thr(tBu)-OH, Fmoc-Trp(Boc)-OH, Fmoc-Tyr(tBu)-OH, or, Fmoc-Val-OH etc. supplied from e.g., Bachem, Iris Biotech, Protein Technologies or Novabiochem. Fmoc-8-amino-3,6-dioxaoctanoic acid was purchased from Polypeptides. If nothing else is specified the natural L-form of the amino acids are used. Coupling was done by the use of DIC (dicyclohexylcarbodiimide) and Ozyma Pure (ethyl 2-cyano-2-(hydroxyimino)-acetate, Merck, Novabiochem, Switzerland) mediated couplings in NMP (N-methyl pyrrolidone). The coupling of the Fmoc-amino acid was done as described above using 4-8 time excess of amino acid relative to resin substitution (4-8 eq). Coupling time ranged from 1 hour up to 4 hours. The Fmoc-Arg(pbf)-OH was coupled using a double coupling procedure (1 hour+1 hour). The resin used for the synthesis of the peptide amides can be Tentagel RAM (Rapp Polymere, Germany), Rink amid ChemMatrix resin (Matrix Innovation, Canada) Rink-Amide resin (Merck/Novabiochem). The protected amino acid derivatives used were standard Fmoc-amino acids (supplied from e.g. Protein Technologies, or Novabiochem. The epsilon amino group of lysine to be derivatised was protected with Mtt. The N-terminal amino acid or building was coupled as a Boc-protected amino acid, e.g., Boc-Ile. Alternatively isovaleric acid was coupled according to the above described coupling procedure for the Fmoc-amino acids. The step-wise solid phase assembly on the Prelude was done using the following steps: 1) deprotection (removal of Fmoc) by the use of 25% piperidine in NMP for 2×4 min., step 2) Wash (removal of piperidine) with NMP and DCM, step 3) Coupling of Fmoc-amino acid (0.3M Fmoc-amino acid in 0.3M Oxyma Pure in NMP) 4-8 eq excess for 1-4 hours coupling initiated by adding 1/10 volume of 3M DIC in NMP and 1/10 volume collidine in NMP. Mixing was done by occasional bubbling with nitrogen, step 4) Wash (removal of excess amino acid and reagents by the use of NMP and DCM). Last step included washing with DCM which made the resin ready for attachment of a modifying group on lysine side chain.

2. Attachment of Modifying Groups to Resin Bound Protected Peptide Backbone

Procedure for Manual Removal of Mtt-Protection (Lysine (Mtt)):

Before synthesis of the modifying group, the Mtt group on the site of attachment (lysine) must be removed. The resin was placed in a syringe or reaction flask and treated with 75% hexafluroisopropanol (HFIP)+25% DCM for 2×30 minutes to remove the Mtt group. The resin was then washed with DCM and NMP as described above and neutralized with 5% DIPEA (neutralisation step) in NMP or 25% piperidine in NMP followed by NMP washing before coupling the modifying group. Alternatively, the neutralisation step was omitted.

Procedure for Prelude Removal of Mtt-Protection (Lysine (Mtt)):

On the Prelude the resin was treated with 75% hexafluoroisopropanol (HFIP)+25% DCM for 2×2 minutes followed 2×30 minutes to remove the Mtt group on the lysine. The resin was then washed with DCM and NMP followed by a neutralisation step using 25% piperidine in NMP by 4 minutes, and was then ready for the synthesis of the modifying group.

Procedure for Manual Synthesis of Modifying Groups onto a Lysine Residue:

The building blocks Fmoc-8-amino-3,6-dioxaoctanoic acid (CAS No. 166108-71-0), Fmoc-TTDS-OH (CAS No. 172089-14-4, IRIS Biotech GmbH), Fmoc-6-amino-hexanoic acid (Fmoc-Ahx; CAS No. 88574-06-5), Fmoc-L-Glu-OtBu (84793-07-7), and eicosanedioic acid mono-tert-butyl ester (CAS No. 843666-40-0) were coupled using DIC and Oxyma Pure in 4-8 eq relative to resin substitution. The coupling time was 2-16 hours usually followed by a capping step using 1 M acetic anhydride for 15-60 min. The Fmoc-group was removed by 25% piperidine in NMP for 10-30 min. followed by washing. The 16-sulfonic hexadecanoic acid was solubilised in NMP or N-methylformamid (NMF) at 60 degree Celsius or above and activated by PyBOP 1 eq relative to the sulfonic hexadecanoic acid and 2 eq of diisopropylethylamine (DIPEA) relative to sulfonic hexadecanoic acid was also added. The peptidyl resin was washed with hot NMP or NMF just prior to the addition of activated sulfonic hexadecanoic acid. An excess of 3-4 of the sulfonic building block was used and coupling allowed to proceed >16 hours.

Procedure for Automated Synthesis of Modifying Groups onto a Lysine Residue:

For the synthesis of the modifying groups the following building blocks were used: Fmoc-8-amino-3,6-dioxaoctanoic acid, Fmoc-TTDS-OH,), Fmoc-6-amino-hexanoic acid (Fmoc-Ahx; CAS No. 88574-06-5), Fmoc-Glu-OtBu, and eicosanedioic acid mono-tert-butyl ester (CAS No. 843666-40-0). Modifying groups were coupled using DIC and Oxyma Pure in 4-8 eq relative to resin substitution. The coupling time was 2-16 hours usually followed by a capping step using 1 M acetic anhydride for 20 min. The Fmoc-group was removed by 25% piperidine in NMP for 2×4 min. followed by washing as described in the SPPS of the peptide backbone. All other synthesis steps were also the same as described above with the backbone synthesis. The coupling of 16-sulfonic hexadecanoic acid was done by the manual procedure as described above using pyBOP as coupling reagent.

3. Cleavage of Resin Bound Peptide with or without Attached Modifying Groups and Purification Prior to TFA deprotection the peptidyl resin was washed with DCM or diethyl ether and dried. The peptide and side chain protection groups were removed by addition of 20-40 ml (0.25 mmol scale) 30-60 (0.4 mmol scale) ml 92% TFA, 5% TIPS and 3% $H_2O$ for 2-4 hours. Then TFA was filtered and in some cases concentrated by a stream of argon and diethyl ether was added to precipitate the peptide. The peptide was washed three-five times with diethyl ether and dried.

General Methods of Detection and Characterisation

This section relates to methods for detection and characterisation of the resulting peptides, including LCMS, MALDI and UPLC methods.

LC-MS Method (457 LCMS01)
System: Agilent 1290 infinity series UPLC
Column: Eclipse C18+ 2.1×50 mm 1.8 u
Detector: Agilent Technologies LC/MSD TOF 6230 (G6230A)
Detector setup:
Ionisation method: Agilent Jet Stream source
Scanning range: m/z min. 100, m/z max. 3200
linear reflector mode
positive mode
System:
Linear gradient: 5% to 95% B
Gradient run-time: 6 minutes 0-4.5 min 5-95% B, 4.5-5 95% B, 5-5.5 95-5% B 5.5-6 5% B
Flow rate: 0.40 ml/min fixed
Column temperature: 40° C.
Solvent A: 99.90% H2O, 0.02% TFA
Solvent B: 99.90% CH3CN, 0.02% TFA
MALDI-MS Method Molecular weights of the peptides were determined using matrix-assisted laser desorption time of flight mass spectroscopy (MALDI-MS), recorded on a Microflex (Bruker). A matrix of alpha-cyano-4-hydroxy cinnamic acid was used. The molecular weight of the product was calculated based on the result of MALDI-MS analysis using the software supplied from the manufacturer.

Synthesis of Intermediates

Synthesis of 16-sulfo-hexadecanoic acid

16-Hexadecanolide (997 g, 3.92 mol) was dissolved in methanol (15.1 L) and toluene-4-sulfonic acid monohydrate (90.0 g, 0.473 mol) was added. Reaction mixture was heated in 50 L reactor at 55° C. for 16 hours. After cooling down sodium hydrogen carbonate (56.0 g, 0.67 mol) was added and the reaction mixture was stirred for 15 min. Solvent was evaporated on Heidolph 20 L rotary evaporator. Ethyl acetate (12 L) was added and the mixture was extracted with 5% solution of sodium hydrogen carbonate (10 L). Organic layer was separated; emulsion layer was extracted with ethyl acetate (3×3 L), white insoluble muddy material was separated and ethyl acetate layer was washed again with 5% solution of sodium hydrogen carbonate (5 L). Organic layers were combined and washed with saturated solution of sodium hydrogen carbonate (5 L) and brine (10 L). Solvent was evaporated on Heidolph 20 L rotary evaporator. Crude product was crystallized from hexanes (8 L). Hot solution in hexanes was decanted and then let to crystallize in ice bath. The material was filtered on large frit and washed with cold hexanes (2 L). Pure material was dried in vacuo.

Yield: 1062.2 g (95%). $R_F$ (SiO$_2$, dichloromethane/methanol 95:5): 0.65.

$^1$H NMR spectrum (300 MHz, CDCl$_3$, $\delta_H$): 3.67 (s, 3H); 3.67-3.60 (m, 2H); 2.30 (t, J=7.5 Hz, 2H); 1.67-1.53 (m, 4H); 1.25 (s, 22H).

The above ester (957 g, 3.34 mol) was dissolved in dichloromethane (7 L) on Heidolph 20 L rotary evaporator. Triethylamine (695 mL, 4.98 mol) was added, reaction mixture was cooled to 0° C. (by putting ice into evaporator bath) and methanesulfonyl chloride (325 mL, 4.19 mol) in dichloromethane (200 mL) was added slowly during 10 minutes by external tubing using small vacuum. Then the reaction mixture was heated to 35° C. for 1 hour. NMR analysis showed complete conversion. Water was added (690 mL) and solvents were evaporated. Ethyl acetate (8 L) was added and the mixture was washed with 1 M hydrochloric acid (4 L) and 5% solution of sodium carbonate (4 L). Since sodium carbonate extraction formed an emulsion this layer was extracted with ethyl acetate (4 L) and added to main portion. Combined ethyl acetate layer was washed with brine (4 L), dried over anhydrous sodium sulfate and filtered. Solvent was evaporated giving 16-methanesulfonyloxy-hexadecanoic acid methyl ester as white solid.

Yield: 1225.4 g (100%).

$^1$H NMR spectrum (300 MHz, CDCl$_3$, $\delta_H$): 4.22 (t, 3=6.6 Hz, 2H); 3.66 (s, 3H); 3.00 (s, 3H); 2.30 (t, J=7.5 Hz, 2H) 1.82-1.67 (m, 2H); 1.68-1.54 (m, 2H); 1.36-1.17 (m, 22H).

The above mesylate (1.23 kg, 3.34 mol) was dissolved in acetone (8 L) and lithium bromide (585 g, 6.73 mol) was added and the reaction mixture was heated on Heidolph 20 L rotary evaporator at 50° C. for 12 hours. After cooling down solvent was evaporated, ethyl acetate (10 L) was added and the mixture was washed with 5% solution of sodium hydrogencarbonate (3×15 L) and brine (8 L). Solvent was evaporated to dryness to yield 16-bromo-hexadecanoic acid methyl ester as pale yellow oil which started to crystallize.

Yield: 1219 g (105%); contains acetone and product of acetone aldolization.

$R_F$ (SiO$_2$, hexanes/ethyl acetate 9:1): 0.90.

$^1$H NMR spectrum (300 MHz, CDCl$_3$, $\delta_H$): 3.65 (s, 3H); 3.42 (t, J=6.9 Hz, 2H); 2.32 (t, J=7.5 Hz, 2H); 1.92-1.77 (m, 2H) 1.69-1.53 (m, 2H); 1.50-1.35 (m, 2H); 1.25 (bs, 10H).

Solutions of sodium sulfite (327 g, 2.60 mol) in water (1.26 L) and 16-bromo-hexadecanoic acid methyl ester (728 g, 2.00 mol, 96% purity) in 1-propanol (945 mL) and methanol (420 mL) were heated to reflux in 6 L reactor equipped with mechanical stirrer for 48 hours. The reaction mixture was cooled to 27° C. and diluted with tetrahydrofuran (2 L). Reaction mixture was filtered and solid material was washed with tetrahydrofuran (3×700 mL). Filtrate was cooled to 0° C. and another portion of material was precipitated. This precipitate was filtered and washed with tetrahydrofuran (2×200 mL). Solids were combined and mixed with water (8.4 L) in 20 L pot. Solution of sodium hydroxide (120 g, 3.00 mol) was added. The mixture was heated to boiling for about 5 hours. Solution of sulfuric acid (430 mL, 8.00 mol) in water (500 mL) was slowly added into the reaction mixture (sulfur dioxide is formed). Reaction mixture was heated to boiling for 10 minutes and then let to cool to 15° C. (ice bath). The mixture was filtered on Bchner funnel through filter paper Seitz (several layers filter) applying vacuo. This procedure was very slow and took two days. Solid material was several times washed with distilled water until pH of filtrate was between 2 and 3. This procedure took about three days. Muddy white material was dried in oven at 80° C. giving desired product.

Yield: 510 g (76%).

$^1$H NMR spectrum (300 MHz, DMSO-d$_6$, $\delta_H$): 2.45-2.33 (m, 2H); 2.18 (t, 3=7.3 Hz, 2H); 1.60-1.40 (m, 4H); 1.24 (s, 22H).

MS-ESI (neg, sample in H$_2$O/MeCN+NaHCO$_3$; m/z): 335.5 (M–H)$^-$, 357.5 (M–2H+Na)$^-$, 167.3 (M–2H)$^{2-}$ Example 1: Synthesis of PYY Compounds The PYY compounds of the invention were synthesised according to the general methods of preparation as described above.

hPYY(3-36)

IKPEAPGEDASPEELNRYYASLRHYLNLVTRQRY-NH₂
  MW calculated: 4049.6 g/mol
  MALDI MS, Found: 4048.2 g/mol Compound 1

N{Epsilon-7}-[(4S)-4-carboxy-4-[[(4S)-4-carboxy-4-(17-carboxyheptadecanoylamino)-butanoyl]amino]butanoyl]-[Arg4,Lys7,Gln18,Tyr28,Trp30,Leu31]hPYY(3-36)

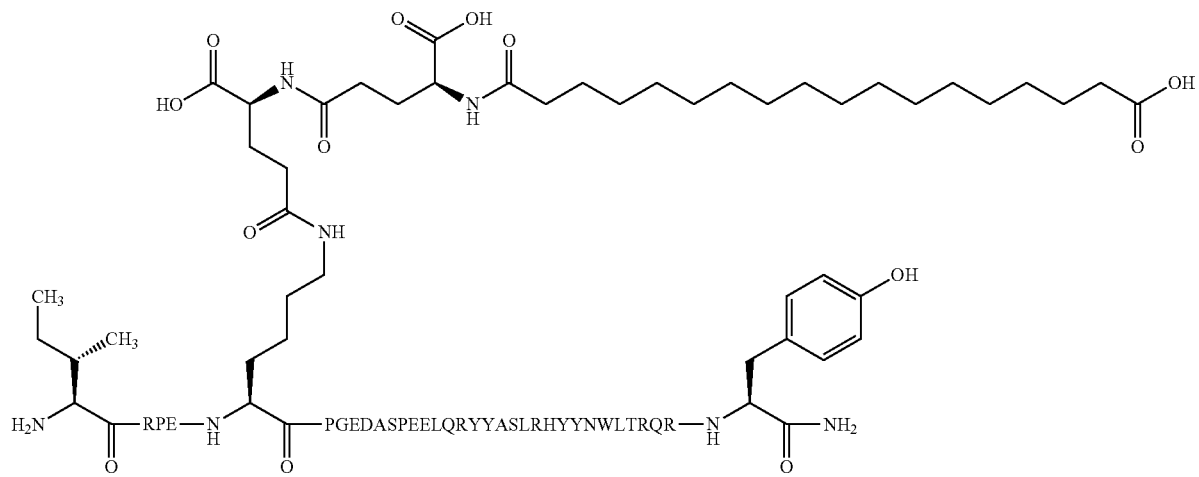

MW (average) calculated: 4840.37 g/mol
457_LCMS01: Found [M+5H]5+ 969.06
The amino acid sequence of [Arg4,Lys7,Gln18,Tyr28,Trp30,Leu31]hPYY(3-36) is given in SEQ ID NO:3.

Compound 2

N{alpha-4}-(3-Methylbutanoyl)-N{Epsilon-7}-[(4S)-4-carboxy-4-(17-carboxy-heptadecanoylamino)butanoyl]-[Arg4,Lys7,Gln18,Tyr28,Trp30,Leu31]hPYY(4-36)

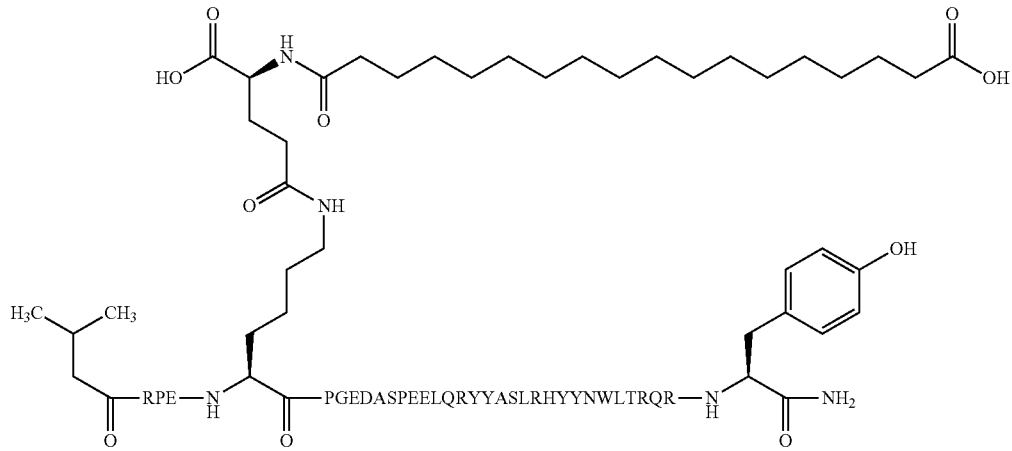

MW (average) calculated: 4682.21 g/mol
457_LCMS01: Found [M+4H]4+: 1171.36; [M+5H]5+ 937.28

The amino acid sequence of [Arg4,Lys7,Gln18,Tyr28,Trp30,Leu31]hPYY(4-36) is given in SEQ ID NO:4.

Compound 3

N{alpha-4}-(3-Methylbutanoyl)-N{Epsilon-7}-[2-[2-[2-[[2-[2-[2-[[(4S)-4-carboxy-4-(17-carboxyhep-tadecanoylamino)butanoyl]amino]ethoxy]ethoxy]acetyl]amino]-ethoxy]ethoxy]acetyl]-[Arg4,Lys7,Gln18,Tyr28,Trp30,Leu31]hPYY(4-36)

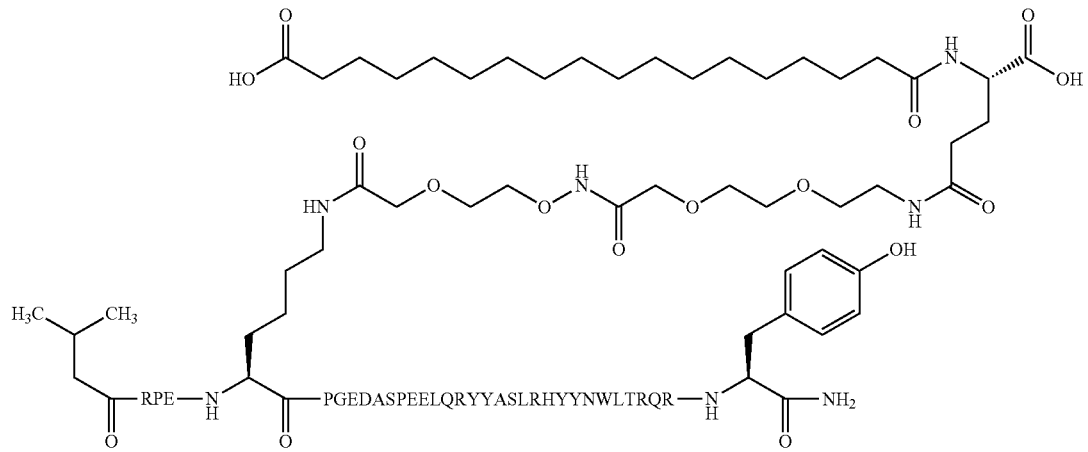

MW (average) calculated: 4972.52 g/mol.
457_LCMS01: Found [M+4H]4+: 1244.14;
The amino acid sequence of [Arg4,Lys7,Gln18,Tyr28,Trp30,Leu31]hPYY(4-36) is given in SEQ ID NO:4.

Compound 4

N{alpha-4}-(3-Methylbutanoyl)-N{Epsilon-7}-6-[[(4S)-4-carboxy-4-(17-carboxy-heptadecanoy-lamino)butanoyl]amino]hexanoyl-[Arg4,Lys7,Pro9,Gln18,Tyr28, Trp30,Leu31]hPYY(4-36)

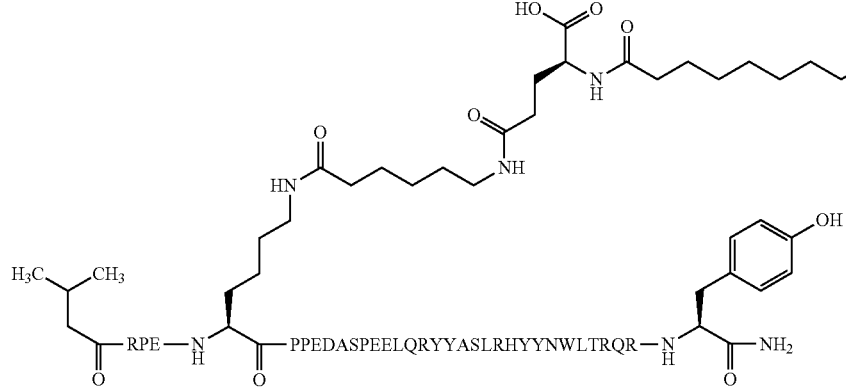

MW (average) calculated: 4835.43 g/mol.
457_LCMS01: Found [M+4H]4+: 1209.62; [M+5H]5+: 967.91.

The amino acid sequence of [Arg4,Lys7,Pro9,Gln18,Tyr28,Trp30,Leu31]hPYY(4-36) is given in SEQ ID NO:5.

Compound 5

N{alpha-4}-(3-Methylbutanoyl)-N{Epsilon-7}-[2-
[2-[2-[[2-[2-[2-[[(4S)-4-carboxy-4-[[(4S)-4-carboxy-
4-(17-carboxyheptadecanoylamino)butanoyl]amino]
butanoyl]amino]-ethoxy]ethoxy]acetyl]amino]
ethoxy]ethoxy]acetyl]-[Arg4,Lys7,Gln18,Tyr28,
Trp30, Leu31]hPYY(4-36)

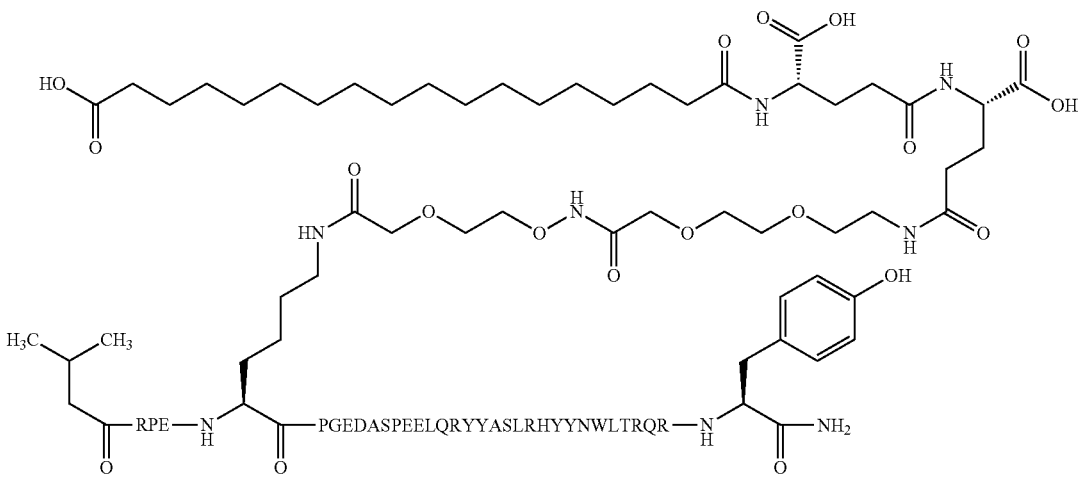

MW (average) calculated: 5101.63 g/mol.
457_LCMS01: Found [M+4H]4+: 1276.46;
The amino acid sequence of [Arg4,Lys7,Gln18,Tyr28,
Trp30,Leu31]hPYY(4-36) is given in SEQ ID NO:4.

Compound 6

N{alpha-4}-(3-Methylbutanoyl)-N{Epsilon-7}-
[(4S)-4-carboxy-4-(15-carboxy-pentadecanoy-
lamino)butanoyl]-[Arg4,Lys7,Gln18,Tyr28,Trp30,
Leu31]hPYY(4-36)

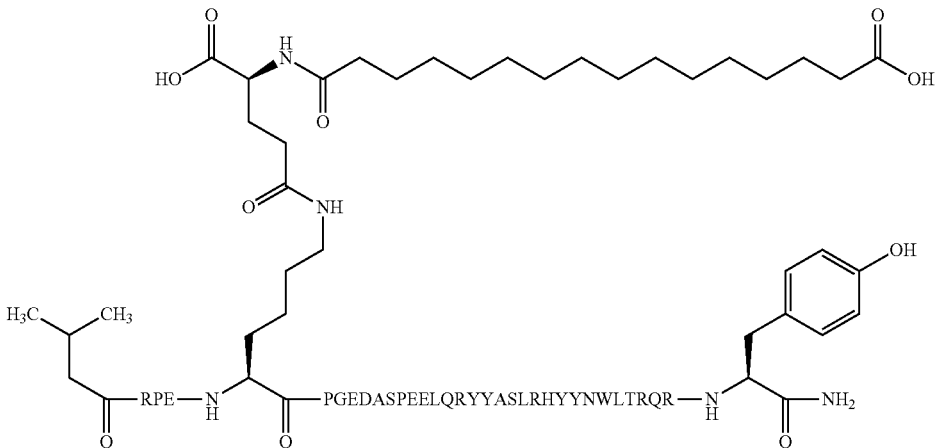

MW (average) calculated: 4654.18 g/mol.
457_LCMS01: Found [M+4H]4+: 1164.33; Found
[M+5H]5+: 931.67.
The amino acid sequence of [Arg4,Lys7,Gln18,Tyr28,
Trp30,Leu31]hPYY(4-36) is given in SEQ ID NO:4.

Compound 7

N{alpha-4}-(3-Methylbutanoyl)-N{Epsilon-7}-[(4S)-4-carboxy-4-(19-carboxy-nonadecanoylamino)butanoyl]-[Arg4,Lys7,Gln18,Tyr28,Trp30,Leu31] hPYY(4-36)

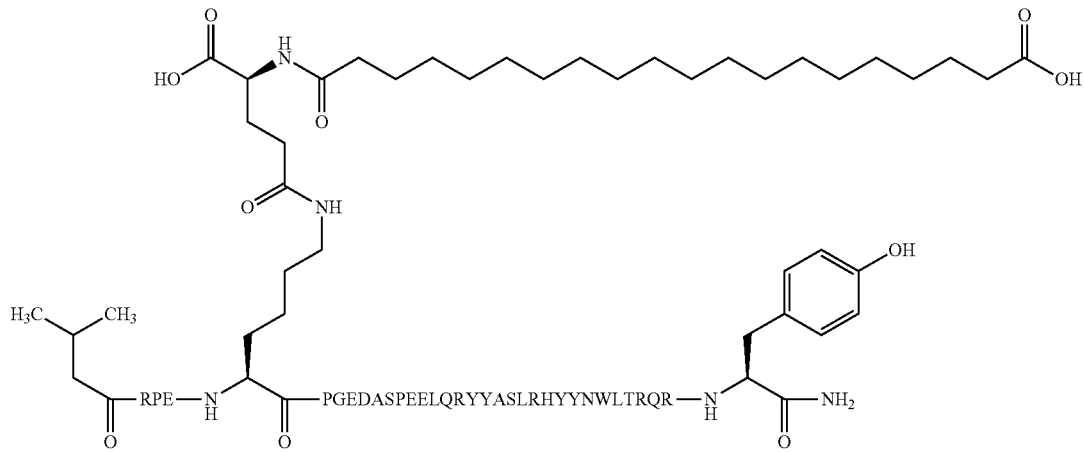

MW (average) calculated: 4710.26 g/mol.

457_LCMS01: Found [M+4H]4+: 1178.36; Found [M+5H]5+: 942.89.

The amino acid sequence of [Arg4,Lys7,Gln18,Tyr28,Trp30,Leu31]hPYY(4-36) is given in SEQ ID NO:4.

Compound 8

N{alpha-4}-(3-Methylbutanoyl)-N{Epsilon-7}-[2-[2-[2-[[(4S)-4-carboxy-4-(17-carboxy-heptadecanoylamino)butanoyl]amino]ethoxy]ethoxy]acetyl]-[Arg4,Lys7,Gln18,Tyr28, Trp30,Leu31]hPYY(4-36)

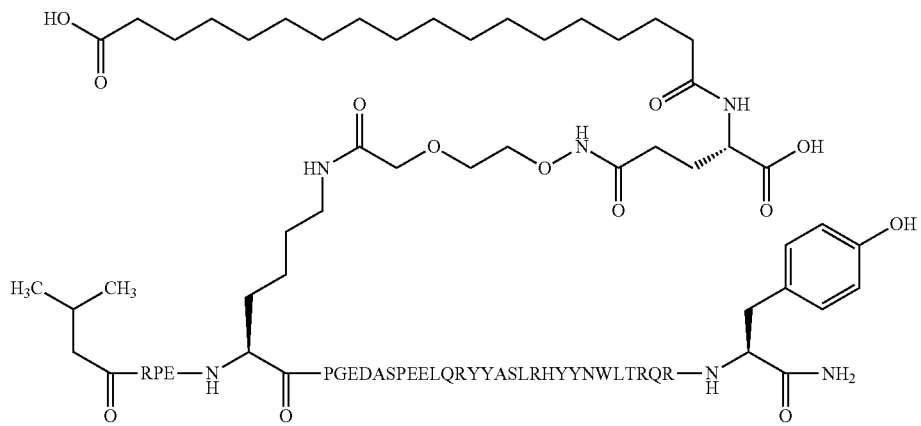

MW (average) calculated: 4827.37 g/mol.

457_LCMS01: Found [M+4H]4+: 1207.62; Found [M+5H]5+: 966.29.

The amino acid sequence of [Arg4,Lys7,Gln18,Tyr28,Trp30,Leu31]hPYY(4-36) is given in SEQ ID NO:4.

Compound 9

N{alpha-4}-(3-Methylbutanoyl)-N{Epsilon-7}-
[(4S)-4-carboxy-4-(16-sulfohexadecanoyl-amino)
butanoyl]-[Arg4,Lys7,Gln18,Tyr28,Trp30,Leu31]
hPYY(4-36)

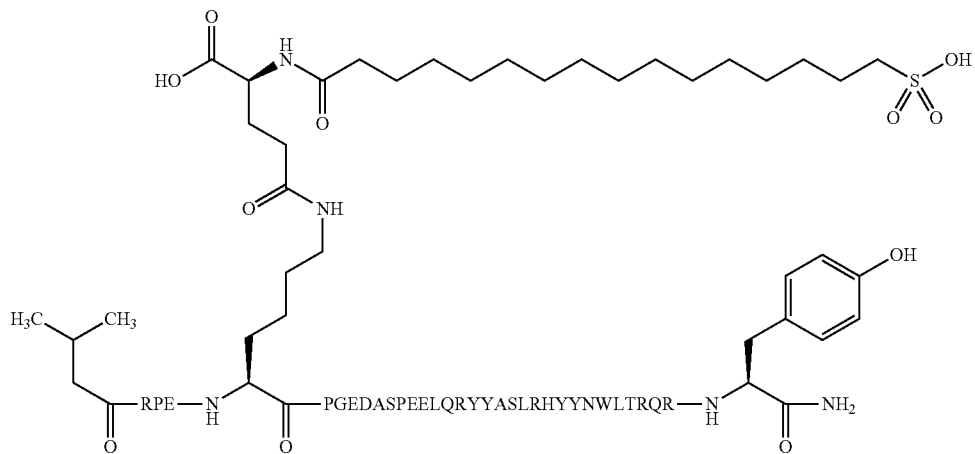

MW (average) calculated: 4827.37 g/mol.
457_LCMS01: Found [M+4H]4+: 1177.09.
The amino acid sequence of [Arg4,Lys7,Gln18,Tyr28, Trp30,Leu31]hPYY(4-36) is given in SEQ ID NO:4.

Compound 10

N{alpha-4}-(3-Methylbutanoyl)-N{Epsilon-7}-6-
[[(4S)-4-carboxy-4-(19-carboxy-nonadecanoy-
lamino)butanoyl]amino]hexanoyl-[Arg4,Lys7,
Gln18,Tyr28,Trp30, Leu31]hPYY(4-36)

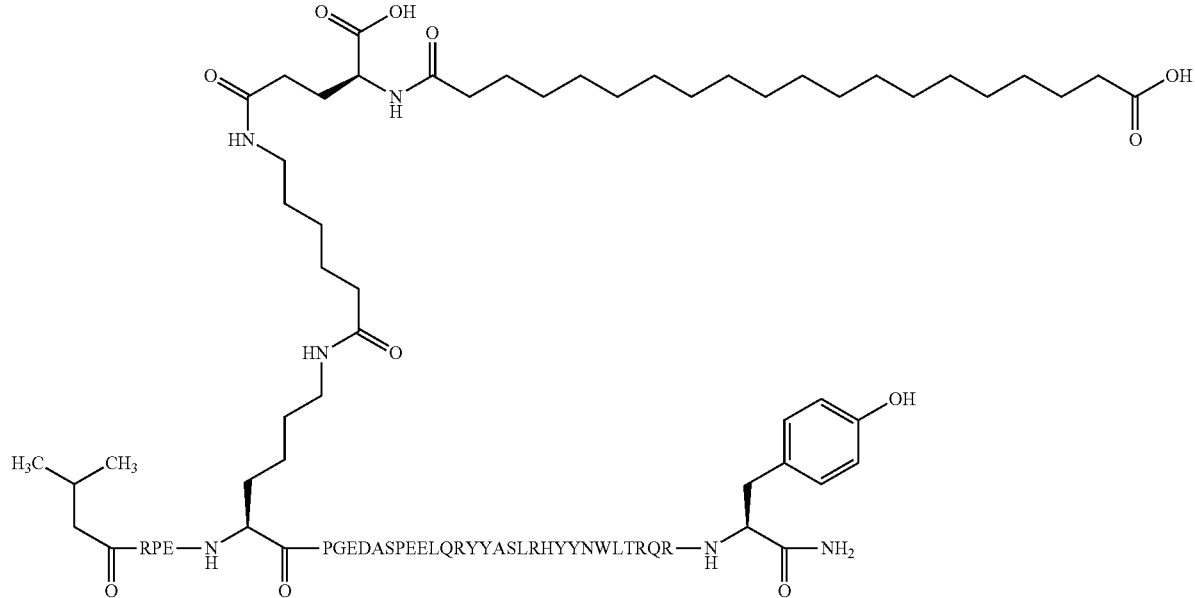

MW (average) calculated: 4823.42 g/mol.
457_LCMS01: Found [M+4H]4+: 1206.63.
The amino acid sequence of [Arg4,Lys7,Gln18,Tyr28, Trp30,Leu31]hPYY(4-36) is given in SEQ ID NO:4.

Compound 11
N{alpha-4}-(3-Methylbutanoyl)-N{Epsilon-7}-[(4S)-4-carboxy-4-[[(4S)-4-carboxy-4-(17-carboxy-heptadecanoylamino)butanoyl]amino]butanoyl]-[Arg4,Lys7,Pro9,Gln18, Tyr28,Trp30,Leu31]hPYY (4-36)
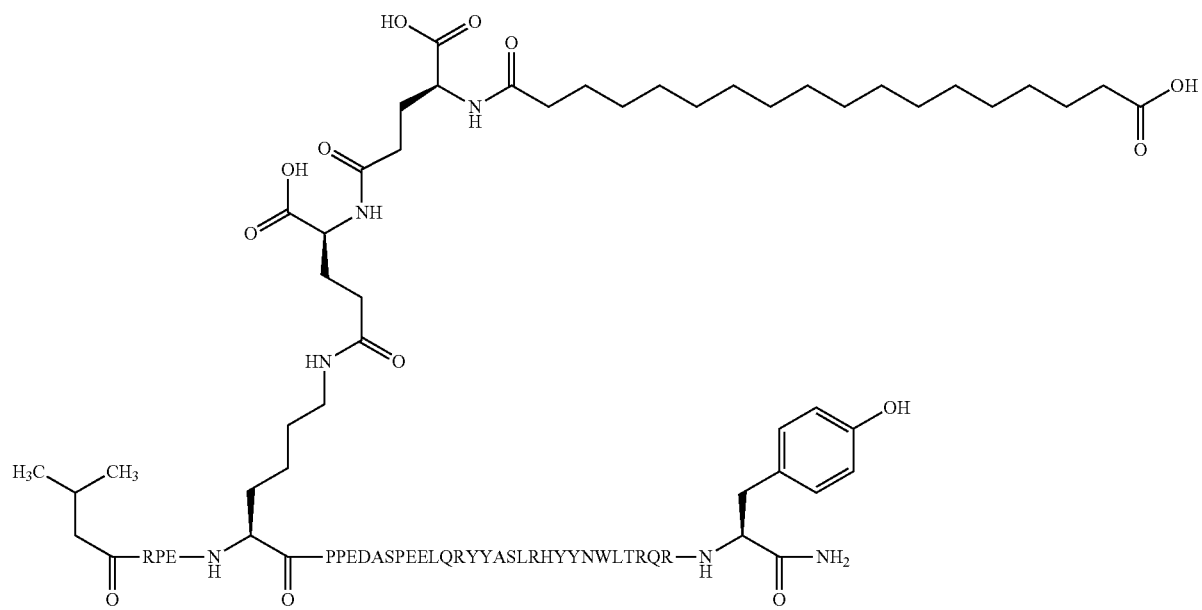
MW (average) calculated: 4851.39 g/mol.
457_LCMS01: Found [M+4H]4+: 1213.61.
The amino acid sequence of [Arg4,Lys7,Pro9,Gln18, Tyr28,Trp30,Leu31]hPYY(4-36) is given in SEQ ID NO:5.

Compound 12

N{alpha-4}-(3-Methylbutanoyl)-N{Epsilon-7}-[[(4S)-4-carboxy-4-[[(4S)-4-carboxy-4-(19-carboxynonadecanoylamino)butanoyl]amino]butanoyl]-[Arg4,Lys7,Pro9,Gln18, Tyr28,Trp30,Leu31]hPYY(4-36)

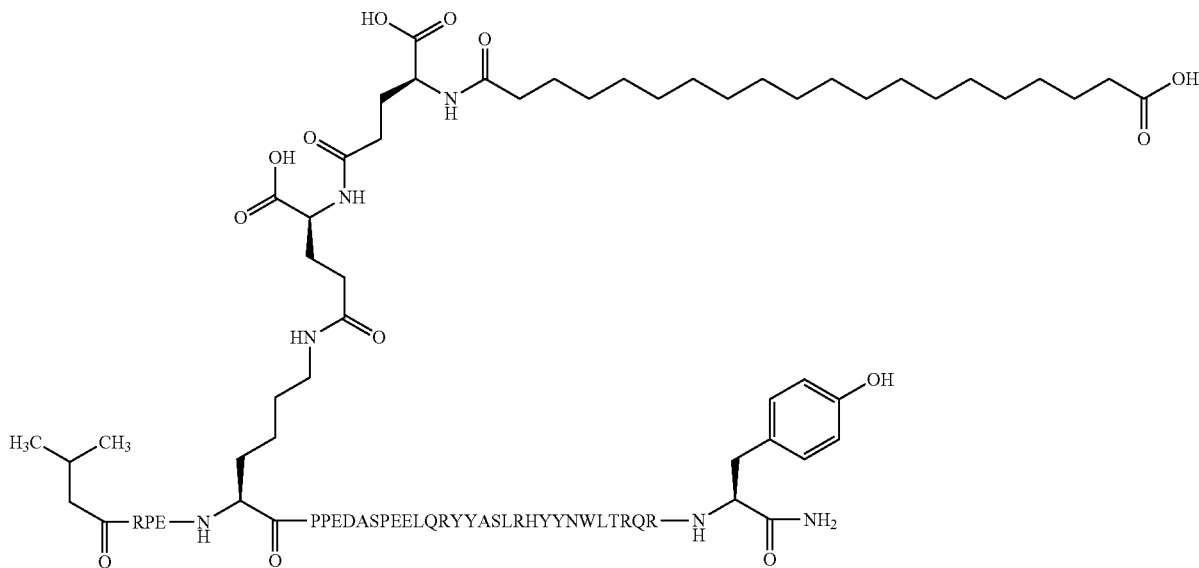

MW (average) calculated: 4879.44 g/mol.
457_LCMS01: Found [M+4H]4+: 1220.62.
The amino acid sequence of [Arg4,Lys7,Pro9,Gln18, Tyr28,Trp30,Leu31]hPYY(4-36) is given in SEQ ID NO:5.

Compound 13

N{alpha-4}-(3-Methylbutanoyl)-N{Epsilon-7}-[2-[2-[2-[[2-[2-[[(4S)-4-carboxy-4-(17-carboxyheptadecanoylamino)butanoyl]amino]ethoxy]ethoxy]acetyl]amino]-ethoxy]ethoxy]acetyl]-[Arg4,Lys7,Ser9,Gln18,Tyr28,Trp30,Leu31]hPYY(4-36)

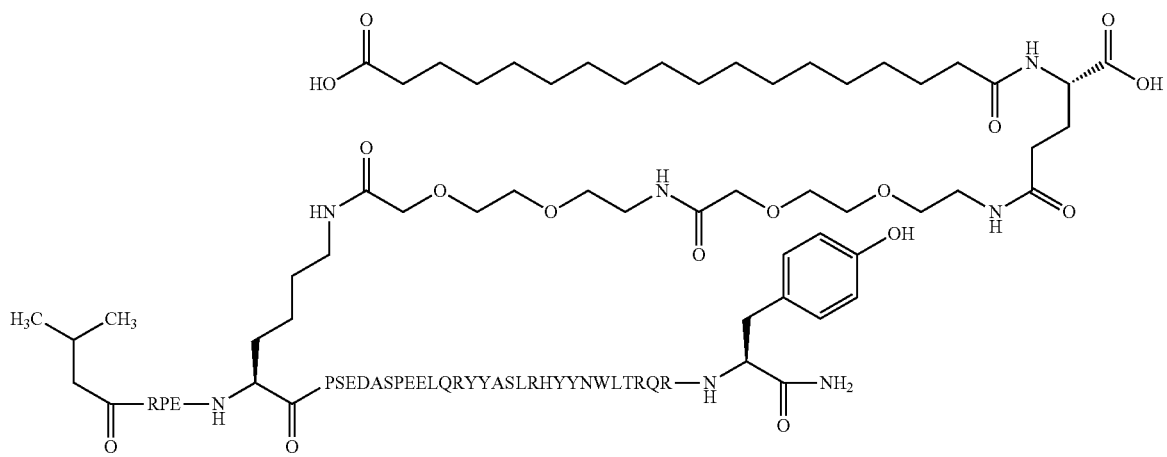

MW (average) calculated: 5002.55 g/mol.
457_LCMS01: Found [M+4H]4+: 1251.75.
The amino acid sequence of [Arg4,Lys7,Ser9,Gln18, Tyr28,Trp30,Leu31]hPYY(4-36) is given in SEQ ID NO:6.

Compound 14

N{alpha-4}-(3-Methylbutanoyl)-N{Epsilon-7}-[2-[2-[2-[[2-[2-[2-[[(4S)-4-carboxy-4-(17-carboxyhep-tadecanoylamino)butanoyl]amino]ethoxy]ethoxy]acetyl]amino]-ethoxy]ethoxy]acetyl]-[Arg4,Lys7,Thr9,Gln18,Tyr28,Trp30,Leu31]hPYY(4-36)

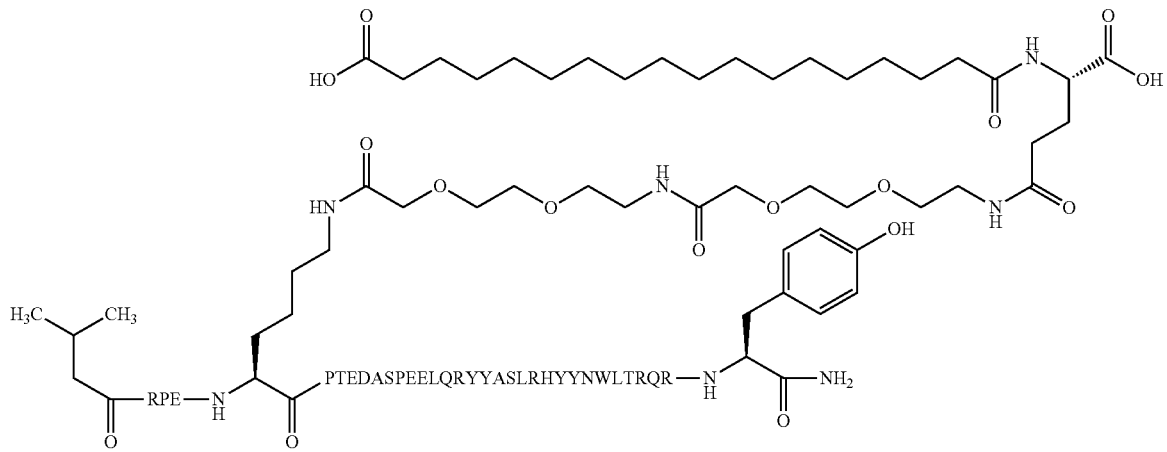

MW (average) calculated: 5016.58 g/mol.
457_LCMS01: Found [M+4H]4+: 1255.19.

The amino acid sequence of [Arg4,Lys7,Thr9,Gln18,Tyr28,Trp30,Leu31]hPYY(4-36) is given in SEQ ID NO:7.

Compound 15

N{alpha-4}-(3-Methylbutanoyl)-N{Epsilon-7}-[(4S)-4-carboxy-4-(17-carboxy-heptadecanoylamino)butanoyl]-[Arg4,Lys7,Thr13,Gln18,Tyr28,Trp30,Leu31]hPYY(4-36)

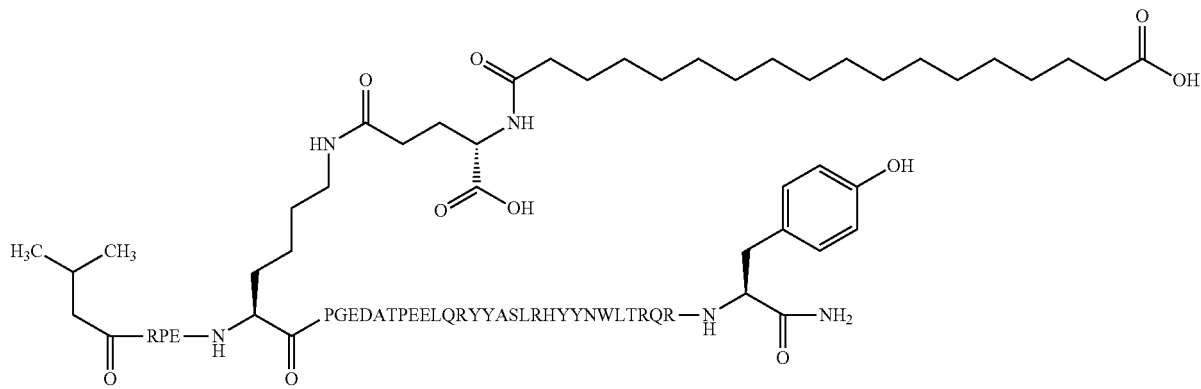

MW (average) calculated: 5016.58 g/mol.
457_LCMS01: Found [M+4H]4+: 1174.85.

The amino acid sequence of [Arg4,Lys7,Thr13,Gln18,Tyr28,Trp30,Leu31]hPYY(4-36) is given in SEQ ID NO:8.

Compound 16

N{alpha-4}-(3-Methylbutanoyl)-N{Epsilon-7}-[2-[2-[2-[[2-[2-[2-[[(4S)-4-carboxy-4-(17-carboxyheptadecanoylamino)butanoyl]amino]ethoxy]ethoxy]acetyl]amino]-ethoxy]ethoxy]acetyl]-[Arg4,Lys7,Thr13,Gln18,Tyr28,Trp30,Leu31]hPYY(4-36)

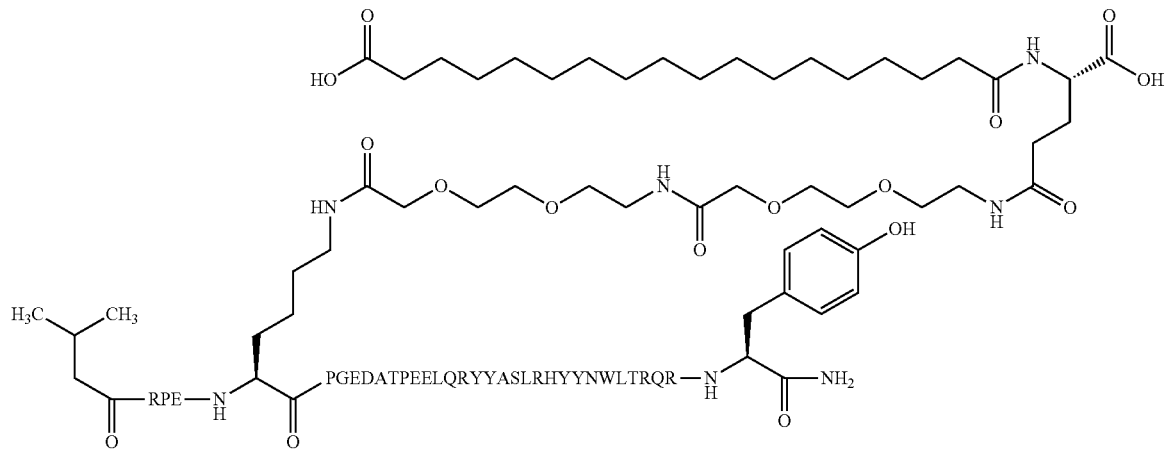

MW (average) calculated: 4986.55 g/mol.
457_LCMS01: Found [M+4H]4+: 1247.70.
The amino acid sequence of [Arg4,Lys7,Thr13,Gln18,Tyr28,Trp30,Leu31]hPYY(4-36) is given in SEQ ID NO:8.

Compound 17

N{alpha-4}-(3-Methylbutanoyl)-N{Epsilon-7}-[(4S)-4-carboxy-4-(17-carboxy-heptadecanoylamino)butanoyl]-[Arg4,Lys7,Gln18,Ala24,Tyr28,Trp30,Leu31]hPYY(4-36)

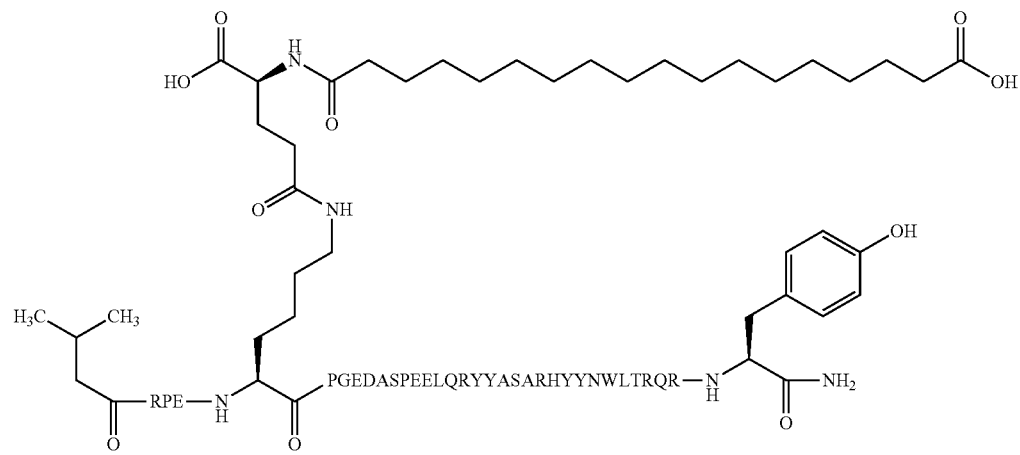

MW (average) calculated: 4640.13 g/mol.

457_LCMS01: Found [M+4H]4+: 1161.08; Found [M+5H]5+: 928.87.

The amino acid sequence of [Arg4,Lys7,Gln18,Ala24,Tyr28,Trp30,Leu31]hPYY(4-36) is given in SEQ ID NO:9.

Compound 18

N{alpha-4}-(3-Methylbutanoyl)-N{Epsilon-7}-
[(4S)-4-carboxy-4-(17-carboxy-heptadecanoy-
lamino)butanoyl]-[Arg4,Lys7,Gln18,Ile24,Tyr28,
Trp30,Leu31]hPYY(4-36)

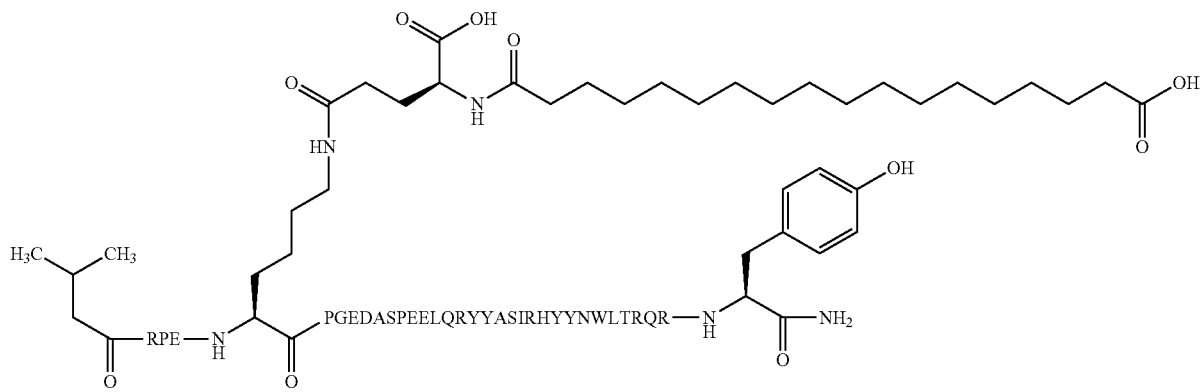

MW (average) calculated: 4682.21 g/mol.
457_LCMS01: Found [M+4H]4+: 1171.36;
The amino acid sequence of [Arg4,Lys7,Gln18,Ile24,Tyr28,Trp30,Leu31]hPYY(4-36) is given in SEQ ID NO:10.

Compound 19

N{alpha-4}-(3-Methylbutanoyl)-N{Epsilon-7}-6-
[[(4S)-4-carboxy-4-(19-carboxy-nonadecanoy-
lamino)butanoyl]amino]hexanoyl-[Arg4,Lys7,
Gln18,Ile24,Tyr28,Trp30, Leu31]hPYY(4-36)

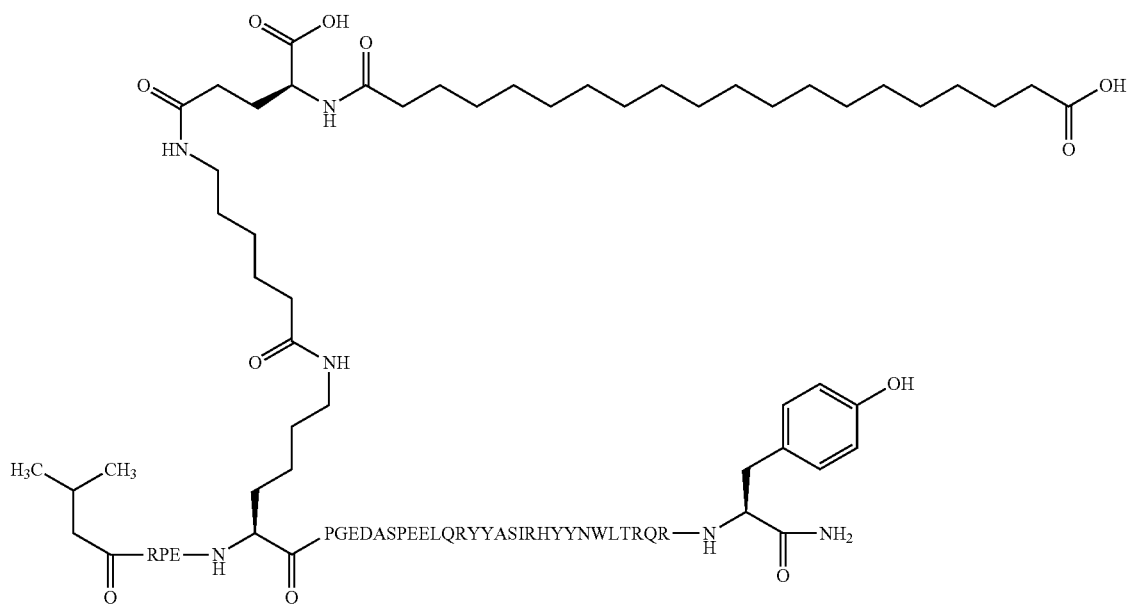

MW (average) calculated: 4823.42 g/mol.
457_LCMS01: Found [M+4H]4+: 1206.86;
The amino acid sequence of [Arg4,Lys7,Gln18,Ile24,Tyr28,Trp30,Leu31]hPYY(4-36) is given in SEQ ID NO:10.

Compound 20

N{alpha-4}-(3-Methylbutanoyl)-N{Epsilon-7}-6-[[(4S)-4-carboxy-4-(17-carboxy-heptadecanoylamino)butanoyl]amino]hexanoyl-[Arg4,Lys7, Gln18,Ile24, Tyr28,Trp30,Leu31]hPYY(4-36)

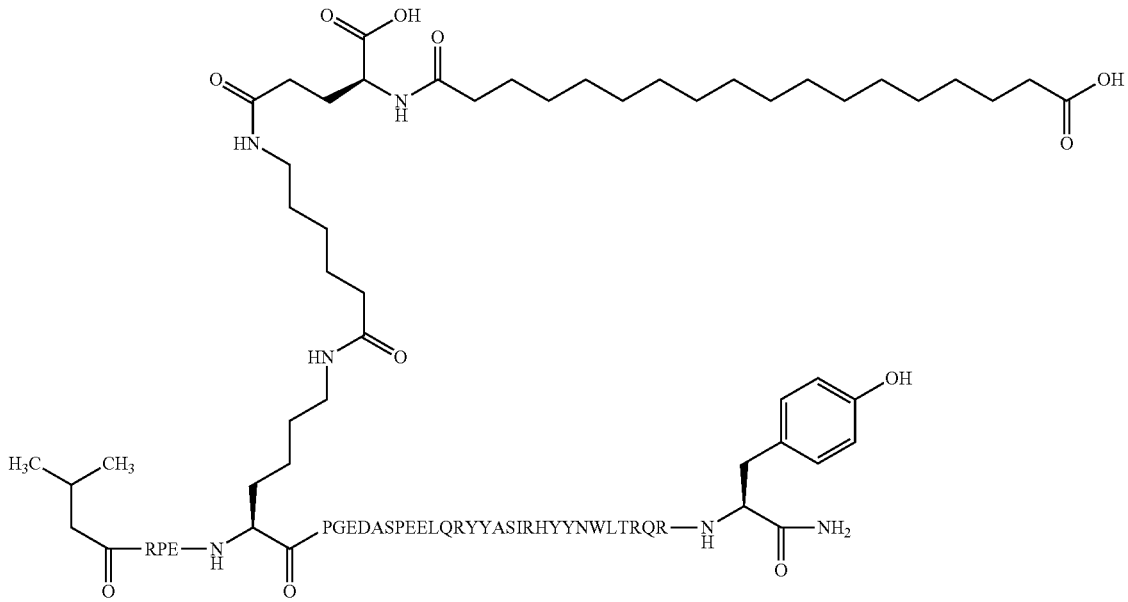

MW (average) calculated: 4795.37 g/mol.
457_LCMS01: Found [M+4H]4+: 1199.88;
The amino acid sequence of [Arg4,Lys7,Gln18,Ile24,Tyr28,Trp30,Leu31]hPYY(4-36) is given in SEQ ID NO:10.

Compound 21

N{alpha-4}-(3-Methylbutanoyl)-N{Epsilon-7}-[2-[2-[2-[[2-[2-[2-[[(4S)-4-carboxy-4-(17-carboxy-heptadecanoylamino)butanoyl]amino]ethoxy]ethoxy]acetyl]amino]ethoxy]ethoxy]acetyl]-[Arg4,Lys7,Pro9,Gln18,Tyr28,Trp30,Leu31]hPYY(4-36)

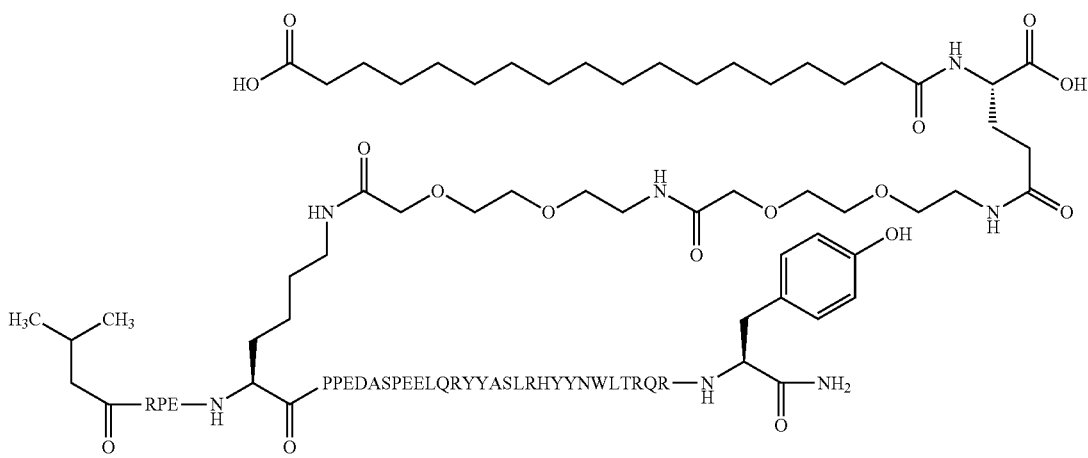

MW (average) calculated: 5012.58 g/mol.
457_LCMS01: Found [M+4H]4+: 1254.12.
The amino acid sequence of [Arg4,Lys7,Pro9,Gln18,Tyr28,Trp30,Leu31]hPYY(4-36) is given in SEQ ID NO:5.

Compound 22

N{Alpha-4}-acetyl,N{Epsilon-7}-[(4S)-4-carboxy-
4-(17-carboxyheptadecanoylamino)-butanoyl]-
[Arg4,Lys7,Gln18,Ile24,Tyr28,Trp30,Leu31]hPYY
(4-36)

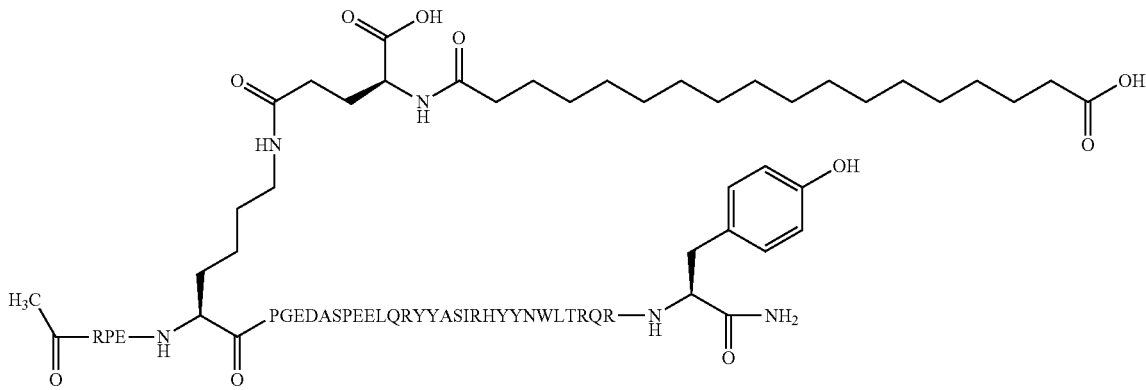

MW (average) calculated: 4640.13 g/mol.
457_LCMS01: Found [M+4H]4+: 1161.08;
The amino acid sequence of [Arg4,Lys7,Gln18,Ile24,Tyr28,Trp30,Leu31]hPYY(4-36) is given in SEQ ID NO:11.

Compound 23

N{Epsilon-7}-[(4S)-4-carboxy-4-[[(4S)-4-carboxy-
4-(17-carboxyheptadecanoylamino)-butanoyl]amino]
butanoyl]-[Arg4,Lys7,Gln18,Ile22,Trp30,Leu31]
hPYY(3-36)

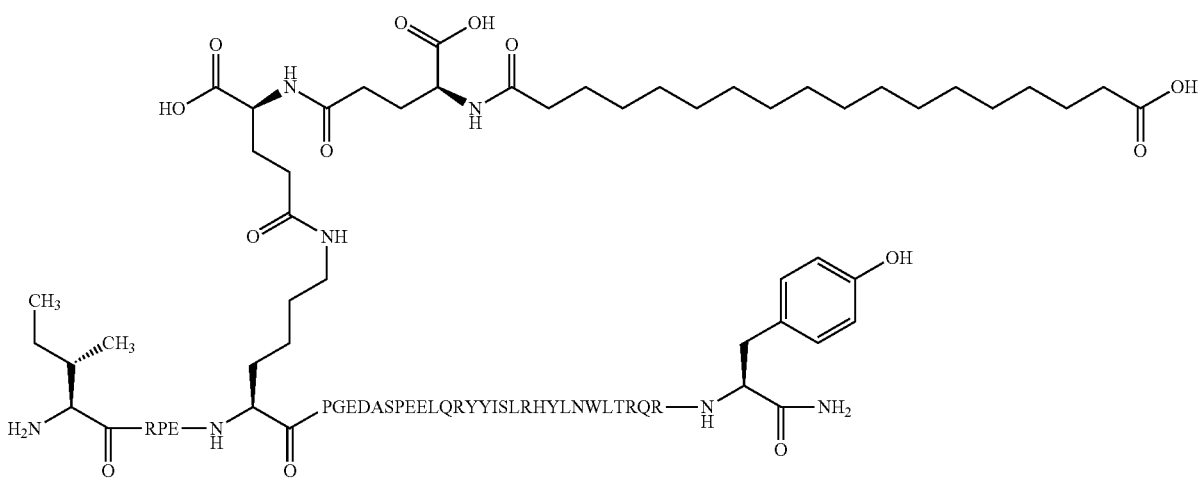

MW (average) calculated: 4832.43 g/mol.
457_LCMS01: Found [M+4H]4+: 1208.90; Found [M+5H]5+: 967.50.
The amino acid sequence of [Arg4,Lys7,Gln18,Ile22,Trp30,Leu31]hPYY(3-36) is given in SEQ ID NO:12.

Compound 24

N{Epsilon-7}-[2-[2-[2-[[2-[2-[2-[[(4S)-4-carboxy-4-(17-carboxyheptadecanoylamino)-butanoyl]amino]ethoxy]ethoxy]acetyl]amino]ethoxy]ethoxy]acetyl]-[Arg4,Lys7,Gln18, Ile22,Trp30,Leu31]hPYY(3-36)

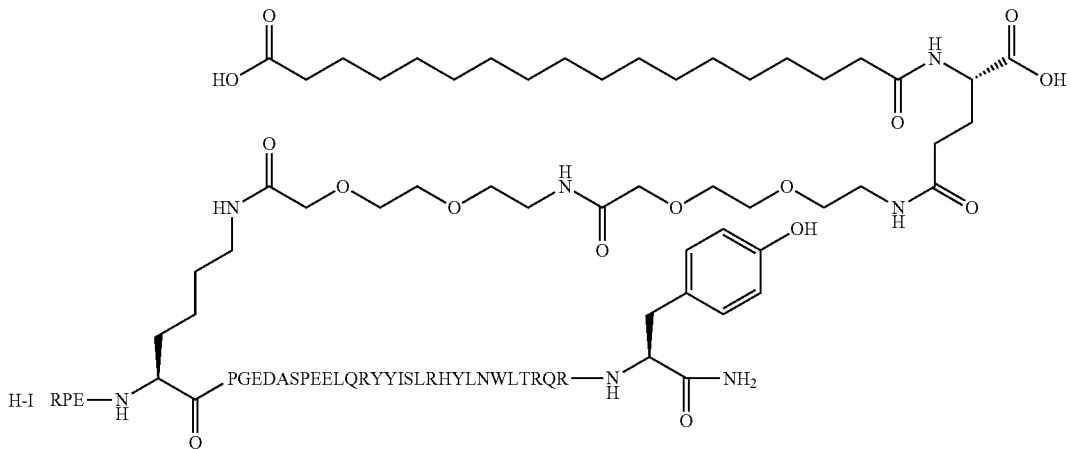

MW (average) calculated: 4993.63 g/mol.
457_LCMS01: Found [M+4H]4+: 1249.41.
The amino acid sequence of [Arg4,Lys7,Gln18,Ile22,Trp30,Leu31]hPYY(3-36) is given in SEQ ID NO:12.

Compound 25

N{alpha-4}-(3-Methylbutanoyl)-N{Epsilon-7}-[(4S)-4-carboxy-4-(17-carboxy-heptadecanoy-lamino)butanoyl]-[Arg4,Lys7,Gln18,Ile22,Trp30,Leu31]hPYY(4-36)

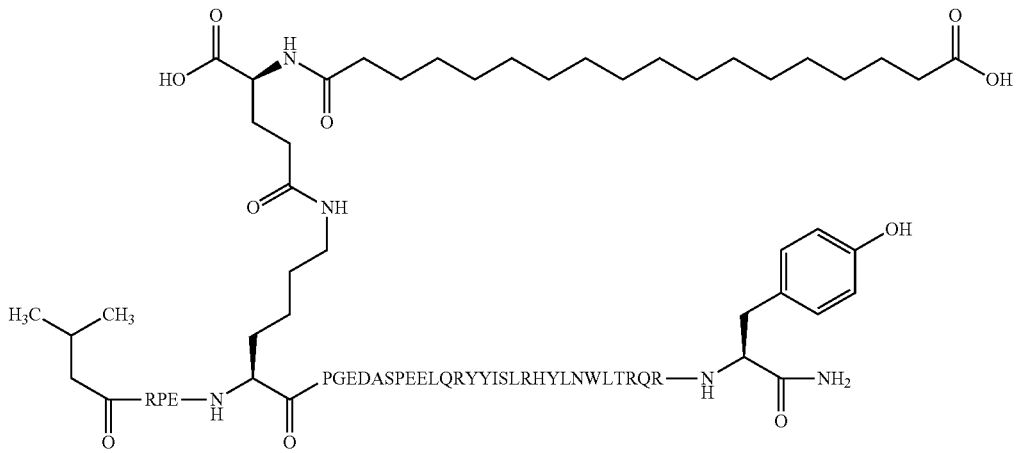

MW (average) calculated: 4674.28 g/mol.
457_LCMS01: Found [M+4H]4+: 1169.34; Found [M+5H]5+: 935.66.
The amino acid sequence of [Arg4,Lys7,Gln18,Ile22,Trp30,Leu31]hPYY(4-36) is given in SEQ ID NO:13.

Compound 26

N{alpha-4}-(3-Methylbutanoyl)-N{Epsilon-7}-[2-[2-[2-[[2-[2-[2-[[(4S)-4-carboxy-4-(17-carboxyhep-tadecanoylamino)butanoyl]amino]ethoxy]ethoxy]acetyl]amino]-ethoxy]ethoxy]acetyl]-[Arg4,Lys7,Gln18,Ile22,Trp30,Leu31]hPYY(4-36)

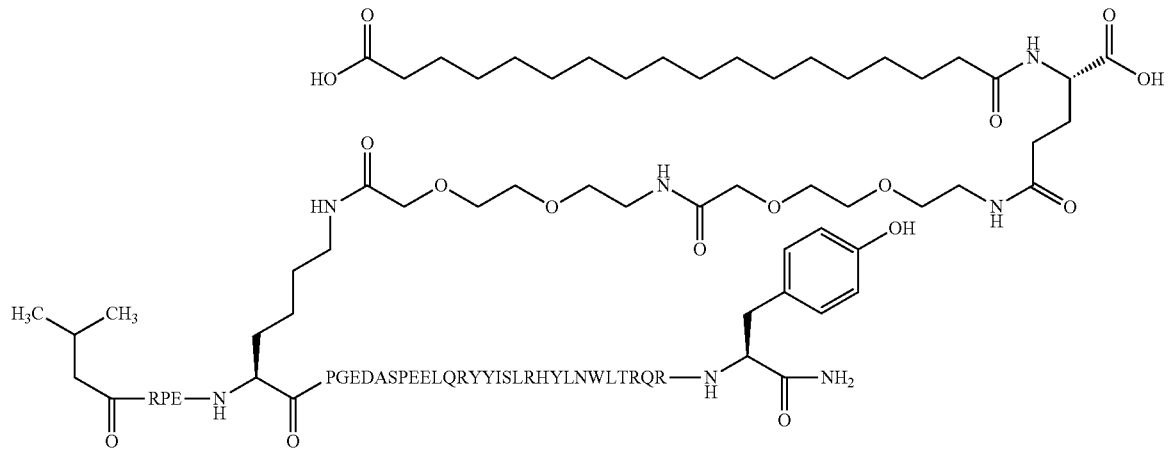

MW (average) calculated: 4964.59 g/mol.
457_LCMS01: Found [M+4H]4+: 1241.90.

The amino acid sequence of [Arg4,Lys7,Gln18,Ile22,Trp30,Leu31]hPYY(4-36) is given in SEQ ID NO:13.

Compound 27

N{alpha-4}-(3-Methylbutanoyl)-N{Epsilon-7}-[(4S)-4-carboxy-4-(17-carboxy-heptadecanoy-lamino)butanoyl]-[Arg4,Lys7,Pro9,Gln18,Ile22,Trp30,Leu31]hPYY(4-36)

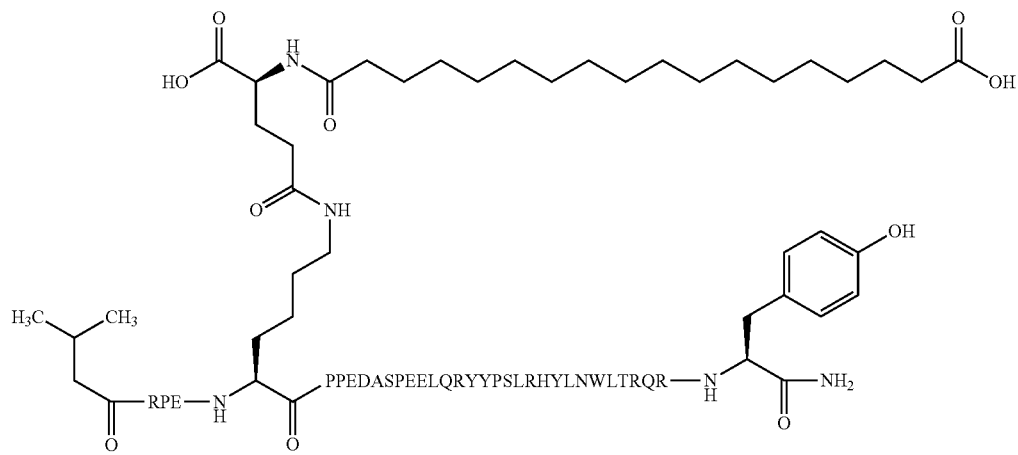

MW (average) calculated: 4714.34 g/mol.
457_LCMS01: Found [M+4H]4+: 1179.63.

The amino acid sequence of [Arg4,Lys7,Pro9,Gln18,Ile22,Trp30,Leu31]hPYY(4-36) is given in SEQ ID NO:14.

Compound 28
N{alpha-4}-(3-Methylbutanoyl)-N{Epsilon-7}-[2-[2-[2-[[2-[2-[[(4S)-4-carboxy-4-[[(4S)-4-carboxy-4-(17-carboxyheptadecanoylamino)butanoyl]amino]butanoyl]amino]-ethoxy]ethoxy]acetyl]amino]ethoxy]ethoxy]acetyl]-[Arg4,Lys7,Gln18,Ile22,Trp30, Leu31]hPYY(4-36)
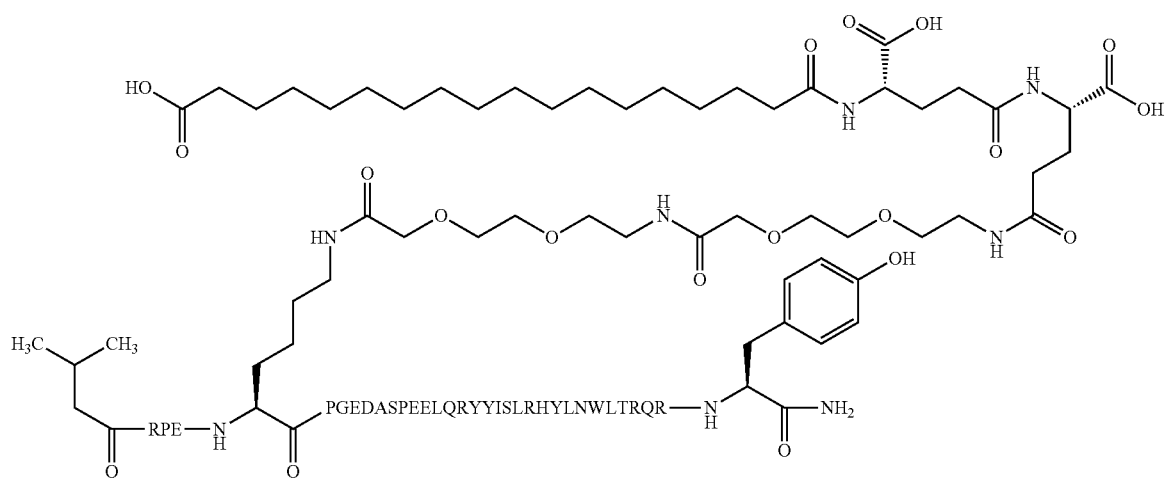
MW (average) calculated: 5093.70 g/mol.
457_LCMS01: Found [M+4H]4+: 1274.50.
The amino acid sequence of [Arg4,Lys7,Gln18,Ile22,Trp30,Leu31]hPYY(4-36) is given in SEQ ID NO:13.

Compound 29
N{alpha-4}-(3-Methylbutanoyl)-N{Epsilon-7}-[(4S)-4-carboxy-4-[[(4S)-4-carboxy-4-(17-carboxy-heptadecanoylamino)butanoyl]amino]butanoyl]-[Arg4,Lys7,Gln18,Ile22, Tyr28,Trp30,Leu31]hPYY(4-36)
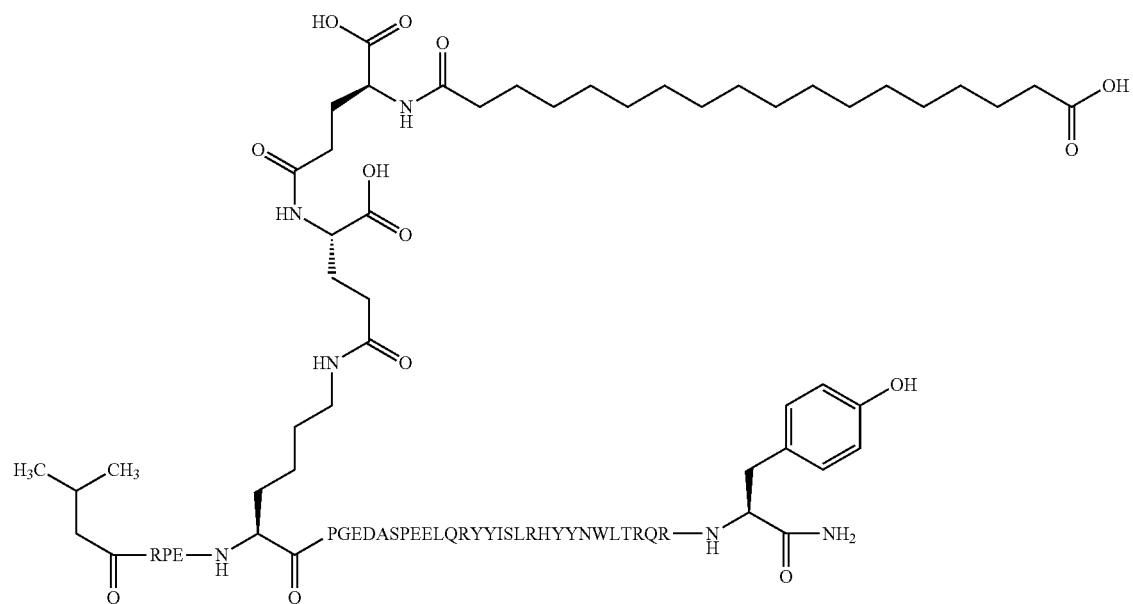
MW (average) calculated: 4853.40 g/mol.
457_LCMS01: Found [M+4H]4+: 1214.45.
The amino acid sequence of [Arg4,Lys7,Gln18,Ile22, Tyr28,Trp30,Leu31]hPYY(4-36) is given in SEQ ID NO:15.

Compound 30

N{alpha-4}-(3-Methylbutanoyl)-N{Epsilon-7}-[2-[2-[2-[[2-[2-[2-[[(4S)-4-carboxy-4-[[(4S)-4-carboxy-4-(17-carboxyheptadecanoylamino)butanoyl]amino]butanoyl]amino]-ethoxy]ethoxy]acetyl]amino]ethoxy]ethoxy]acetyl]-[Arg4,Lys7,Gln18,Ile22,Tyr28, Trp30,Leu31]hPYY(4-36)

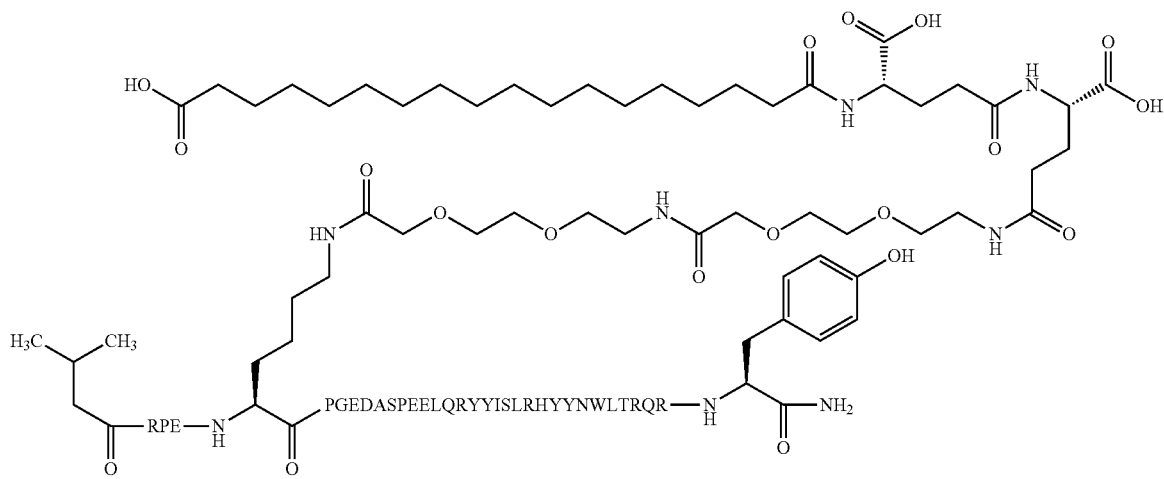

MW (average) calculated: 5143.71 g/mol.
457_LCMS01: Found [M+4H]4+: 1286.98.
The amino acid sequence of [Arg4,Lys7,Gln18,Ile22,Tyr28,Trp30,Leu31]hPYY(4-36) is given in SEQ ID NO:15.

Compound 31

N{alpha-4}-(3-Methylbutanoyl)-N{Epsilon-7}-[2-[2-[2-[[2-[2-[2-[[(4S)-4-carboxy-4-(17-carboxyheptadecanoylamino)butanoyl]amino]ethoxy]ethoxy]acetyl]-amino]ethoxy]ethoxy]acetyl]-[Arg4,Lys7,Gln18,Ile22,Tyr28,Trp30,Leu31]hPYY(4-36)

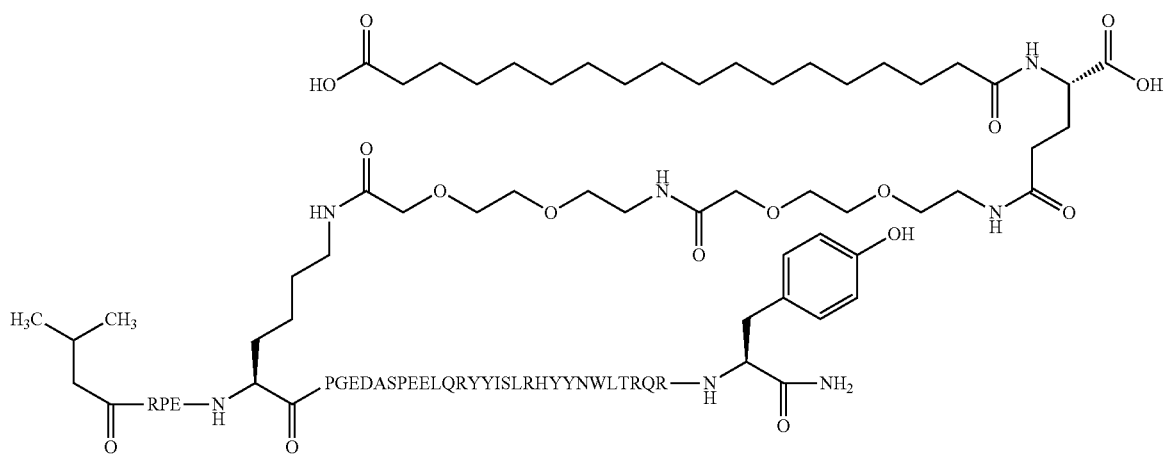

MW (average) calculated: 5014.60 g/mol.
457_LCMS01: Found [M+4H]4+: 1254.42.
The amino acid sequence of [Arg4,Lys7,Gln18,Ile22,Tyr28,Trp30,Leu31]hPYY(4-36) is given in SEQ ID NO:15.

Compound 32
N{alpha-4}-(3-Methylbutanoyl)-N{Epsilon-7}-6-
[[(4S)-4-carboxy-4-(17-carboxy-heptadecanoy-
lamino)butanoyl]amino]hexanoyl-[Arg4,Lys7,
Gln18,Ile22,Tyr28, Trp30,Leu31]hPYY(4-36)
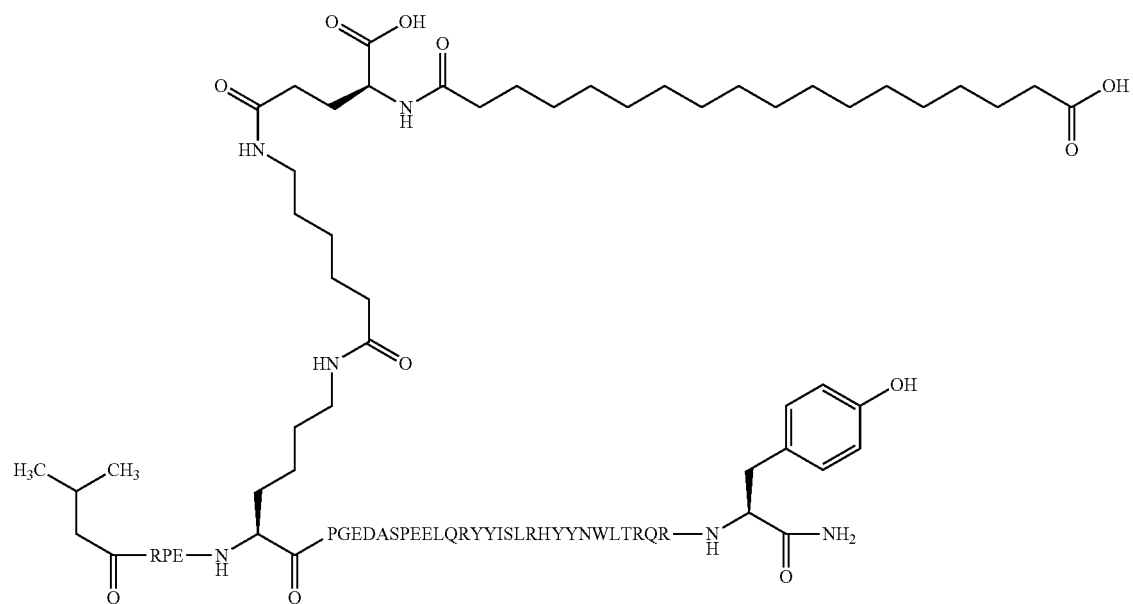
MW (average) calculated: 4837.45 g/mol.
457_LCMS01: Found [M+4H]4+: 1210.11.
The amino acid sequence of [Arg4,Lys7,Gln18,Ile22,Tyr28,Trp30,Leu31]hPYY(4-36) is given in SEQ ID NO:15.

Compound 33

N{alpha-4}-(3-Methylbutanoyl)-N{Epsilon-7}-[(4S)-4-carboxy-4-[[(4S)-4-carboxy-4-(19-carboxynonadecanoylamino)butanoyl]amino]butanoyl]-[Arg4,Lys7,Gln18, Ile22,Tyr28,Trp30,Leu31]hPYY(4-36)

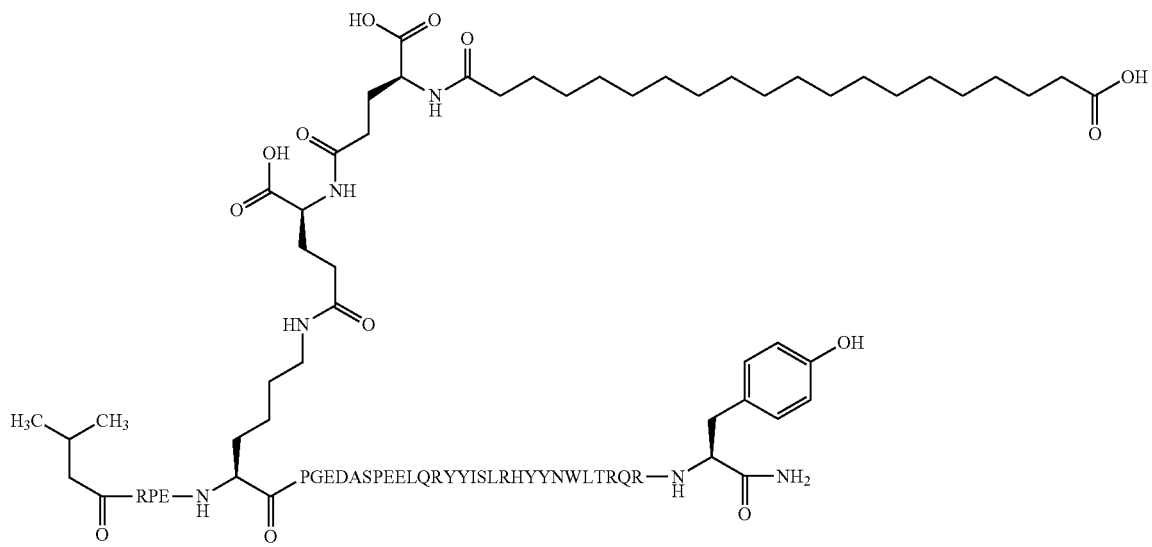

MW (average) calculated: 4881.46 g/mol.
457_LCMS01: Found [M+4H]4+: 1221.13.
The amino acid sequence of [Arg4,Lys7,Gln18,Ile22,Tyr28,Trp30,Leu31]hPYY(4-36) is given in SEQ ID NO:15.

Compound 34

N{alpha-4}-(3-Methylbutanoyl)-N{Epsilon-7}-[(4S)-4-carboxy-4-(17-carboxy-heptadecanoylamino)butanoyl]-[Arg4,Lys7,Gln18,Ile22,Ala24, Tyr28,Trp30, Leu31]hPYY(4-36)

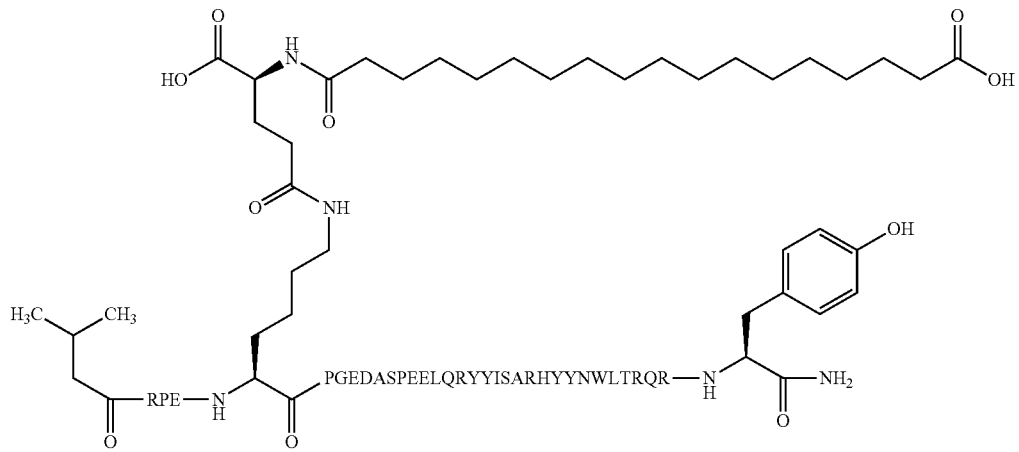

MW (average) calculated: 4682.21 g/mol.
457_LCMS01: Found [M+5H]5+: 937.4.
The amino acid sequence of [Arg4,Lys7,Gln18,Ile22, Ala24,Tyr28,Trp30,Leu31]hPYY(4-36) is given in SEQ ID NO:16.

Compound 35

N{alpha-4}-(3-Methylbutanoyl)-N{Epsilon-7}-
[(4S)-4-carboxy-4-(17-carboxy-heptadecanoy-
lamino)butanoyl]-[Arg4,Lys7,Gln18,Gln22,Tyr28,
Trp30,Leu31]hPYY(4-36)

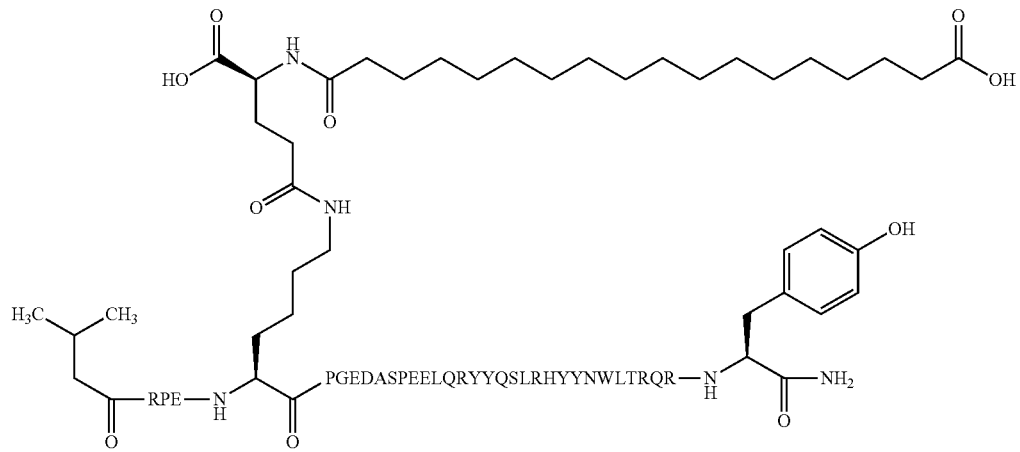

MW (average) calculated: 4739.26 g/mol.
457_LCMS01: Found [M+4H]4+: 1185.70.
The amino acid sequence of [Arg4,Lys7,Gln18,Gln22,Tyr28,Trp30,Leu31]hPYY(4-36) is given in SEQ ID NO:17.

Compound 36

N{alpha-4}-(3-Methylbutanoyl)-N{Epsilon-7}-[2-
[2-[2-[[2-[2-[2-[[(4S)-4-carboxy-4-(17-carboxyhep-
tadecanoylamino)butanoyl]amino]ethoxy]ethoxy]
acetyl]-amino]ethoxy]ethoxy]acetyl]-[Arg4,Lys7,
Gln18,Gln22,Tyr28,Trp30,Leu31]hPYY(4-36)

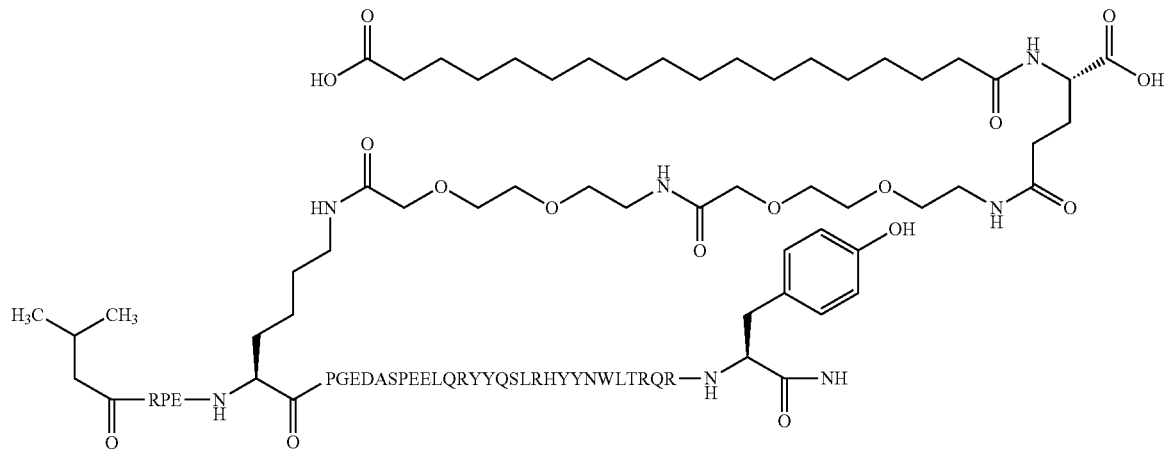

MW (average) calculated: 5029.57 g/mol.
457_LCMS01: Found [M+4H]4+: 1258.45.
The amino acid sequence of [Arg4,Lys7,Gln18,Gln22,Tyr28,Trp30,Leu31]hPYY(4-36) is given in SEQ ID NO:17.

Compound 37

N{alpha-4}-(3-Methylbutanoyl)-N{Epsilon-7}-[2-[2-[2-[[2-[2-[2-[[(4S)-4-carboxy-4-[[(4S)-4-carboxy-4-(17-carboxyheptadecanoylamino)butanoyl]amino]butanoyl]amino]-ethoxy]ethoxy]acetyl]amino]ethoxy]ethoxy]acetyl]-[Arg4,Lys7,Gln18,Gln22,Tyr28, Trp30,Leu31]hPYY(4-36)

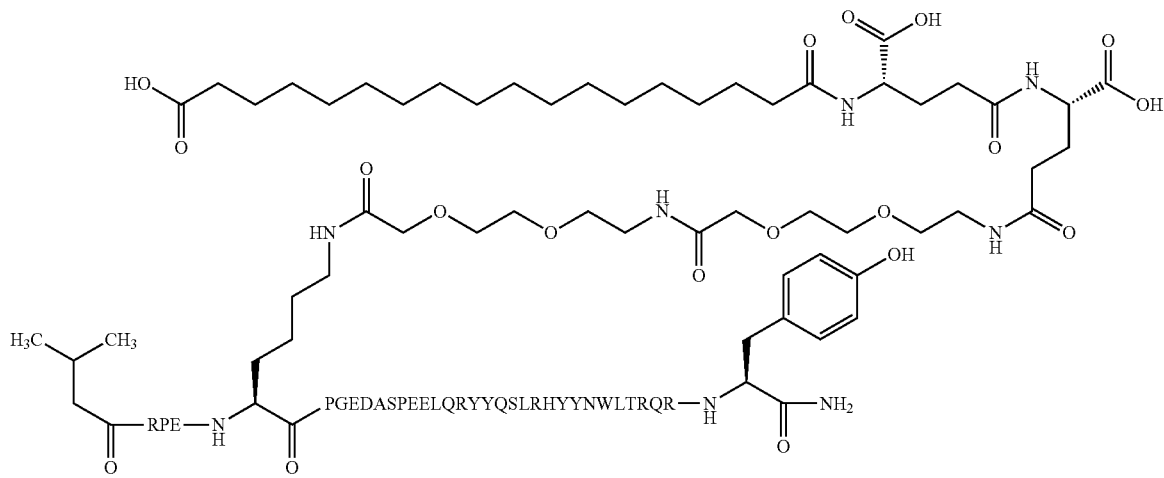

MW (average) calculated: 5158.68 g/mol.
457_LCMS01: Found [M+4H]4+: 1290.62.
The amino acid sequence of [Arg4,Lys7,Gln18,Gln22,Tyr28,Trp30,Leu31]hPYY(4-36) is given in SEQ ID NO:17.

Compound 38

N{alpha-4}-(3-Methylbutanoyl)-N{Epsilon-7}-[2-[2-[2-[[2-[2-[2-[[(4S)-4-carboxy-4-(17-carboxyheptadecanoylamino)butanoyl]amino]ethoxy]ethoxy]acetyl]amino]-ethoxy]ethoxy]acetyl]-[Arg4,Lys7,Gln18,Val22,Tyr28,Trp30,Leu31]hPYY(4-36)

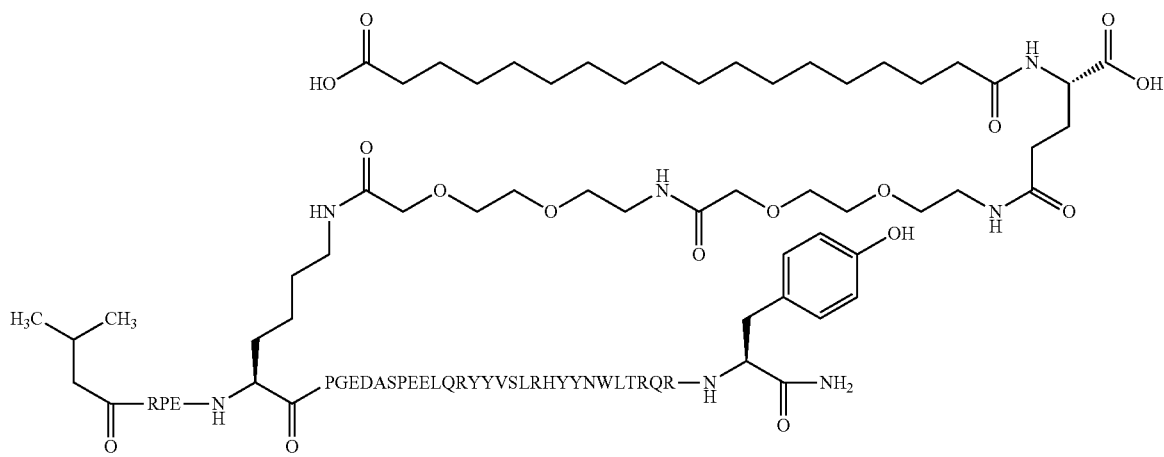

MW (average) calculated: 5000.58 g/mol.
457_LCMS01: Found [M+4H]4+: 1251.20.
The amino acid sequence of [Arg4,Lys7,Gln18,Val22,Tyr28,Trp30,Leu31]hPYY(4-36) is given in SEQ ID NO:18.

Compound 39

N{alpha-4}-(3-Methylbutanoyl)-N{Epsilon-7}-[2-
[2-[2-[[2-[2-[2-[[(4S)-4-carboxy-4-[[(4S)-4-carboxy-
4-(17-carboxyheptadecanoylamino)butanoyl]amino]
butanoyl]-amino]ethoxy]ethoxy]acetyl]amino]
ethoxy]ethoxy]acetyl]-[Arg4,Lys7,Gln18,Val22,
Tyr28,Trp30,Leu31]hPYY(4-36)

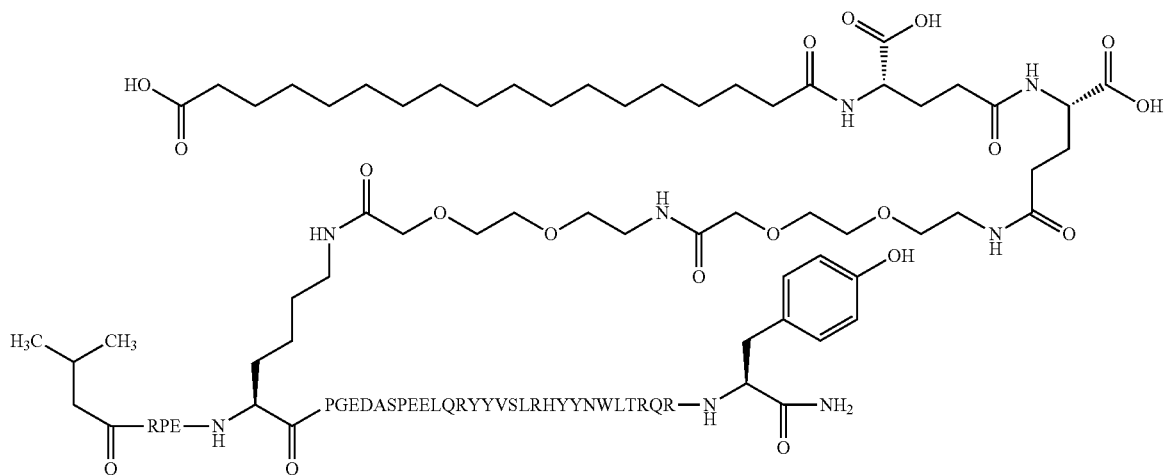

MW (average) calculated: 5129.69 g/mol.
457_LCMS01: Found [M+4H]4+: 1283.37.
The amino acid sequence of [Arg4,Lys7,Gln18,Val22,
Tyr28,Trp30,Leu31]hPYY(4-36) is given in SEQ ID NO:18.

Compound 40

N{alpha-4}-(3-Methylbutanoyl)-N{Epsilon-7}-
[(4S)-4-carboxy-4-(17-carboxy-heptadecanoy-
lamino)butanoyl]-[Arg4,Lys7,Gln18,Val22,Tyr28,
Trp30,Leu31]hPYY(4-36)

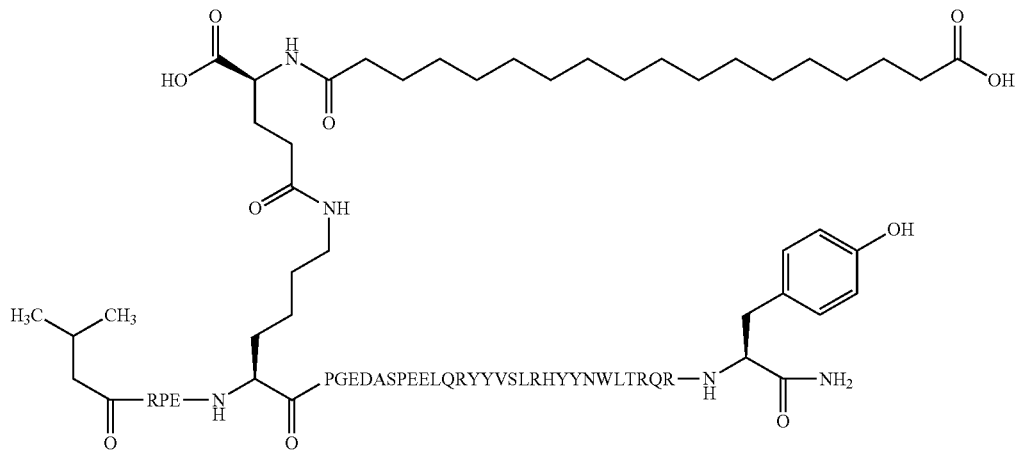

MW (average) calculated: 4710.26 g/mol.
457_LCMS01: Found [M+4H]4+: 1178.49.
The amino acid sequence of [Arg4,Lys7,Gln18,Val22,
Tyr28,Trp30,Leu31]hPYY(4-36) is given in SEQ ID NO:18.

Compound 41

N{alpha-4}-(3-Methylbutanoyl)-(N{Epsilon-7}-
[(4S)-4-carboxy-4-[[(4S)-4-carboxy-4-(17-carboxy-
heptadecanoylamino)butanoyl]amino]butanoyl]-
[Arg4,Lys7,Gln18,Val22, Tyr28,Trp30,Leu31]hPYY
(4-36)

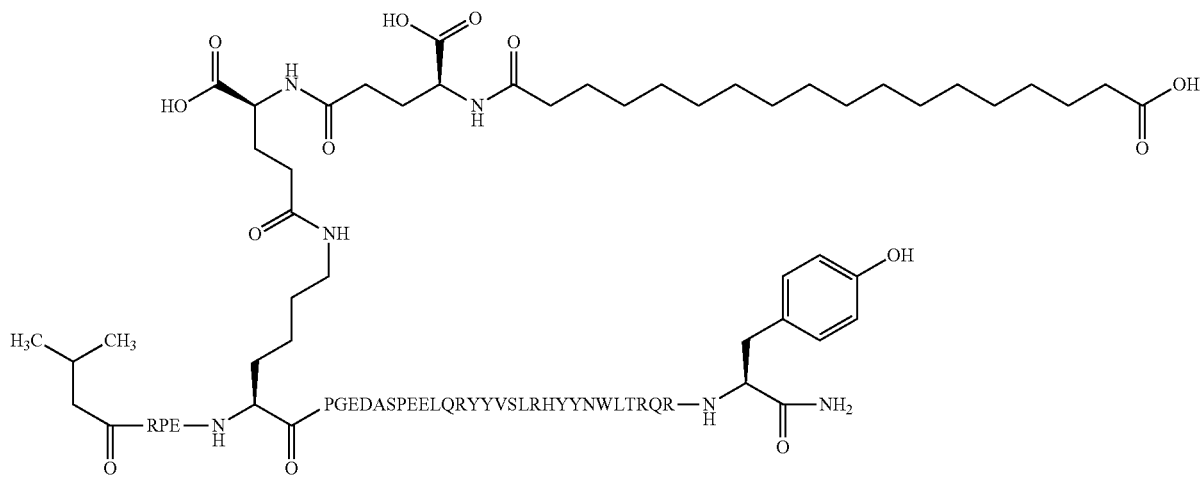

MW (average) calculated: 4839.38 g/mol.
457_LCMS01: Found [M+4H]4+: 1210.80.
The amino acid sequence of [Arg4,Lys7,Gln18,Val22,Tyr28,Trp30,Leu31]hPYY(4-36) is given in SEQ ID NO:18.

Compound 42

N{alpha-4}-(3-Methylbutanoyl)-N{Epsilon-7}-
[(4S)-4-carboxy-4-(17-carboxy-heptadecanoy-
lamino)butanoyl]-[Arg4,Lys7,Thr9,Gln18,Tyr28,
Trp30,Leu31]hPYY(4-36)

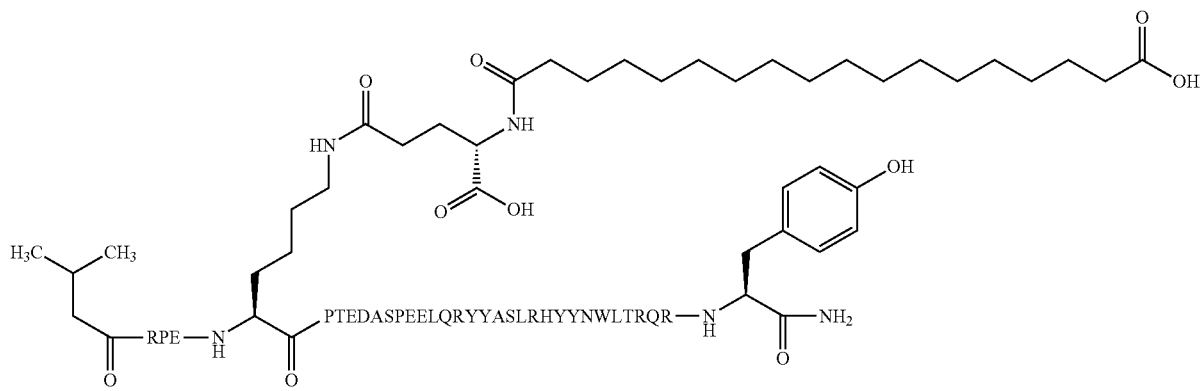

MW (average) calculated: 4726.26 g/mol.
457_LCMS01: Found [M+4H]4+: 1182.59.
The amino acid sequence of [Arg4,Lys7,Thr9,Gln18,Tyr28,Trp30,Leu31]hPYY(4-36) is given in SEQ ID NO:7.

Compound 43

N{alpha-4}-(3-Methylbutanoyl)-N{Epsilon-7}-[(4S)-4-carboxy-4-(17-carboxy-heptadecanoylamino)butanoyl]-[Arg4,Lys7,Thr9,Gln18,Gln22,Tyr28,Trp30,Leu31]hPYY(4-36)

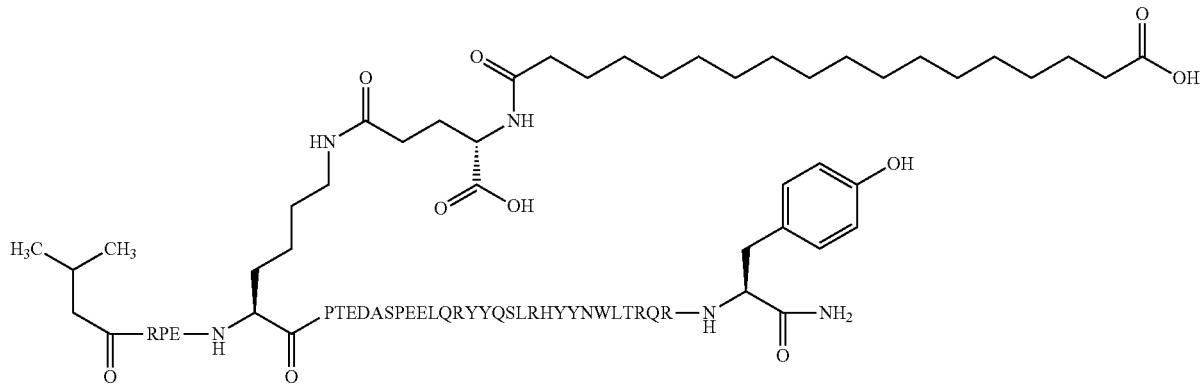

MW (average) calculated: 4783.31 g/mol.
457_LCMS01: Found [M+4H]4+: 1196.87.

The amino acid sequence of [Arg4,Lys7,Thr9,Gln18,Gln22,Tyr28,Trp30,Leu31]hPYY(4-36) is given in SEQ ID NO:19.

Compound 44

N{alpha-4}-(3-Methylbutanoyl)-N{Epsilon-7}-[(4S)-4-carboxy-4-(17-carboxy-heptadecanoylamino)butanoyl]-[Arg4,Lys7,Thr9,Gln18,Val22,Tyr28,Trp30,Leu31]hPYY(4-36)

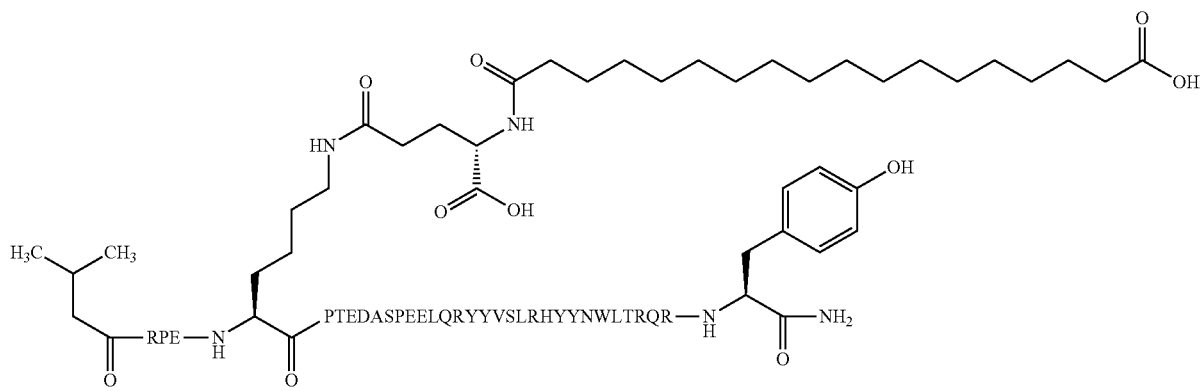

MW (average) calculated: 4754.32 g/mol.
457_LCMS01: Found [M+4H]4+: 1189.59.

The amino acid sequence of [Arg4,Lys7,Thr9,Gln18,Val22,Tyr28,Trp30,Leu31]hPYY(4-36) is given in SEQ ID NO:20.

Compound 45

N{alpha-4}-(3-Methylbutanoyl)-N{Epsilon-7}-
[(4S)-4-carboxy-4-(17-carboxy-heptadecanoy-
lamino)butanoyl]-[Arg4,Lys7,Thr13,Gln18,Gln22,
Tyr28, Trp30,Leu31]hPYY(4-36)

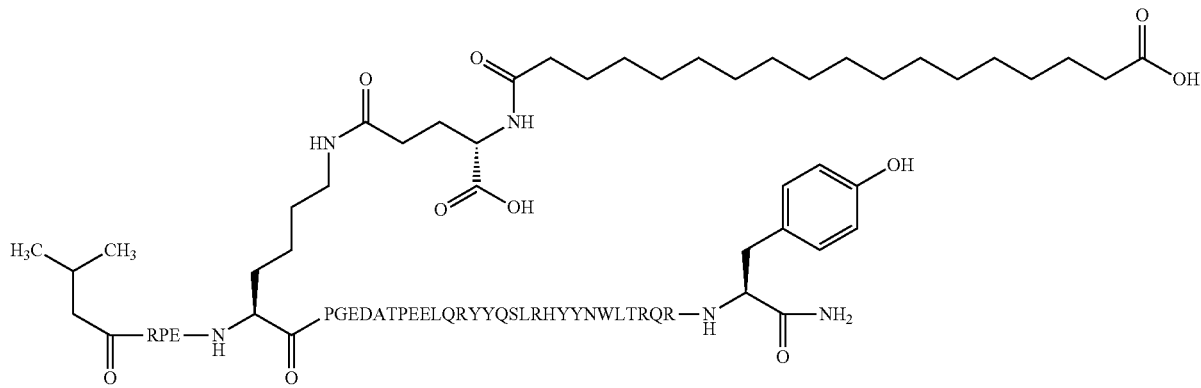

MW (average) calculated: 4753.29 g/mol.
457_LCMS01: Found [M+4H]4+: 1189.35.
The amino acid sequence of [Arg4,Lys7,Thr13,Gln18,Gln22,Tyr28,Trp30,Leu31]hPYY(4-36) is given in SEQ ID NO:21.

Compound 46

N{alpha-4}-(3-Methylbutanoyl)-N{Epsilon-7}-[2-
[2-[2-[[2-[2-[[(4S)-4-carboxy-4-(17-carboxyhep-
tadecanoylamino)butanoyl]amino]ethoxy]ethoxy]
acetyl]-amino]-ethoxy]ethoxy]acetyl]-[Arg4,Lys7,
Thr13,Gln18,Val22,Tyr28,Trp30,Leu31]hPYY(4-36)

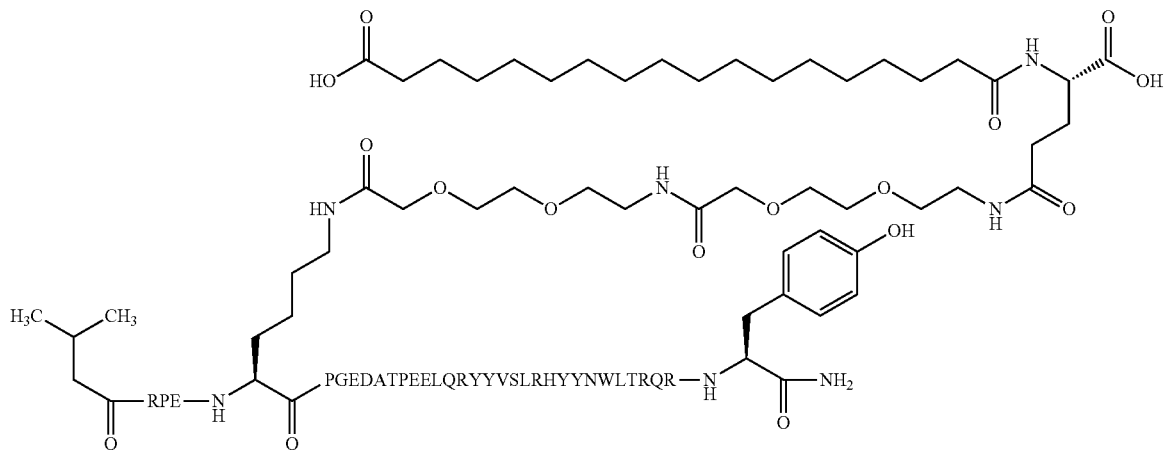

MW (average) calculated: 5014.60 g/mol.
457_LCMS01: Found [M+4H]4+: 1254.56.
The amino acid sequence of [Arg4,Lys7,Thr13,Gln18,Val22,Tyr28,Trp30,Leu31]hPYY(4-36) is given in SEQ ID NO:22.

Compound 47

N{alpha-4}-(3-Methylbutanoyl)-N{Epsilon-7}-
[(4S)-4-carboxy-4-(17-carboxy-heptadecanoy-
lamino)butanoyl]-[Arg4,Lys7,Thr13,Gln18,Val22,
Tyr28, Trp30,Leu31]hPYY(4-36)

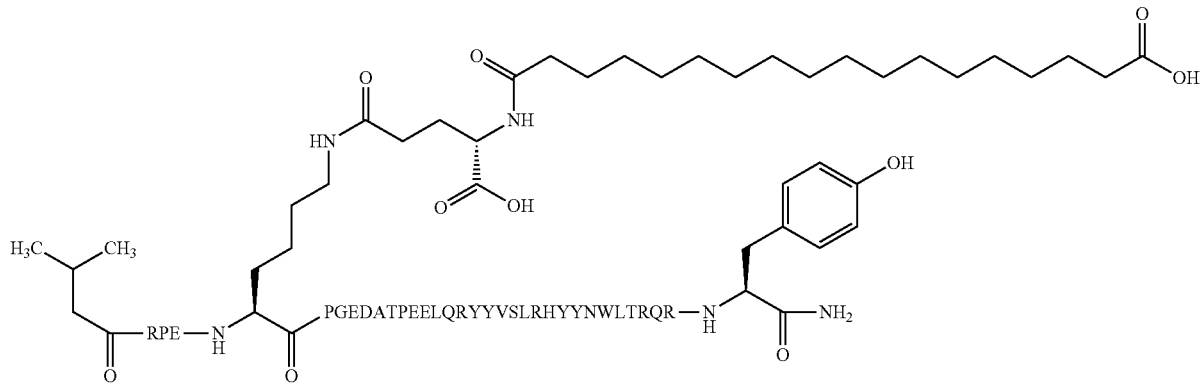

MW (average) calculated: 4724.29 g/mol.
457_LCMS01: Found [M+4H]4+: 1182.1.
The amino acid sequence of [Arg4,Lys7,Thr13,Gln18, Val22,Tyr28,Trp30,Leu31]hPYY(4-36) is given in SEQ ID NO:22.

Compound 48

N{alpha-4}-(3-Methylbutanoyl)-N{Epsilon-7}-
[(4S)-4-carboxy-4-(19-carboxy-nonadecanoylamino)
butanoyl]-[Arg4,Lys7,Gln18,Tyr28,Trp30,Leu31]
hPYY(4-36)

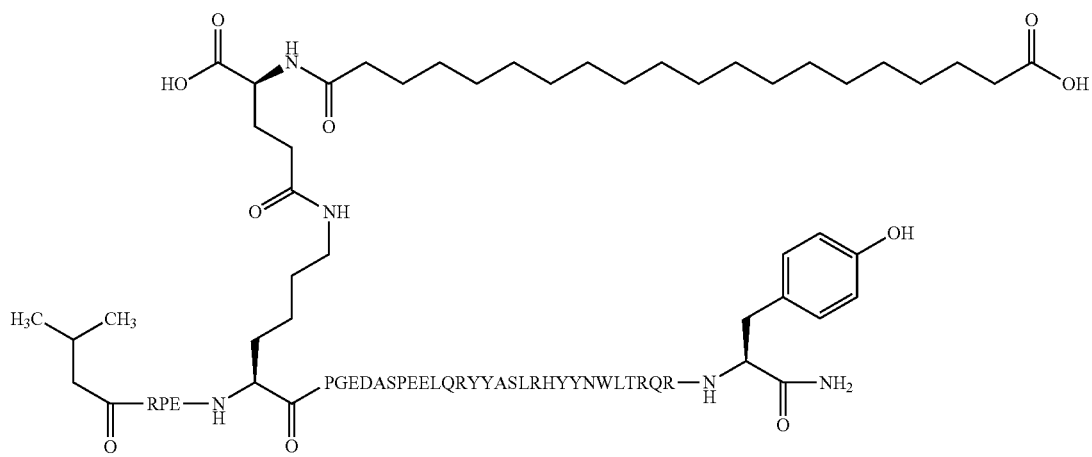

MW (average) calculated: 4710.26 g/mol.
457_LCMS01: Found [M+4H]4+: 1178.36; [M+5H]5+: 942.89.
The amino acid sequence of [Arg4,Lys7,Gln18,Tyr28, Trp30,Leu31]hPYY(4-36) is given in SEQ ID NO:4.

Compound 49

N{alpha-4}-(3-Methylbutanoyl)-N{Epsilon-7}-
[(4S)-4-carboxy-4-(17-carboxy-heptadecanoy-
lamino)butanoyl]-[Arg4,Lys7,Gln18,Ile22,Tyr28,
Trp30,Leu31]hPYY(4-36)

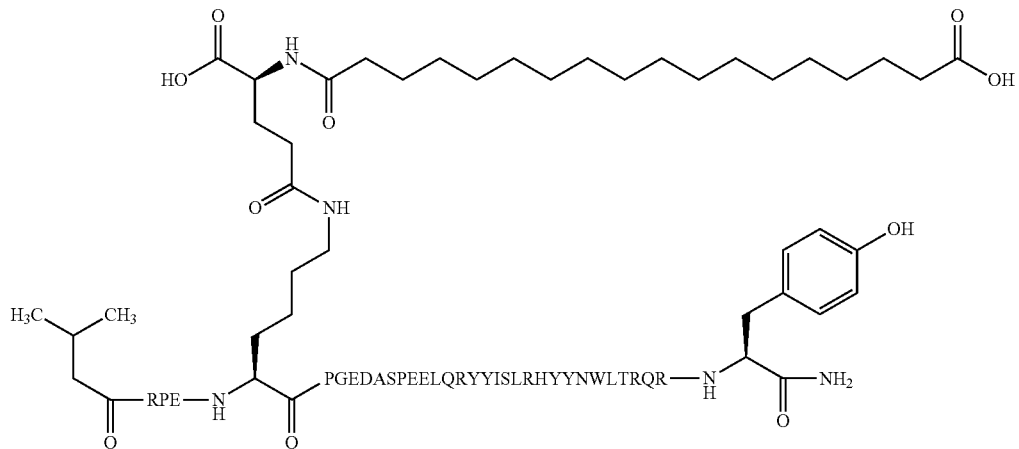

MW (average) calculated: 4724.29 g/mol.
457_LCMS01: Found [M+4H]4+: 1182.10.
The amino acid sequence of [Arg4,Lys7,Gln18,Ile22, Tyr28,Trp30,Leu31]hPYY(4-36) is given in SEQ ID NO:15.

Compound 50

N{alpha-4}-(3-Methylbutanoyl)-N{Epsilon-10}-
[(4S)-4-carboxy-4-[[2-[2-[2-[[(4S)-4-carboxy-4-(17-
carboxyheptadecanoylamino)butanoyl]amino]
ethoxy]ethoxy]-acetyl]amino]butanoyl]-[Arg4,
Lys10,Gln18,Glu22,Tyr28,Trp30,Leu31]-PYY(4-36)

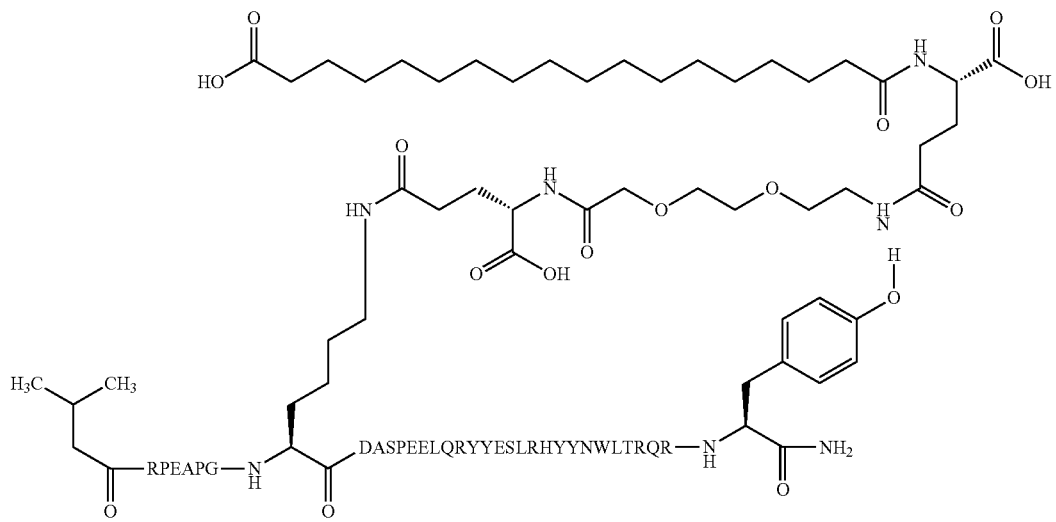

MW (average) calculated: 4956.48 g/mol.
457_LCMS01: Found [M+4H]4+: 1240.39.
The amino acid sequence of [Arg4,Lys10,Gln18,Glu22, Tyr28,Trp30,Leu31]-PYY(4-36) is given in SEQ ID NO:23.

Compound 51

N{alpha-4}-(3-Methylbutanoyl)-N{Epsilon-10}-[2-[2-[2-[[2-[2-[2-[[(4S)-4-carboxy-4-(17-carboxyheptadecanoylamino)butanoyl]amino]ethoxy]ethoxy]acetyl]-amino]ethoxy]ethoxy]acetyl]-[Arg4,Lys10,Gln18,Glu22,Tyr28,Trp30,Leu31]-PYY(4-36)

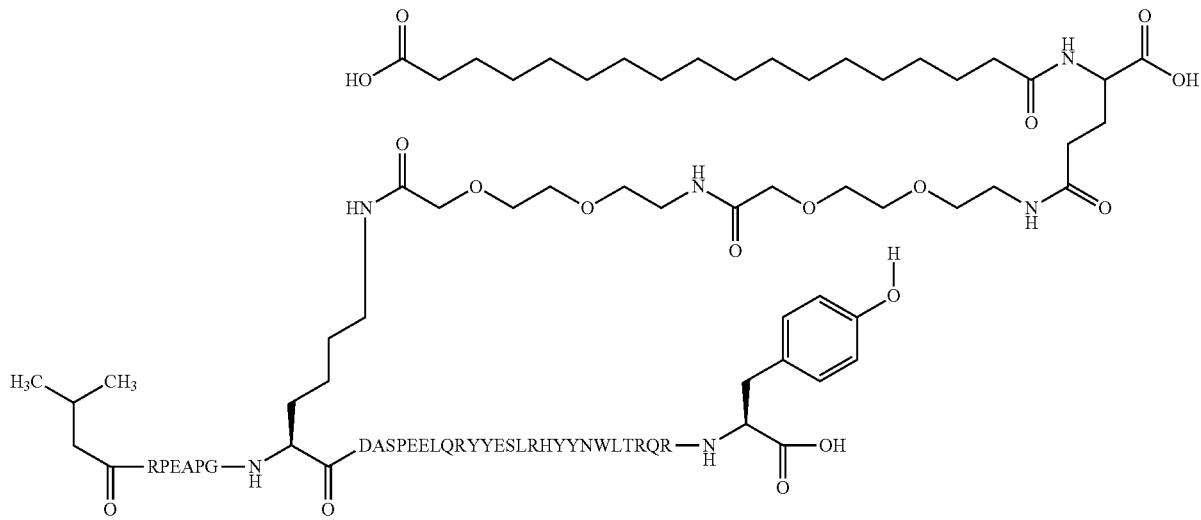

MW (average) calculated: 4973.51 g/mol.
457_LCMS01: Found [M+4H]4+: 1244.34 [M+5H]5+: 995.3.
The amino acid sequence of [Arg4,Lys10,Gln18,Glu22,Tyr28,Trp30,Leu31]-PYY(4-36) is given in SEQ ID NO:23.

Compound 52

N{alpha-4}-(3-Methylbutanoyl)-N{Epsilon-10}-[2-[2-[2-[[2-[2-[2-[[(4S)-4-carboxy-4-(17-carboxyheptadecanoylamino)butanoyl]amino]ethoxy]ethoxy]acetyl]amino]-ethoxy]ethoxy]acetyl]-[Arg4,Lys10,Gln18,Glu23,Tyr28,Trp30,Leu31]-PYY(4-36)

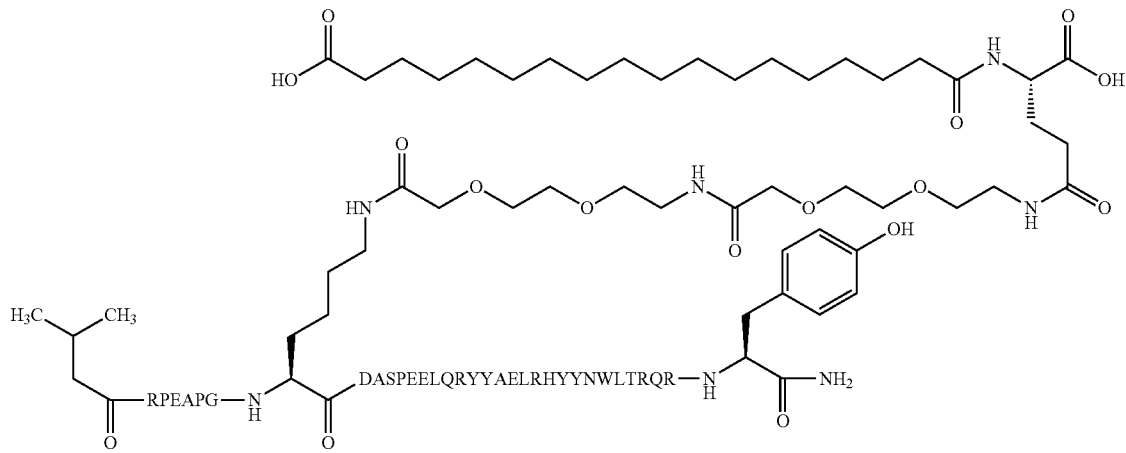

MW (average) calculated: 4956.52 g/mol.
457_LCMS01: Found [M+3H]3+: 1653.21 [M+4H]4+: 1240.16.
The amino acid sequence of Arg4,Lys10,Gln18,Glu23,Tyr28,Trp30,Leu31]-PYY(4-36) is given in SEQ ID NO:24.

Compound 53

N{alpha-4}-(3-Methylbutanoyl)-N{Epsilon-10}-[(4S)-4-carboxy-4-[[2-[2-[2-[[(4S)-4-carboxy-4-(17-carboxyheptadecanoylamino)butanoyl]amino]ethoxy]ethoxy]-acetyl]amino]butanoyl]-[Arg4,Lys10,Gln18,Glu23,Tyr28,Trp30,Leu31]-PYY(4-36)

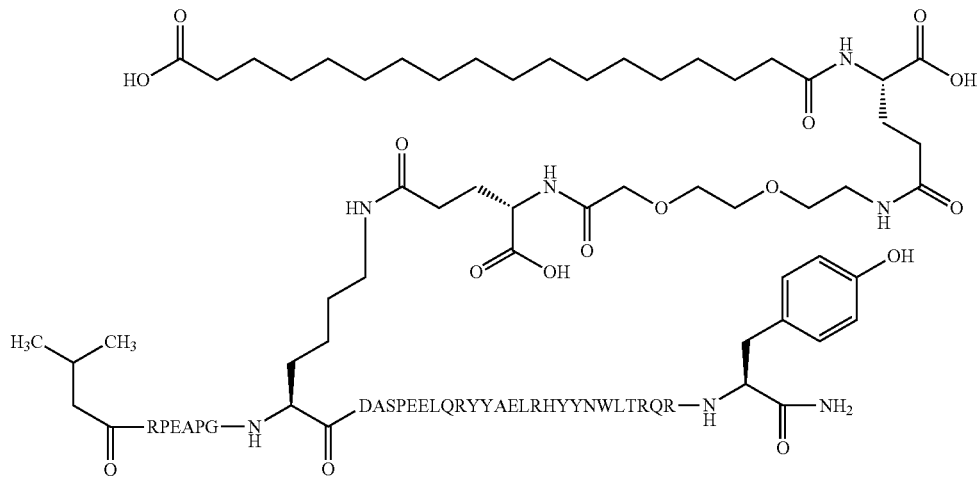

MW (average) calculated: 4940.48 g/mol.
457_LCMS01: Found [M+3H]3+: 1647.85; [M+4H]4+: 1236.14; [M+5H]5+: 989.11.

The amino acid sequence of [Arg4,Lys10,Gln18,Glu23,Tyr28,Trp30,Leu31]-PYY(4-36) is given in SEQ ID NO:24.

Compound 54

N{alpha-4}-(3-Methylbutanoyl)-N{Epsilon-10}-[(4S)-4-carboxy-4-[[2-[2-[2-[[(4S)-4-carboxy-4-(17-carboxyheptadecanoylamino)butanoyl]amino]ethoxy]ethoxy]-acetyl]amino]butanoyl]-[Arg4,Pro9,Lys10,Gln18,Glu22,Tyr28,Trp30,Leu31]-PYY(4-36)

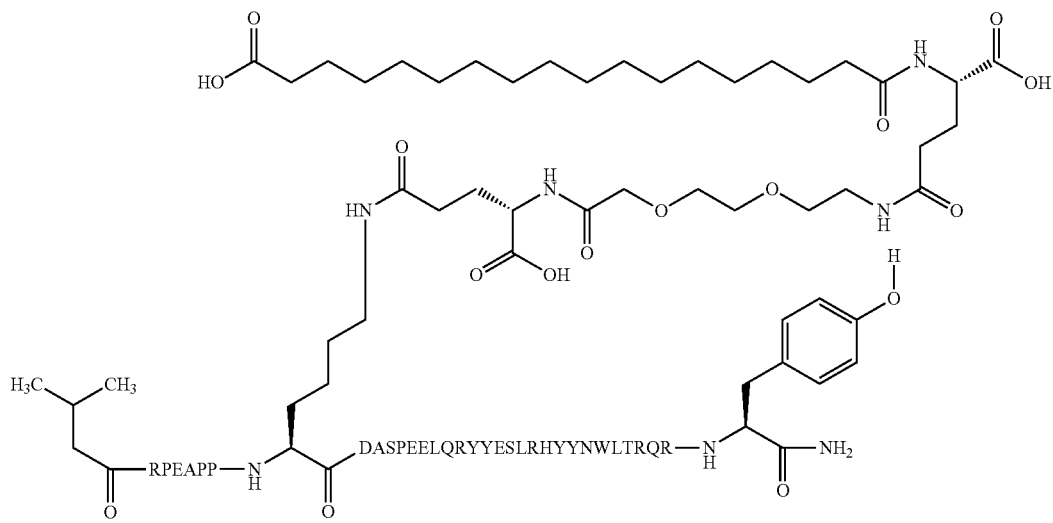

MW (average) calculated: 4996.54 g/mol.
457_LCMS01: Found [M+4H]4+: 1249.9; [M+5H]5+: 1000.1.

The amino acid sequence of [Arg4,Pro9,Lys10,Gln18,Glu22,Tyr28,Trp30,Leu31]-PYY(4-36) is given in SEQ ID NO:25.

Compound 55

N{alpha-4}-(3-Methylbutanoyl)-N{Epsilon-7}-[(4S)-4-carboxy-4-(16-sulfohexadecanoylamino)butanoyl]-[Arg4,Lys7,Gln18,Tyr28,Trp30,Leu31]-PYY(4-36)

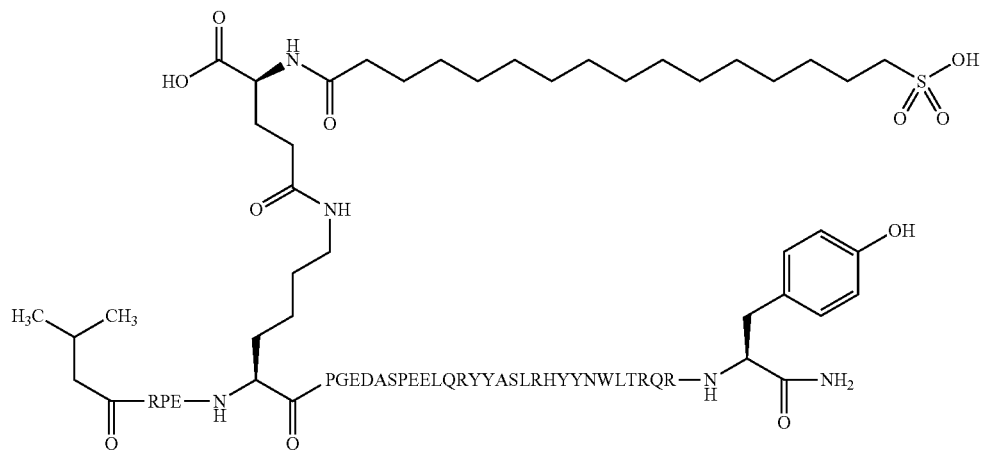

MW (average) calculated: 4704.24 g/mol.
457_LCMS01: Found [M+4H]4+: 1177.09.

The amino acid sequence of [Arg4,Lys7,Gln18,Tyr28,Trp30,Leu31]-PYY(4-36) is given in SEQ ID NO:4.

Compound 56

N{alpha-4}-(3-Methylbutanoyl)-N{Epsilon-10}-[(4S)-4-carboxy-4-[[2-[2-[2-[[(4S)-4-carboxy-4-(17-carboxyheptadecanoylamino)butanoyl]amino]ethoxy]ethoxy]-acetyl]amino]butanoyl]-[Arg4,Pro9,Lys10,Gln18,Tyr28,Trp30,Leu31]-PYY(4-36)

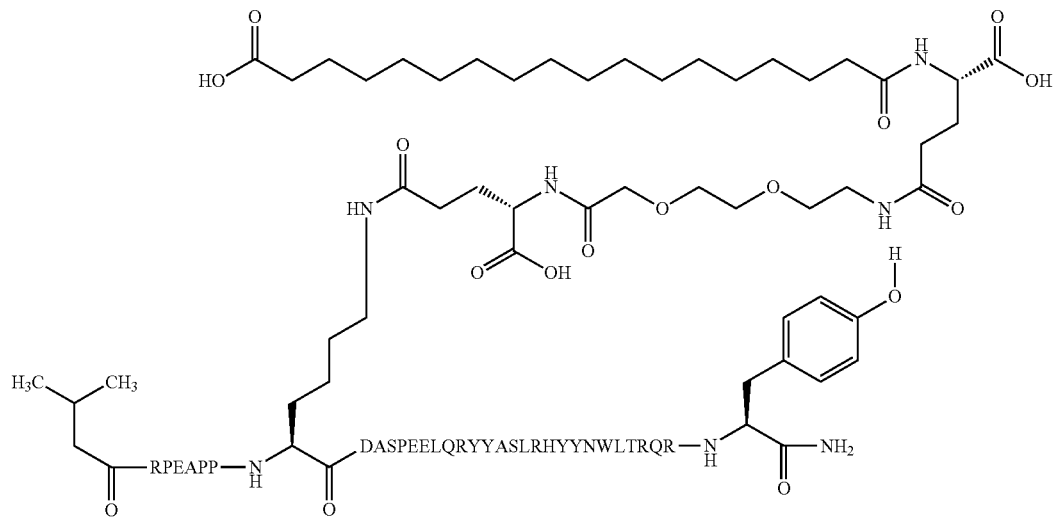

MW (average) calculated: 4938.51 g/mol.
457_LCMS01: Found [M+4H]4+: 1235.38; [M+5H]5+: 988.72.

The amino acid sequence of [Arg4,Pro9,Lys10,Gln18,Tyr28,Trp30,Leu31]-PYY(4-36) is given in SEQ ID NO:26.

Compound 57

N{alpha-4}-(3-Methylbutanoyl)-N{Epsilon-7}-[2-[2-[2-[[(4S)-4-carboxy-4-(17-carboxyheptadecanoy-lamino)butanoyl]amino]ethoxy]ethoxy]acetyl]-[Arg4,Lys7,Gln18,Val22,Tyr28,Trp30,Leu31]-PYY(4-36)

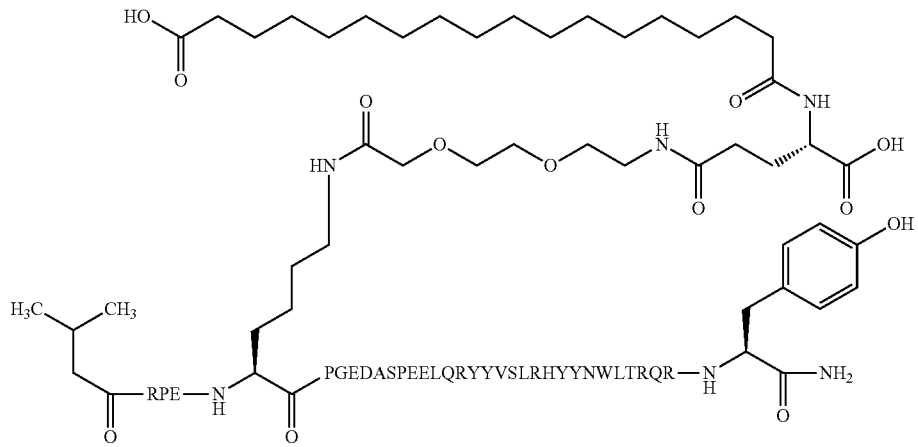

MW (average) calculated: 4855.42 g/mol.
457_LCMS01: Found [M+3H]3+: 1619.50; [M+4H]4+: 1214.88; [M+5H]5+: 972.10.
The amino acid sequence of [Arg4,Lys7,Gln18,Val22,Tyr28,Trp30,Leu31]-PYY(4-36) is given in SEQ ID NO:18.

Compound 58

N{alpha-4}-(3-Methylbutanoyl)-N{Epsilon-7}-[2-[2-[2-[[(4S)-4-carboxy-4-(15-carboxypentadecanoy-lamino)butanoyl]amino]ethoxy]ethoxy]acetyl]-[Arg4,Lys7,Gln18,Tyr28,Trp30,Leu31]-PYY(4-36)

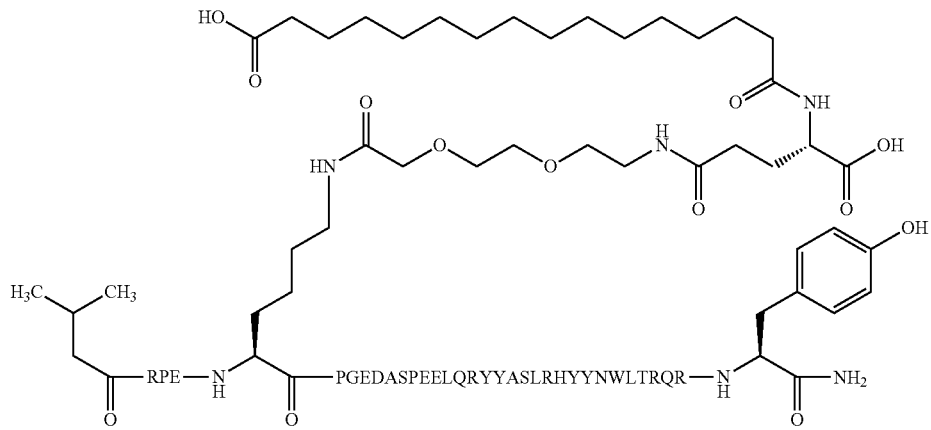

MW (average) calculated: 4799.31 g/mol.
457_LCMS01: Found [M+4H]4+: 1200.70; [M+5H]5+: 960.76.
The amino acid sequence of [Arg4,Lys7,Gln18,Tyr28,Trp30,Leu31]-PYY(4-36) is given in SEQ ID NO:4.

Compound 59

N{alpha-4}-(3-Methylbutanoyl)-N{Epsilon-10}-
[(4S)-4-carboxy-4-[[2-[2-[2-[[(4S)-4-carboxy-4-(17-
carboxyheptadecanoylamino)butanoyl]amino]
ethoxy]ethoxy]-acetyl]amino]butanoyl]-[Arg4,
Lys10,Gln18,Tyr28,Trp30,Leu31]-PYY-(4-36)

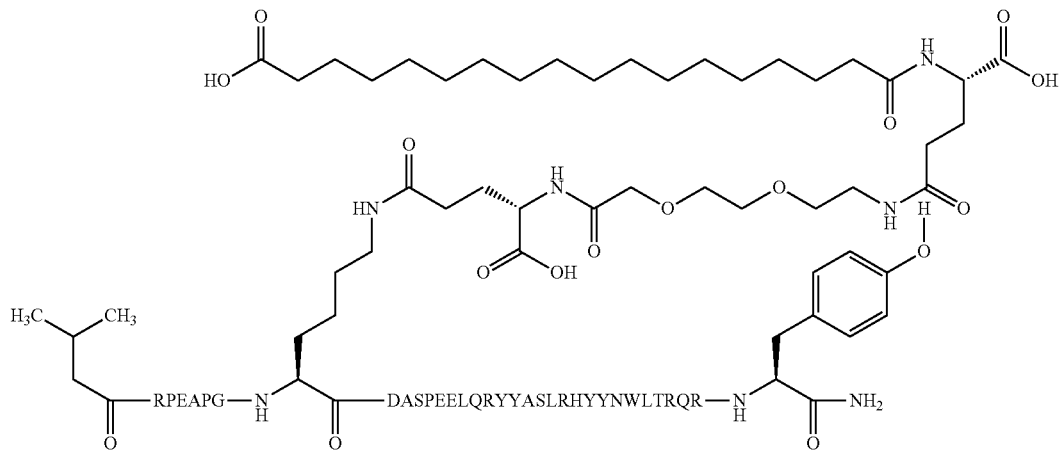

MW (average) calculated: 4898.45 g/mol.
457_LCMS01: Found [M+4H]4+: 1225.39; [M+5H]5+: 980.70.

The amino acid sequence of [Arg4,Lys10,Gln18,Tyr28,Trp30,Leu31]-PYY-(4-36) is given in SEQ ID NO:27.

Compound 60

N{alpha-4}-(3-Methylbutanoyl)-N{Epsilon-7}-[2-
[2-[2-[[(4S)-4-carboxy-4-(17-carboxyheptadecanoy-
lamino)butanoyl]amino]ethoxy]ethoxy]acetyl]-
[Arg4,Lys7,Gln18,Ala24,Tyr28,Trp30,Leu31]-PYY
(4-36)

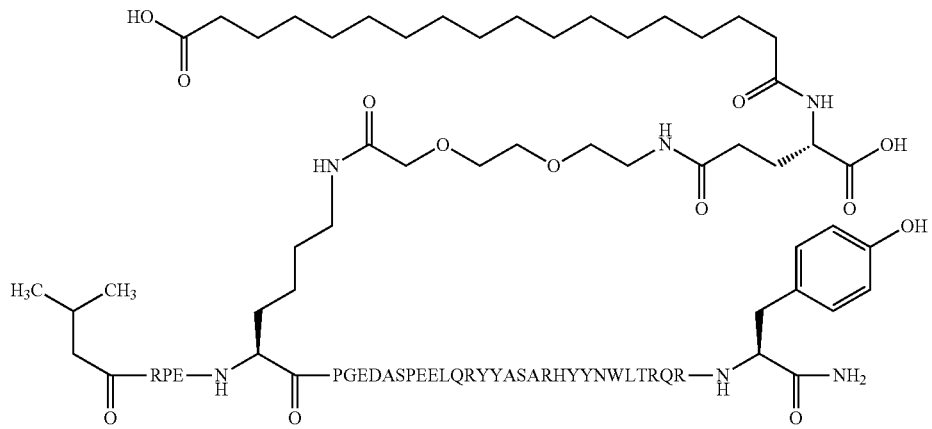

MW (average) calculated: 4785.29 g/mol.
457_LCMS01: Found [M+4H]4+: 1197.13; [M+5H]5+: 957.89.

The amino acid sequence of [Arg4,Lys7,Gln18,Ala24,Tyr28,Trp30,Leu31]-PYY(4-36) is given in SEQ ID NO:9.

Compound 61

N{alpha-4}-(3-Methylbutanoyl)-N{Epsilon-7}-[2-[2-[2-[[2-[2-[2-[[(4S)-4-carboxy-4-(15-carboxypentadecanoylamino)butanoyl]amino]ethoxy]ethoxy]acetyl]-amino]ethoxy]ethoxy]acetyl]-[Arg4,Lys7,Pro9,Gln18,Tyr28,Trp30,Leu31]-PYY-(4-36)

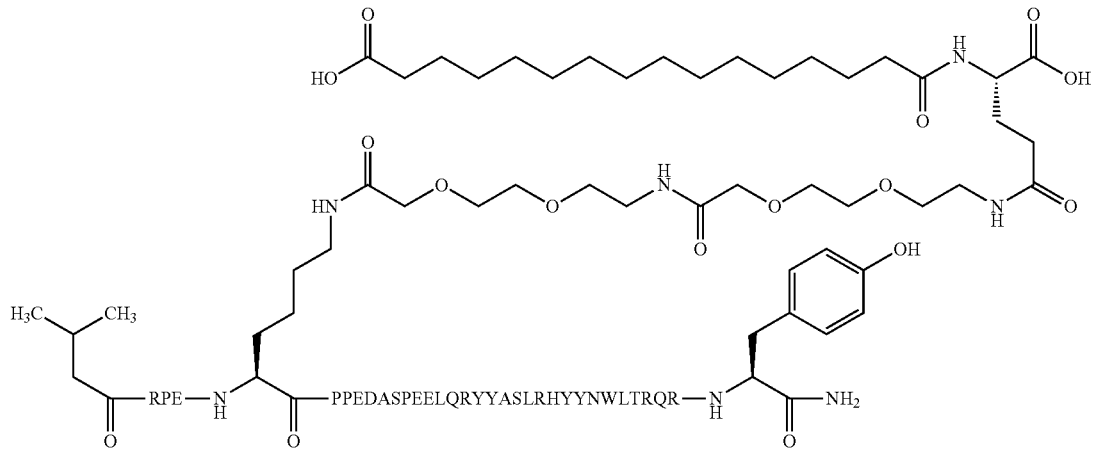

MW (average) calculated: 4984.53 g/mol.

457_LCMS01: Found [M+4H]4+: 1246.8; [M+5H]5+: 997.5.

The amino acid sequence of [Arg4,Lys7,Pro9,Gln18,Tyr28,Trp30,Leu31]-PYY-(4-36) is given in SEQ ID NO:5.

Compound 62

N{alpha-4}-(3-Methylbutanoyl)-N{Epsilon-7}-[2-[2-[2-[[(4S)-4-carboxy-4-(13-carboxytridecanoylamino)butanoyl]amino]ethoxy]ethoxy]acetyl]-[Arg4,Lys7,Gln18,Tyr28,Trp30,Leu31]-PYY(4-36)

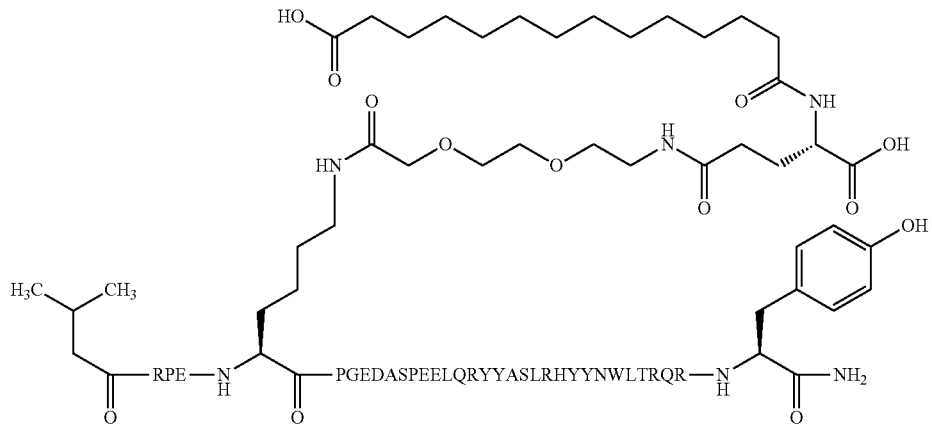

MW (average) calculated: 4771.26 g/mol.

457_LCMS01: Found [M+4H]4+: 1193.57; [M+5H]5+: 954.84.

The amino acid sequence of [Arg4,Lys7,Gln18,Tyr28,Trp30,Leu31]-PYY(4-36) is given in SEQ ID NO:4.

Compound 63

N{alpha-4}-(3-Methylbutanoyl)-N{Epsilon-7}-[2-[2-[2-[[2-[2-[2-[[(4S)-4-carboxy-4-(15-carboxypentadecanoylamino)butanoyl]amino]ethoxy]ethoxy]acetyl]-amino]ethoxy]ethoxy]acetyl]-[Arg4,Lys7,Gln18,Tyr28,Trp30,Leu31]-PYY(3-36)

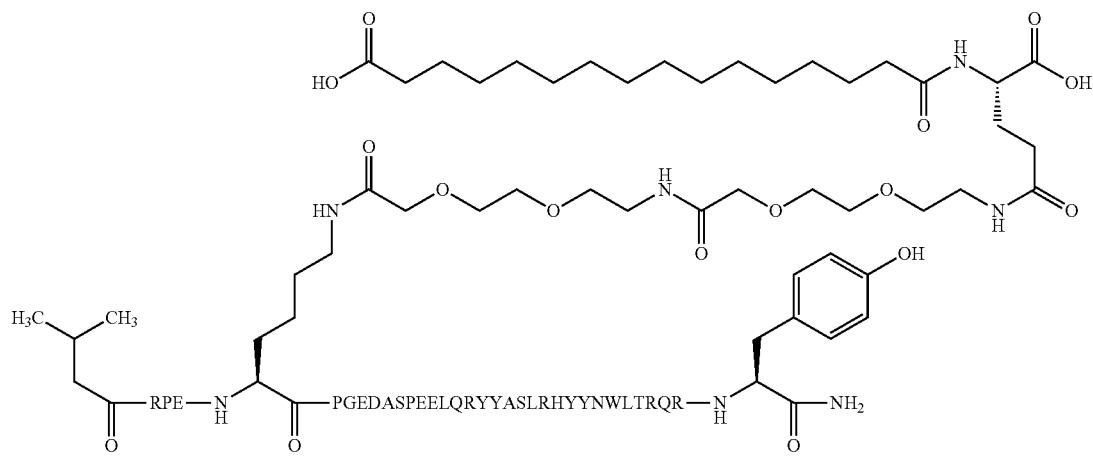

MW (average) calculated: 4944.47 g/mol.
457_LCMS01: Found [M+4H]4+: 1236.6; [M+5H]5+: 989.3.

The amino acid sequence of [Arg4,Lys7,Gln18,Tyr28,Trp30,Leu31]-PYY(3-36) is given in SEQ ID NO:3.

Compound 64

N{alpha-4}-(3-Methylbutanoyl)-[Arg4,Gln18,Tyr28,Trp30,Leu31]-PYY(4-36)

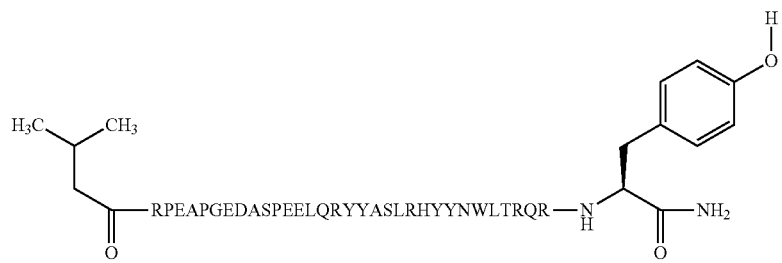

MW (average) calculated: 4199.56 g/mol.
457—LCMS01: Found [M+4H]4+: 1050.9; [M+5H]5+: 841.1.

The amino acid sequence of [Arg4,Gln18,Tyr28,Trp30,Leu31]-PYY(4-36) is given in SEQ ID NO:28.

Compound 65

N{alpha-4}-(3-Methylbutanoyl)-N{Epsilon-7}-[2-[2-[2-[[2-[2-[2-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]ethoxy]ethoxy]acetyl]amino]ethoxy]ethoxy]acetyl]-[Arg4,Lys7,Pro9,Gln18,Tyr28,Trp30,Leu31]-PYY(4-36)

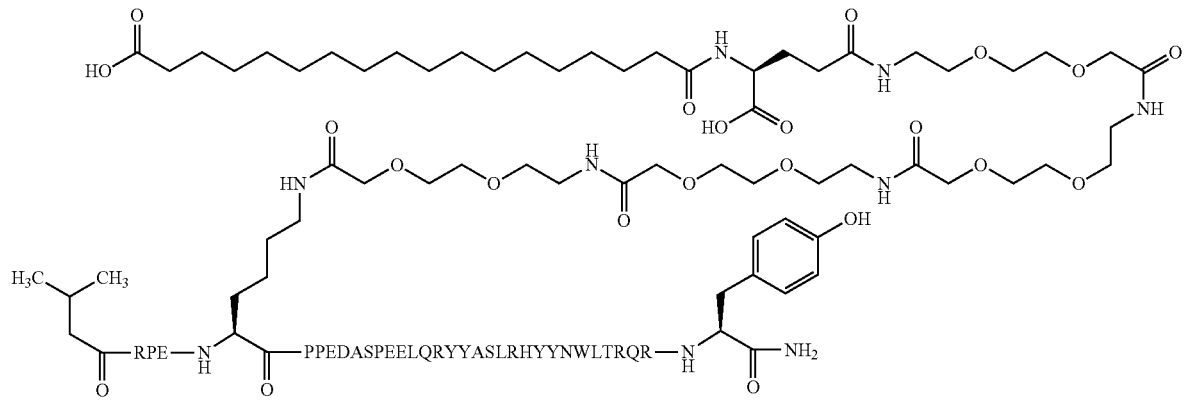

MW (average) calculated: 5302.90 g/mol.
457_LCMS01: Found [M+4H]4+: 1326.31; [M+5H]5+: 1061.05.
The amino acid sequence of [Arg4,Lys7,Pro9,Gln18,Tyr28,Trp30,Leu31]-PYY(4-36) is given in SEQ ID NO:5.

Compound 66

N{alpha-4}-(3-Methylbutanoyl)-N{Epsilon-7}-[2-[2-[2-[[2-[2-[2-[[(4S)-4-carboxy-4-(16-sulfohexadecanoylamino)butanoyl]amino]ethoxy]ethoxy]acetyl]-amino]ethoxy]ethoxy]acetyl]-[Arg4,Lys7,Pro9,Gln18,Tyr28,Trp30,Leu31]-PYY(4-36)

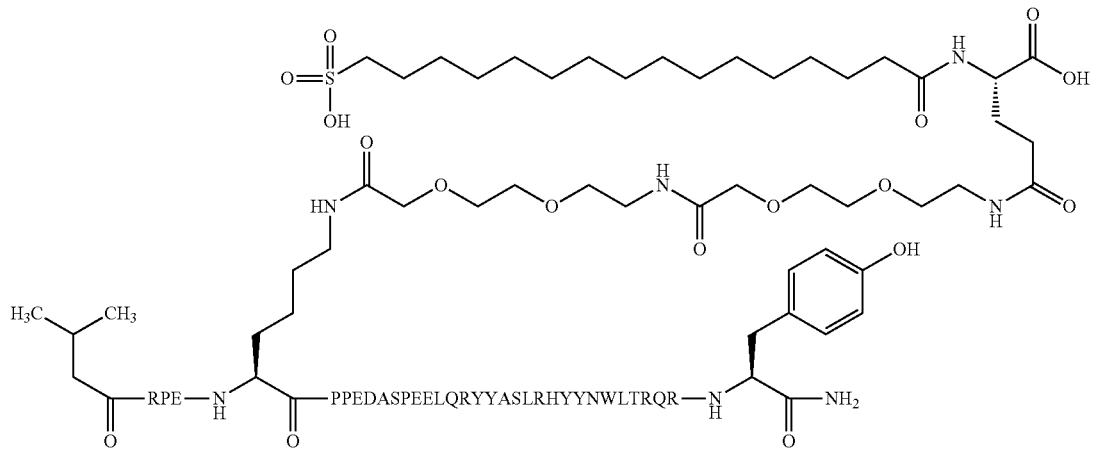

MW (average) calculated: 5034.61 g/mol.
457_LCMS01: Found [M+4H]4+: 1259.57; [M+5H]5+: 1007.91.
The amino acid sequence of [Arg4,Lys7,Pro9,Gln18,Tyr28,Trp30,Leu31]-PYY(4-36) is given in SEQ ID NO:5.

Compound 67

N{alpha-4}-(3-Methylbutanoyl)-N{Epsilon-7}-[2-
[2-[2-[[(4S)-4-carboxy-4-(16-sulfohexadecanoy-
lamino)butanoyl]amino]ethoxy]ethoxy]acetyl]-
[Arg4,Lys7,Gln18,Tyr28,Trp30,Leu31]-PYY(4-36)

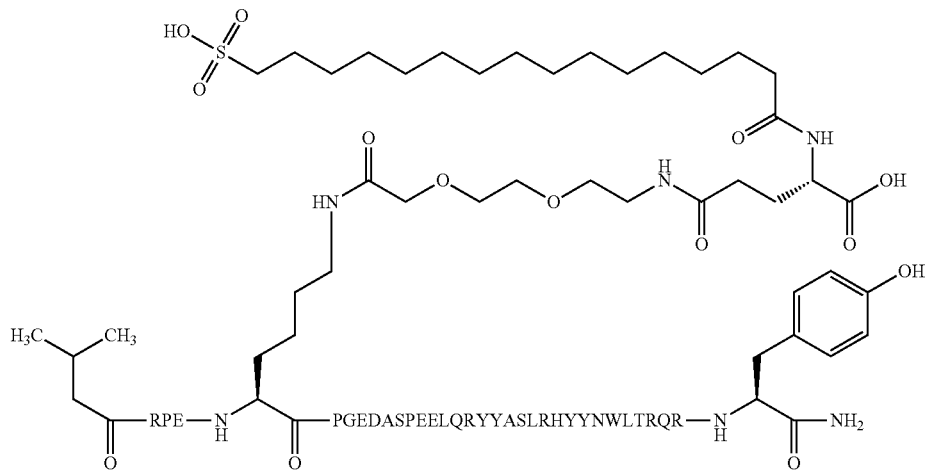

MW (average) calculated: 4849.39 g/mol.
457_LCMS01: Found [M+4H]4+: 1213.10; [M+5H]5+: 970.89.

The amino acid sequence of [Arg4,Lys7,Gln18,Tyr28, Trp30,Leu31]-PYY(4-36) is given in SEQ ID NO:4.

Compound 68

N{alpha-4}-(3-Methylbutanoyl)-N{Epsilon-7}-[2-
[2-[2-[[2-[2-[[(4S)-4-carboxy-4-(16-sulfohexade-
canoylamino)butanoyl]amino]ethoxy]ethoxy]acetyl]-
amino]ethoxy]ethoxy]acetyl]-[Arg4,Lys7,Gln18,
Tyr28,Trp30,Leu31]-PYY(4-36)

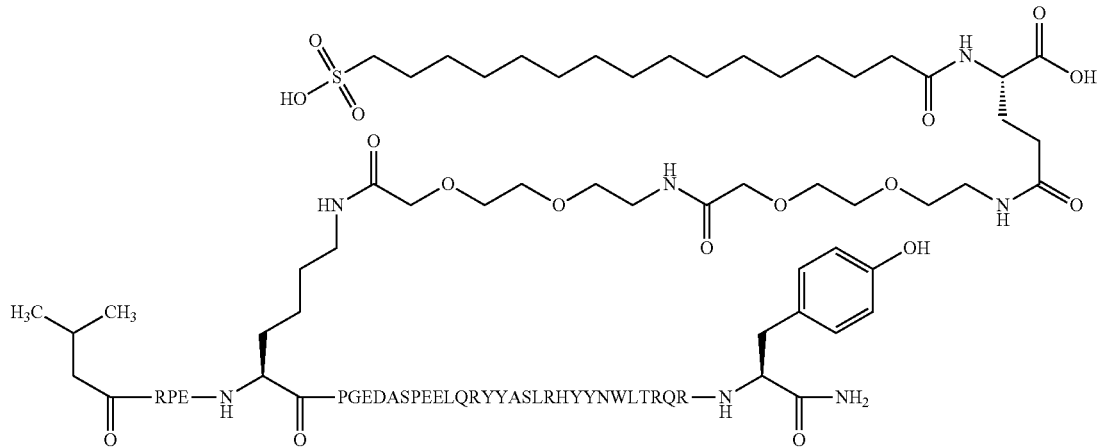

MW (average) calculated: 4994.55 g/mol.
457_LCMS01: Found [M+4H]4+: 1249.40; [M+5H]5+: 999.30.

The amino acid sequence of [Arg4,Lys7,Gln18,Tyr28, Trp30,Leu31]-PYY(4-36) is given in SEQ ID NO:4.

Compound 69

N{alpha-4}-(3-Methylbutanoyl)-N{Epsilon-10}-[(4S)-4-carboxy-4-[[2-[2-[2-[[(4S)-4-carboxy-4-(16-sulfohexadecanoylamino)butanoyl]amino]ethoxy]-ethoxy]acetyl]amino]butanoyl]-[Arg4,Pro9,Lys10,Gln18,Tyr28,Trp30,Leu31]-PYY-(4-36)

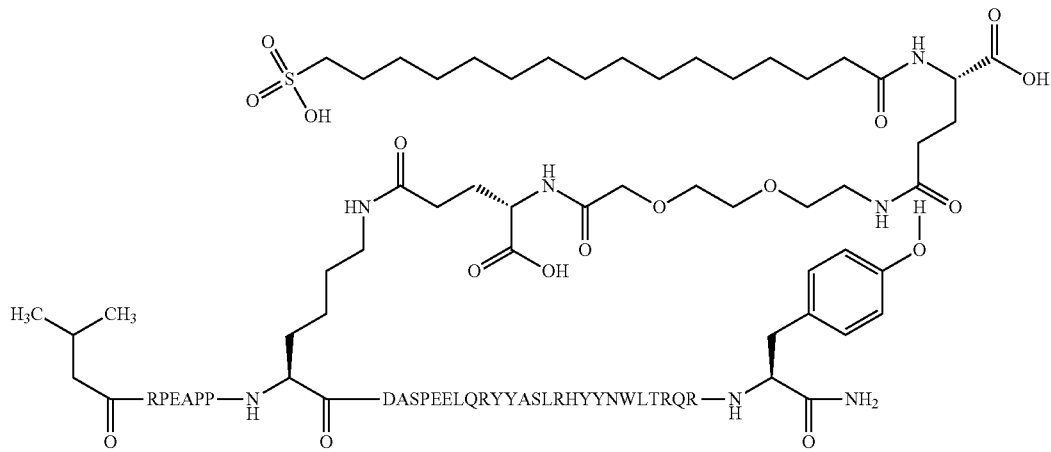

MW (average) calculated: 4960.54 g/mol.

457_LCMS01: Found [M+4H]4+: 1240.87; [M+5H]5+: 992.67.

The amino acid sequence of [Arg4,Pro9,Lys10,Gln18,Tyr28,Trp30,Leu31]-PYY-(4-36) is given in SEQ ID NO:26.

Compound 70

N{alpha-4}-(3-Methylbutanoyl)-N{Epsilon-7}-[(4S)-4-carboxy-4-(13-carboxytridecanoylamino)butanoyl]-[Arg4,Lys7,Pro9,Gln18,Tyr28,Trp30,Leu31]-PYY-(4-36)

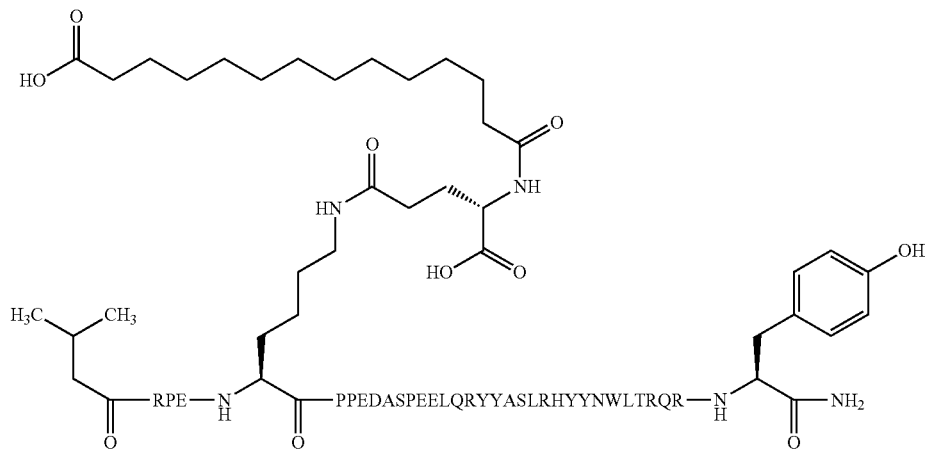

MW (average) calculated: 4666.17 g/mol.

457_LCMS01: Found [M+4H]4+: 1167.32; [M+5H]5+: 933.84.

The amino acid sequence of [Arg4,Lys7,Pro9,Gln18,Tyr28,Trp30,Leu31]-PYY-(4-36) is given in SEQ ID NO:5.

Compound 71

N{alpha-4}-(3-Methylbutanoyl)-N{Epsilon-7}-[2-[2-[2-[[(4S)-4-carboxy-4-(13-carboxytridecanoylamino)butanoyl]amino]ethoxy]ethoxy]acetyl]-[Arg4,Lys7,Pro9,Gln18,Tyr28,Trp30,Leu31]-PYY-(4-36)

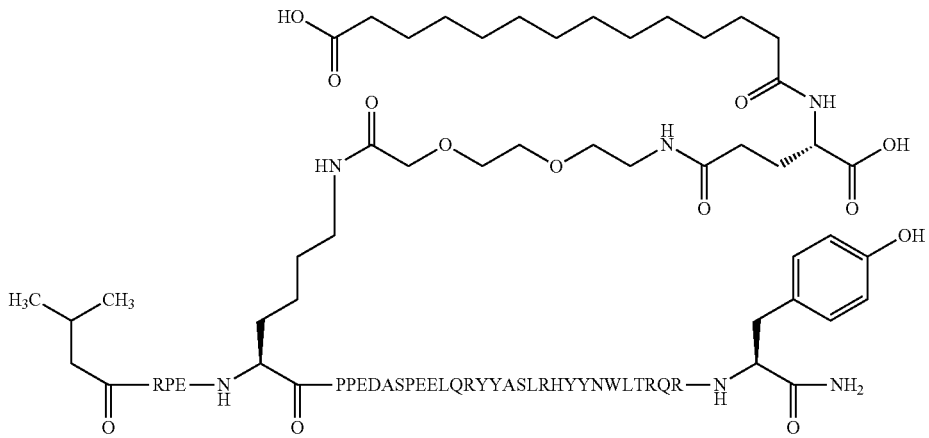

MW (average) calculated: 4811.32 g/mol.

457_LCMS01: Found [M+4H]4+: 1203.60; [M+5H]5+: 963.09.

The amino acid sequence of [Arg4,Lys7,Pro9,Gln18,Tyr28,Trp30,Leu31]-PYY-(4-36) is given in SEQ ID NO:5.

Compound 72

N{alpha-4}-(3-Methylbutanoyl)-[Arg4,Gln18,Val22,Tyr28,Trp30,Leu31]-PYY-(4-36)

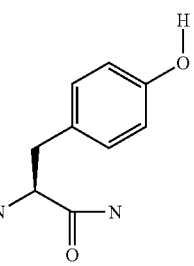
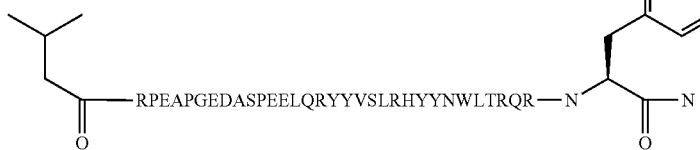

MW (average) calculated: 427.61 g/mol.

457_LCMS01: Found [M+4H]4+: 1057.27; [M+5H]5+: 846.03.

The amino acid sequence of [Arg4,Gln18,Val22,Tyr28,Trp30,Leu31]-PYY-(4-36) is given in SEQ ID NO:29.

Pharmacological Methods

The utility of PYY peptide derivatives or analogues thereof of the present invention as pharmaceutically active agents in the reduction of weight gain and treatment of obesity in mammals (such as humans), and for treatment of diabetes may be demonstrated by the activity of the agonists in conventional assays and in the in vitro and in vivo assays described below.

Such assays also provide a means whereby the activities of the PYY compounds of this invention can be compared with the activities of known compounds.

Example 2: Receptor Potency of PYY Compounds

The purpose of this example is to test the activity, or potency, of the PYY compounds in vitro. The Y2 in vitro potency is the measure of the activation of the human Y2 receptor subtype in a whole cell assay.

The Y2 potency of the PYY compounds of example 1 were determined using the Actone functional potency assay as described below. hPYY(3-36) (SEQ ID NO:2) was included as a reference.

Actone Functional Potency Assay

The Neuropeptide Y (NPY) receptors are $G_i$-coupled seven trans-membrane receptors that mainly signal through the cAMP dependent pathway by inhibiting adenylate cyclase activity which results in a decrease of cAMP production from ATP. The Actone assay is based on a modified calcium channel that has a selective binding for cAMP, resulting in cellular calcium influx, detected by a calcium responsive dye. In order to measure decreased levels of cAMP, as result of NPY receptor activation, the β1/β2-adrenoreceptor agonist, isoproterenol, is added to activate adenylate cyclase and increases cAMP levels in the cell. Decreased cellular calcium concentrations, reflecting a decrease of cAMP levels due to NPY receptor activation, is detected as a decrease in fluorescence from the calcium sensitive dye.

HEK-293 cells expressing the cAMP sensitive calcium channel and the human NPY Y2 receptor (CodexBiosolution, Gaithersburg, Md., USA) were seeded into poly lysine coated 384 well plates at a density of 14,000 cells/well (28,000 cells/well for Y2 cells) in a volume of 25 μl in DMEM medium containing 10% heat inactivated fetal calf serum (FCS), 1% Penicillin-Streptomycin, 250 μg/ml aminoglycoside antibiotic G418 and 1 μg/ml aminonucleoside antibiotic puromycin and 0.1 mM (4S)-4-carboxy-4-[[(4S)-4-carboxy-4-(19-carboxynonadecanoylamino)butanoyl]amino]butanoic acid (or another fatty acid derived compound that binds to albumin's fatty acid binding sites having no affinity to the Y receptors) for saturation of albumin. The cells were incubated over night at +37° C. in a humidified milieu in 5% $CO_2$ followed by addition of 25 μl calcium dye buffer containing: 1 vial Calcium 5 dye (Molecular Devices, Sunnyvale, Calif., USA) solved in 100 ml HBSS buffer containing 20 mM Hepes, 0.1% Ovalbumin, 0.005% Tween 20, 1.5 mM probenecid, 250 μM PDE-inhibitor 4-(3-Butoxy-4-methoxybenzyl)imidazolidin-2-one and 8 mM $CaCl_2$ and pH was adjusted to 7.40. Cells were incubated for 1 hour with the calcium dye buffer and then placed in a FLIPR Tetra System (Molecular Devices) where the liquid handling system added PYY compound (ranging from 30-0.03 nM final concentration) and isoproterenol (0.05 μM final concentration) simultaneously directly followed by fluorescence signal measurement (Ex540/Em590) for 360 seconds with 30 seconds intervals. All measurements were performed in duplicates and $EC_{50}$ values were calculated by nonlinear regression analysis of sigmoidal dose response curves using the GraphPad Prism v 5.02 (Graph Pad software, La Jolla, Calif., USA). The EC50 values are shown in table 1.

TABLE 1

In vitro potency

| Compound | Y2 EC50 (nM) |
| --- | --- |
| hPYY(1-36) | 0.69 |
| hPYY(3-36) | 0.92 |
| 1 | 1.04 |
| 2 | 0.65 |
| 3 | 0.55 |
| 4 | 0.57 |
| 5 | 0.67 |
| 6 | 0.39 |
| 7 | 2.20 |
| 8 | 0.47 |
| 9 | 0.24 |
| 10 | 1.69 |
| 11 | 1.14 |
| 12 | 4.35 |
| 13 | 0.27 |
| 14 | 0.28 |
| 15 | 0.96 |
| 16 | 0.35 |
| 17 | 0.76 |
| 18 | 1.47 |
| 19 | 2.05 |
| 20 | 0.56 |
| 21 | 0.27 |
| 22 | 1.24 |
| 23 | 0.47 |
| 24 | 0.90 |
| 25 | 1.75 |
| 26 | 0.38 |
| 27 | 0.40 |
| 28 | 0.28 |
| 29 | 1.42 |
| 30 | 0.31 |
| 31 | 0.76 |
| 32 | 0.33 |
| 33 | 3.20 |
| 34 | 0.86 |
| 35 | 0.46 |
| 36 | 0.23 |
| 37 | 0.53 |
| 38 | 0.21 |
| 39 | 0.37 |
| 40 | 0.53 |
| 41 | 0.44 |
| 42 | 2.10 |
| 43 | 0.77 |
| 44 | 1.35 |
| 45 | 1.05 |
| 46 | 0.36 |
| 47 | 0.78 |
| 48 | 2.20 |
| 49 | 1.07 |
| 50 | 0.92 |
| 51 | 0.99 |
| 52 | nd |
| 53 | 0.77 |
| 54 | 1.6 |
| 55 | 0.24 |
| 56 | 0.54 |
| 57 | 0.15 |
| 58 | 0.43 |
| 59 | 0.96 |
| 60 | 0.67 |
| 61 | 0.28 |
| 62 | 0.20 |
| 63 | 0.28 |
| 64 | 0.17 |
| 65 | 0.81 |
| 66 | 0.19 |
| 67 | 0.17 |
| 68 | 0.29 |
| 69 | 0.56 |
| 70 | 0.27 |
| 71 | 0.50 |
| 72 | 0.13 |

The PYY compounds of the inventions all display good Y2 potency.

Example 3: Y1, Y2, Y4 and Y5 Receptor Subtype Binding

The purpose of this example is to test the in vitro binding of the PYY compounds to the Y1, Y2, Y4 and Y5 receptor subtypes, respectively. The receptor binding affinity is a measure of affinity of a compound for the human Y1, Y2, Y4 and Y5 receptor subtypes, respectively.

The in vitro binding of the PYY compounds of example 1 were determined in a scintillation proximity assay (SPA) as described below. hPYY(3-36) (Example X, SEQ ID NO:2) was included as a reference.

Scintillation Proximity Assay (SPA)

NPY-Receptor Expressing Cell Lines.

All cells were cultured at +37° C. in a humidified atmosphere with 5% $CO_2$. BHK-21 clone 6-482-8 cells with inducible expression of the human Y1 receptor (P25929, NPY1R_HUMAN, Uniprot) were cultured in Dulbecco's Modified Eagle Medium (DMEM) with 10% heat inactivated fetal bovine serum (FBS), 1% Penicillin-Streptomycin (P/S), 1 mg/ml G418 antibiotic, 1 mg/ml Hygromycin B antibiotic and 1% Non-essential amino acids. 1 mM Isopropyl β-D-1-thiogalactopyranoside (IPTG) was added 24 hours prior to harvesting cells for induction of NPY-Y1 receptor expression. CHO-K1 cells stably expressing the human Y2 receptor (P49146, NPY2R_HUMAN, Uniprot)

were cultured in DMEM F-12 with 10% FBS, 1% P/S, 150 µg/ml Hygromycin B and 10 µg/ml Puromycin antibiotic. CHO-K1 cells stably expressing the human Y4 receptor (P50391, NPY4R_HUMAN, Uniprot) were cultured in DMEM F-12 with 10% FBS, 1% P/S, 10 µg/ml Puromycin. HEK-293 cells stably expressing the human Y5 receptor (Q15761, NPY5R_HUMAN, Uniprot) were cultured in DMEM F-12 medium containing 10% FBS, 1% Penicillin-Streptomycin, 250 µg/ml G418 and 1 µg/ml puromycin.

Membrane Preparation.

Cultured cells were detached mechanically by scraping and washed in ice cold PBS (137 mM NaCl, 2.7 mM KCl, 4.3 mM $Na_2HPO_4$, 1.47 mM $KH_2PO_4$ pH adjusted to 7.4) and transferred to tubes and centrifuged for 5 minutes at 1000 g at +4° C. Pellets were resuspended in ice cold homogenization buffer; Y1: 20 mM Hepes, 10 mM EDTA, with 2 complete EDTA-free protease inhibitor cocktail tablets/50 ml (Roche, Mannheim, Germany) pH 7.4); Y2, Y4: 20 mM Hepes, 5 mM $MgCl_2$, 1 mg/ml Bacitracin, pH 7.1; Y5: 10 mM NaCl, 20 mM Hepes, 0.22 mM $KH_2PO_4$, 1.26 mM $CaCl_2$, 0.81 mM $MgSO_4$, pH 7.4 and then homogenized for 30 seconds using a tissue homogenizer at medium speed. The homogenate was centrifuged at 35000 g using an ultracentrifuge for 10 minutes at +4° C. and the supernatant was discarded and fresh homogenization buffer added. Homogenization of the pellet was repeated a total of three times. The final pellet was resuspended in a few milliliters of homogenization buffer and protein concentration was determined using the Bradford method and measured at 595 nm in a microplate reader. Protein concentration were adjusted to 1 mg/ml and transferred to cryotubes and stored at −80° C. 250 mM sucrose was added to Y5 membranes prior to freezing.

Assay.

Human Y receptor SPA binding assay were performed in white 96-well plates in a total volume of 200 µl per well. Wheat germ agglutinin coated beads containing scintillation liquid (PerkinElmer, Waltham, Mass., USA) were reconstituted in binding buffer; Y1, Y2: 50 mM Hepes, 1 mM $CaCl_2$, 5 mM $MgCl_2$, 0.02% tween 20, 0.25% ovalbumin pH 7.4; Y4, Y5: 20 mM Hepes, 10 mM NaCl, 0.22 mM $KH_2PO_4$, 1.26 mM $CaCl_2$, 0.81 mM $MgSO_4$, 0.1% bacitracin and 0.25% ovalbumin pH 7.4 and mixed with membrane preparation to give final concentration of 0.5 mg beads/well and 3 µg of Y1 membranes/well, 3 µg of Y2 membranes/well, 1 µg of Y4 membranes/well or 20 µg of Y5 membranes/well. 50000 cpm per well of radio ligand human [$^{125}$I]-PYY(1-36) was added corresponding to a concentration of 100 µM in Y1, Y2 and Y5 binding assays. 50000 cpm per well of radio ligand human [$^{125}$I]-Pancreatic Polypeptide (PP) corresponding to a concentration of 100 µM was used in Y4 binding assay.

Freeze dried analogues were dissolved in 80% dimethyl sulfoxide (DMSO), 19% $H_2O$ and 1% acetic acid ($CH_3COOH$) to stock solutions of 2000 µM (Y1, Y4 and Y5) and 200 µM (Y2) and serial dilutions (1:10) were performed in binding buffer to final concentrations ranging from 10000 nM to 1 µM in the Y1, Y4 and Y5 assays and 1000 nM to 0.1 µM in the Y2 assay. Plates were sealed and incubated at +25° C. for 2 hours in a plate shaker set at 400 rpm and thereafter centrifuged at 1500 rpm for 10 minutes prior to reading of luminescence on a microplate scintillation and luminescence counter. Y1 SPA plates were let to stand in room temperature for 16 hours prior to reading. Displacement of radioligand was measured as reduction in luminescence and $IC_{50}$ values were calculated by nonlinear regression analysis of sigmoidal dose-response curves. Ki values for binding affinity were acquired by the Cheng-Prusoff equation (Ki=IC50/(1+[L]/Kd) including receptor specific Kd values (Y1=0.556 nM; Y2=0.275 nM; Y4=0.111 nM; Y5=0.345 nM), radioligand concentration and IC50 values.

TABLE 2

Y receptor binding affinity

| Compound | Y2 Ki (nM) | Y1 Ki (nM) | Y4 Ki (nM) | Y5 Ki (nM) | Ratio of Y4/Y2 EC50 values | Ratio of Y5/Y2 EC50 values |
|---|---|---|---|---|---|---|
| hPYY (1-36) | 0.36 | 0.16 | 1.70 | 0.61 | 4.6 | 1.7 |
| hPYY (3-36) | 0.46 | 41 | 35 | 4.5 | 76 | 9.7 |
| 1 | 0.31 | >10000 | 2299 | 67 | 7416 | 216 |
| 2 | 0.26 | >10000 | 2949 | 247 | 11340 | 950 |
| 3 | 0.45 | >10000 | 4593 | 102 | 10320 | 229 |
| 4 | 0.34 | >10000 | 4654 | 221 | 13688 | 650 |
| 5 | 3.0 | >10000 | 9708 | 1087 | 3272 | 366 |
| 6 | 0.49 | >10000 | 5293 | 69 | 10913 | 142 |
| 7 | 0.80 | >10000 | 7942 | 760 | 9989 | 956 |
| 8 | 0.40 | >10000 | 6329 | 115 | 15823 | 244 |
| 9 | 0.70 | >10000 | 4354 | 67.5 | 6265 | 97 |
| 10 | 0.34 | >10000 | 4282 | 260 | 12594 | 764 |
| 11 | 0.67 | >10000 | 5400 | 208 | 8120 | 312 |
| 12 | 1.1 | >10000 | 4926 | 210 | 4478 | 191 |
| 13 | 0.58 | >10000 | 6040 | 172 | 10473 | 297 |
| 14 | 0.53 | 8815 | 7814 | 248 | 14883 | 472 |
| 15 | 0.47 | >10000 | 4698 | 202 | 10102 | 433 |
| 16 | 0.37 | >10000 | 5947 | 158 | 16292 | 433 |
| 17 | 0.72 | >10000 | 2730 | 85 | 3792 | 118 |
| 18 | 0.48 | >10000 | 5354 | 201 | 11153 | 419 |
| 19 | 0.68 | >10000 | 5899 | 340 | 8739 | 503 |
| 20 | 0.59 | >10000 | 4730 | 359 | 8086 | 614 |
| 21 | 0.67 | >10000 | 7957 | 93 | 11966 | 139 |
| 22 | 0.37 | >10000 | 4827 | 135 | 13046 | 365 |
| 23 | 0.22 | >10000 | 461 | 43 | 2144 | 202 |
| 24 | 0.26 | 7123 | 556 | 36 | 2178 | 143 |
| 25 | 0.30 | >10000 | 443 | 92 | 1460 | 303 |
| 26 | 0.41 | 8941 | 970 | 114 | 2396 | 280 |
| 27 | 0.23 | >10000 | 601 | 82 | 2613 | 358 |
| 28 | 1.6 | 4335 | 2182 | 505 | 1363 | 316 |
| 29 | 0.52 | >10000 | 2992 | 260 | 5809 | 504 |
| 30 | 1.3 | 9476 | 7273 | 935 | 5697 | 732 |
| 31 | 0.30 | >10000 | 2675 | 166 | 9068 | 563 |
| 32 | 0.20 | >10000 | 1894 | 225 | 9468 | 1126 |
| 33 | 0.68 | >10000 | 2579 | 382 | 3820 | 566 |
| 34 | 0.55 | >10000 | 3127 | 79 | 5686 | 144 |
| 35 | 0.37 | >10000 | 3958 | 132 | 10697 | 357 |
| 36 | 0.35 | 9233 | 4891 | 213 | 13974 | 609 |
| 37 | 0.80 | >10000 | 8777 | 518 | 10971 | 647 |
| 38 | 0.28 | >10000 | 4578 | 217 | 16348 | 773 |
| 39 | 0.49 | >10000 | 6545 | 762 | 13495 | 1571 |
| 40 | 0.32 | >10000 | 4663 | 173 | 14803 | 549 |
| 41 | 0.45 | >10000 | 6217 | 284 | 13816 | 631 |
| 42 | 0.59 | >10000 | 7251 | 334 | 12289 | 565 |
| 43 | 0.49 | >10000 | 6404 | 509 | 13203 | 1050 |
| 44 | 0.33 | >10000 | 6670 | 470 | 20212 | 1423 |
| 45 | 0.35 | >10000 | 4180 | 228 | 11943 | 651 |
| 46 | 0.27 | >10000 | 7209 | 155 | 27204 | 585 |
| 47 | 0.25 | >10000 | 4288 | 315 | 17150 | 1260 |
| 48 | 0.80 | >10000 | 7942 | 760 | 9989 | 956 |
| 49 | 0.42 | >10000 | 3692 | 377 | 8789 | 899 |
| 50 | 3.3 | >10000 | >10000 | 122 | >3077 | 37 |
| 51 | 2.3 | 2405 | >10000 | 116 | >4348 | 50 |
| 52 | 0.66 | >10000 | 5687 | 182 | 8617 | 275 |
| 53 | 1.15 | >10000 | 9289 | 452 | 8077 | 393 |
| 54 | 3.1 | 2421 | 5913 | 254 | 1907 | 82 |
| 55 | 0.70 | >10000 | 4355 | 68 | 6266 | 97 |
| 56 | 1.4 | >10000 | 4407 | 279 | 3060 | 193 |
| 57 | 0.34 | >10000 | 7036 | 102 | 20694 | 300 |
| 58 | 0.65 | >10000 | 4458 | 180 | 6912 | 279 |
| 59 | 0.72 | >10000 | 5902 | 279 | 8197 | 387 |
| 60 | 1.6 | >10000 | 3049 | 299 | 1906 | 187 |
| 61 | 0.47 | >10000 | 6999 | 403 | 15052 | 867 |
| 62 | 0.73 | 7692 | 6159 | 250 | 8437 | 343 |
| 63 | 0.45 | >10000 | 5771 | 276 | 12824 | 612 |

TABLE 2-continued

Y receptor binding affinity

| Compound | Y2 Ki (nM) | Y1 Ki (nM) | Y4 Ki (nM) | Y5 Ki (nM) | Ratio of Y4/Y2 EC50 values | Ratio of Y5/Y2 EC50 values |
|---|---|---|---|---|---|---|
| 64 | 0.27 | 1709 | 1239 | 48 | 4588 | 176 |
| 65 | 0.55 | >10000 | >10000 | 275 | >18349 | 505 |
| 66 | 0.47 | 5902 | 6214 | 183 | 13221 | 389 |
| 67 | 0.76 | >10000 | 3855 | 108 | 5106 | 143 |
| 68 | 0.44 | >10000 | 3709 | 274 | 8430 | 622 |
| 69 | 0.94 | >10000 | 5688 | 146 | 6051 | 155 |
| 70 | 0.76 | >10000 | 4280 | 141 | 5669 | 186 |
| 71 | 0.51 | >10000 | 2954 | 264 | 5791 | 518 |
| 72 | 0.195 | 1039 | 846 | 37 | 4339 | 189 |

The PYY compounds of the invention all display good Y2 binding while the binding affinity on the receptors Y1, Y4 and Y5 is strongly reduced.

Example 4: Pharmacokinetic Study in Minipigs

The purpose of this study is to determine the half-life in vivo of the PYY compounds after i.v. administration to minipigs, i.e. the prolongation of their time in the body and thereby their time of action. This is done in a pharmacokinetic (PK) study, where the terminal half-life of the derivative in question is determined. By terminal half-life is generally meant the period of time it takes to halve a certain plasma concentration, measured after the initial distribution phase.

In Vivo Studies on Pharmacokinetic Evaluation in Göttingen Minipigs after Intravenous Administration.

Animals.

Göttingen minipigs female, 15-25 kg, purchased from Ellegaard Minipigs, Denmark. The animals were housed in the Animal Unit, Novo Nordisk A/S and were kept and handled according to normal procedure in the Animal Unit. After minimum 2 weeks of acclimatization two permanent central venous catheters were implemented in vena cava caudalis in each animal. After surgery the animals were in their normal individual pens during the pharmacokinetic experiments.

Body Weight.

The animals were weighed weekly. The animals were fasted on the morning prior to dosing but had ad libitum access to water; food was supplied during dosing.

Administration of Peptides and Dosing Solutions.

Intravenous injections were given through the central short catheter, which was flushed with minimum 10 ml of sterile saline post administration. The test substance was dosed at 15 nmol/kg, n=3, in a volume of 0.05 ml/kg. Buffer: 50 mM sodium phosphate, 70 mM sodium chloride, 0.05% tween 80, pH 7.4 or 20 mM HEPES, 2.2% glycerol, 0.05% Polysorbate 80, pH 6.5.

Blood Samples and Analysis.

Blood samples were taken through the central catheter according to the following schedule: Predose, 5, 15, 30, 45 min, 1 h, 1.5 h, 2 h, 3 h, 4 h, 6 h, 8 h, 10 h, 24 h, 48 h, 72 h, 96 h, 120 h, 168 h, 192 h, 216 h, 240 h, 264 h and 288 h. On day 1 the catheters are coupled to extension tubes, which will be removed at the end of day 1. Samples (0.8 ml) were taken through the catheter. Blood was collected in test tubes containing EDTA buffer (8 mM) and 50 µl Val-Pyr buffer (Stabilization buffer containing 3.097 g K3EDTA dissolved in 50 ml Trasylol and 0.5 ml 20 mM Val-Pyr was added. The pH was regulated to 7.4). After each blood sample the catheter was flushed with minimum 5 ml of sterile 0.9% NaCl and 10 IE/ml heparin. Aseptic technique was demanded to avoid bacterial growth in the catheter that increases the risk of clot formation in the catheter. Samples were kept on wet ice until centrifugation (10 min, 4° C., 1942 g). Afterwards, plasma (min. 200 µl) was transferred immediately to Micronic tubes and kept at −20° C. until analysis. The plasma samples were analysed by LC/MS as described below.

Data and Results.

Plasma concentration-time profiles was analysed by a non-compartmental pharmacokinetics analysis using Phoenix (Pharsight Inc., Mountain View, Calif., USA). Calculations were performed using individual concentration-time values from each animal.

Sample Analysis

Quantitative Assay for Plasma Samples.

The test substances were assayed in plasma by Turbulent Flow Chromatography coupled to Liquid Chromatography with subsequent Mass Spectrometric Detection (TFC/LC/MS). The selectivity of the method allowed various compounds to be quantitated in one sample, e.g. cassette dosing of four compounds per animal. The concentrations of the test substance in unknown samples were calculated using the peak area as a function of amount. Calibration graphs based on plasma samples spiked with the analyte were constructed by regression analysis. Typical dynamic range for the assay was 1-2,000 nmol/l. The method performance was assured by co-assaying quality control (QC) samples in duplicate at three concentration levels. Stock and working solutions of analytes were prepared in plasma and incubated by 37° C. for 1 hour.

Sample Preparation.

40.0 µl EDTA-plasma was added 160 µl 50% methanol, 1% formic acid, then vortexed and centrifuged at 14300 rpm (16457 g) at 4° C. for 20 minutes. The supernatant was transferred to a 96 well plate, (the plates have been preincubated with 0.4% BSA, 37° C. for ½ hour). Injection volume was 25 µl.

For sample clean up a TurboFlow Cyclone column (0.5× 50 mm) both from Thermo Scientific, Franklin, Mass., USA, was used and the LC separation was done either on an Onyx C18 column (2.0×50 mm) from Phenomenex, Torrance, Calif., USA. Eluents were isocratic and gradient combinations of methanol, acetonitril, Milli-Q water and formic acid. Selective detection was done by mass spectrometry operated in positive mode ionisation.

Data Handling.

Plasma concentration-time profiles was analysed by a non-compartmental pharmacokinetics analysis using Phoenix (Pharsight Inc., Mountain View, Calif., USA). Calculations were performed using individual concentration-time values from each animal.

TABLE 3

Half-life (t½)

| Compound no. hPYY(3-36) | t½ (hours) |
|---|---|
| 1 | 69 |
| 2 | 131 |
| 3 | 84 |
| 4 | 122 |
| 5 | 55 |
| 6 | 96 |
| 8 | 101 |

TABLE 3-continued

Half-life (t½)

| Compound no. hPYY(3-36) | t½ (hours) |
|---|---|
| 10 | 123 |
| 11 | 92 |
| 12 | 118 |
| 14 | 81 |
| 16 | 87 |
| 19 | 110 |
| 20 | 91 |
| 21 | 102 |
| 22 | 123 |
| 23 | 49 |
| 24 | 36 |
| 25 | 94 |
| 26 | 53 |
| 27 | 105 |
| 28 | 43 |
| 30 | 52 |
| 32 | 60 |
| 33 | 86 |
| 36 | 77 |
| 38 | 61 |
| 39 | 57 |
| 40 | 83 |
| 41 | 79 |
| 42 | 133 |
| 48 | 122 |
| 49 | 100 |
| 50 | 94 |
| 55 | 158 |
| 58 | 39 |
| 61 | 30 |
| 62 | 7 |
| 63 | 30 |
| 66 | 54 |
| 67 | 71 |
| 68 | 58 |
| 69 | 64 |
| 70 | 34 |
| 71 | 9 |

The tested PYY compounds of the invention have very long half-lives as compared to the half-life of hPYY(3-36).

Example 5: Pharmacodynamic Studies in Db/Db Mice

In order to determine the in vivo effects of the PYY compounds on blood glucose and food intake in a diabetic setting, the compounds were tested in an obese, diabetic mouse model (db/db mice) as described below.

Male db/db mice are housed in a normal daily rhythm (6 pm to 6 am dark cycle) and provided ad libitum access to Altromin diet. At 11-13 weeks of age the mice are matched for blood glucose as well as body weight and divided into matching groups of 9 mice and housed 3 per cage. Mice are dosed subcutaneously with the indicated compound or vehicle (50 mM Na2HPO4, pH 7.4, 70 mM NaCl, 0.05% Tween 80) at a volume of 2.5 ml/kg at the indicated doses at 4 pm (time=0) and in some experiments a second injection was given at time=23 hours. Blood glucose and food intake are measured at the indicated time points post injection, e.g. at 23 hours (23 h) and 40 hours (40 h) post injection. Blood samples for blood glucose are taken from the tail vein, into a 5 µl heparin coated capillary tube which is placed in an eppendorf tube with Biosen® system solution (250 µl). The samples are analysed on a Biosen® instrument immediately. Blood glucose (BG) measurements are reported as mean of vehicle adjusted % BG relative to pre-treatment and calculated as follows:

100−[% $BG$(vehicle,average)−% $BG$]

where,

% BG=100*[BG(time=t)/BG(pre-treatment)]

and % BG(vehicle,average)=average of % BG values for the vehicle group at time=t relative to vehicle pre-treatment.

Food intake is reported as mean food intake per cage as a percentage of average food intake of the vehicle group for the indicated interval.

TABLE 4

Effect on blood glucose in db/db mice. Blood glucose (BG) measurements are reported as mean of vehicle adjusted % BG relative to pre-treatment

| Compound | Dose (nmol/kg) | % relative change in blood glucose 0-24 h | 24-40 h |
|---|---|---|---|
| 26 | 30 | 54 | 55 |
| 25 | 30 | 37 | 47 |
| 31 | 10 | 29 | 39 |
| 31 | 30 | 52 | 53 |
| 27 | 5 | 105 | 101 |
| 2 | 5 | 101 | 93 |
| 32 | 5 | 64 | 75 |
| 32 | 10 | 34 | 46 |
| 32 | 30 | 25 | 50 |
| 18 | 10 | 83 | 85 |
| 22 | 10 | 72 | 77 |
| 3 | 10 | 32 | 40 |
| 3 | 30 | 37 | 52 |
| 10 | 5 | 106 | 96 |
| 38 | 10 | 40 | 27 |
| 49 | 10 | 81 | 85 |
| 4 | 5 | 74 | 75 |
| 4 | 10 | 39 | 30 |
| 4 | 30 | 30 | 24 |
| 40 | 5 | 76 | 79 |
| 40 | 10 | 33 | 38 |
| 40 | 30 | 37 | 37 |
| 18 | 10 | 83 | 85 |
| 22 | 10 | 72 | 77 |
| 8 | 5 | 94 | 82 |
| 8 | 10 | 56 | 51 |
| 8 | 30 | 39 | 52 |
| 21 | 5 | 73 | 54 |
| 21 | 10 | 50 | 46 |
| 21 | 30 | 31 | 25 |
| 61 | 10 | 87 | 81 |
| 66 | 10 | 83 | 77 |
| 69 | 10 | 84 | 79 |

TABLE 5

Effect on food intake in db/db mice. Food intake is reported as mean food intake per cage as a percentage of average food intake of the vehicle group for the indicated interval.

| Compound | Dose (nmol/kg) | % relative food intake 0-24 h | 24-40 h |
|---|---|---|---|
| 26 | 30 | 28 | 17 |
| 25 | 30 | 29 | 5 |
| 31 | 10 | 62 | 22 |
| 31 | 30 | 33 | 7 |
| 27 | 5 | 63 | 73 |
| 2 | 5 | 79 | 77 |
| 32 | 5 | 53 | 34 |
| 32 | 10 | 30 | 11 |
| 32 | 30 | 12 | 2 |
| 18 | 10 | 57 | 61 |
| 22 | 10 | 57 | 52 |

TABLE 5-continued

Effect on food intake in db/db mice. Food intake is reported as mean food intake per cage as a percentage of average food intake of the vehicle group for the indicated interval.

| Compound | Dose (nmol/kg) | % relative food intake 0-24 h | % relative food intake 24-40 h |
|---|---|---|---|
| 3 | 10 | 62 | 35 |
| 3 | 30 | 43 | 9 |
| 10 | 5 | 68 | 69 |
| 38 | 10 | 10 | 12 |
| 49 | 10 | 51 | 55 |
| 4 | 5 | 56 | 48 |
| 4 | 10 | 21 | 21 |
| 4 | 30 | 29 | 4 |
| 40 | 5 | 58 | 43 |
| 40 | 10 | 37 | 29 |
| 40 | 30 | 25 | 16 |
| 18 | 10 | 58 | 61 |
| 22 | 10 | 58 | 52 |
| 8 | 5 | 69 | 51 |
| 8 | 10 | 38 | 34 |
| 8 | 30 | 34 | 8 |
| 21 | 5 | 55 | 31 |
| 21 | 10 | 29 | 25 |
| 21 | 30 | 26 | 10 |
| 61 | 10 | 64 | 53 |
| 66 | 10 | 46 | 58 |
| 69 | 10 | 61 | 62 |

These data strongly support the blood glucose lowering effect and the inhibition of food intake of the PYY compounds of the invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A PYY compound having a maximum of 10 amino acid modifications as compared to hPYY(3-36) (SEQ ID NO:2), wherein the PYY compound comprises
   i) lysine at the position corresponding to position 7 or 10 of hPYY(1-36) (SEQ ID NO:1);
   ii) tryptophan at the position corresponding to position 30 of hPYY(1-36) (SEQ ID NO:1);
   iii) leucine at the position corresponding to position 31 of hPYY(1-36) (SEQ ID NO:1);
   iv) tyrosine at the position corresponding to position 28 of hPYY(1-36) (SEQ ID NO:1) and/or isoleucine at the position corresponding to position 22 of hPYY(1-36) (SEQ ID NO:1); and
   v) a modifying group attached to the epsilon amino group of said lysine at the position corresponding to position 7 or 10 of hPYY(1-36) (SEQ ID NO:1),
   wherein said modifying group is defined by A-[B]$_r$-C- or A-[B]$_r$-C-[B]$_w$, wherein
   A- is selected from Chem. 1 and Chem. 2

$$HOOC-(CH_2)_p-CO-*, \quad \text{Chem. 1:}$$

$$HO_3S-(CH_2)_q-CO-* \quad \text{Chem. 2:}$$

wherein p is an integer in the range of 14-18, and q is an integer in the range of 15-17;
   B- is Chem. 3

$$*[NH-CH(COOH)-(CH_2)_2-CO-]-*, \quad \text{Chem. 3:}$$

r is an integer in the range of 1-3;
   w is an integer in the range of 1-3; and
   C- is absent or selected from Chem. 4 and Chem. 5

$$*[NH-(CH_2)_2-[O-(CH_2)_2]_s-O-(CH_2)_t-CO-]_u-* \quad \text{Chem. 4:}$$

$$*[NH-(CH_2)_v-CO-]_x-* \quad \text{Chem. 5:}$$

wherein s is an integer in the range of 1-3, t is an integer in the range of 1-3, u is an integer in the range of 1-4, v is an integer in the range of 3-7, and x is an integer in the range of 1-3;
   wherein * denotes the points of attachment, and wherein A, B, and C are interconnected via amide bonds and in the sequence indicated via said point of attachments; or a pharmaceutically acceptable salt, amide, or ester of said PYY compound; and
   wherein if the modifying group is A-B-C-B, C cannot be absent.

2. A PYY compound according to claim 1, wherein A- is selected from Chem. 1 and Chem. 2

$$HOOC-(CH_2)_p-CO-*, \quad \text{Chem. 1:}$$

$$HO_3S-(CH_2)_q-CO-* \quad \text{Chem. 2:}$$

and wherein p is an integer in the range of 16-18, and q is 15.

3. A PYY compound according to claim 1, wherein A- is Chem. 1

$$HOOC-(CH_2)_p-CO-*, \quad \text{Chem. 1:}$$

and wherein p is an integer in the range of 14-18.

4. A PYY compound according to claim 1, wherein A- is Chem. 1

$$HOOC-(CH_2)_p-CO-*, \quad \text{Chem. 1:}$$

and wherein p is an integer in the range of 16-18.

5. A PYY compound according to claim 1, wherein B- is Chem. 3

$$*[NH-CH(COOH)-(CH_2)_2-CO-]-*, \quad \text{Chem. 3:}$$

r is an integer in the range of 1-2;
   w is an integer in the range of 1-2.

6. A PYY compound according to claim 1, wherein C- is absent or selected from Chem. 4a and Chem. 5a

*[NH—(CH₂)₂—[O—(CH₂)₂]₂—O—(CH₂)₂—
        CO—]ᵤ—*                                    Chem. 4a:

*[NH—(CH₂)₅—CO—]ₓ—*                                Chem. 5a:

wherein u is an integer in the range of 1-4, and x is an integer in the range of 1-3.

7. A PYY compound according to claim 1, wherein the positions corresponding to positions 1 and 2 of hPYY(1-36) (SEQ ID NO:1) are absent.

8. A PYY compound according to claim 1, wherein the positions corresponding to positions 1-3 of hPYY(1-36) (SEQ ID NO:1) are absent.

9. A PYY compound according to claim 1, wherein the positions corresponding to positions 1-3 of hPYY(1-36) (SEQ ID NO:1) are absent, and wherein the PYY compound further comprises an N-terminal substituent, wherein the N-terminal substituent is an alkoxy group comprising up to 12 carbon atoms.

10. A PYY compound selected from the following:
N{Epsilon-7}-[(4S)-4-carboxy-4-[[(4S)-4-carboxy-4-(17-carboxyheptadecanoylamino)-butanoyl]amino]butanoyl]-[Arg4,Lys7,Gln18,Tyr28,Trp30,Leu31]hPYY(3-36) (Compound 1);
N{alpha-4}-(3-Methylbutanoyl)-N{Epsilon-7}-[(4S)-4-carboxy-4-(17-carboxy-heptadecanoylamino)butanoyl]-[Arg4,Lys7,Gln18,Tyr28,Trp30,Leu31]hPYY(4-36) (Compound 2);
N{alpha-4}-(3-Methylbutanoyl)-N{Epsilon-7}-[2-[2-[2-[[2-[2-[2-[[(4S)-4-carboxy-4-(17-carboxyheptadecanoylamino)butanoyl]amino]ethoxy]ethoxy]acetyl]amino]-ethoxy]ethoxy]acetyl]-[Arg4,Lys7,Gln18,Tyr28,Trp30,Leu31]hPYY(4-36) (Compound 3);
N{alpha-4}-(3-Methylbutanoyl)-N{Epsilon-7}-6-[[(4S)-4-carboxy-4-(17-carboxy-heptadecanoylamino)butanoyl]amino]hexanoyl-[Arg4,Lys7,Pro9,Gln18,Tyr28,Trp30,Leu31]hPYY(4-36) (Compound 4);
N{alpha-4}-(3-Methylbutanoyl)-N{Epsilon-7}-[2-[2-[2-[[2-[2-[2-[[(4S)-4-carboxy-4-[[(4S)-4-carboxy-4-(17-carboxyheptadecanoylamino)butanoyl]amino]butanoyl]amino]-ethoxy]ethoxy]-acetyl]amino]ethoxy]ethoxy]acetyl]-[Arg4,Lys7,Gln18,Tyr28,Trp30,Leu31]hPYY(4-36) (Compound 5);
N{alpha-4}-(3-Methylbutanoyl)-N{Epsilon-7}-[(4S)-4-carboxy-4-(15-carboxy-pentadecanoylamino)butanoyl]-[Arg4,Lys7,Gln18,Tyr28,Trp30,Leu31]hPYY(4-36) (Compound 6);
N{alpha-4}-(3-Methylbutanoyl)-N{Epsilon-7}-[(4S)-4-carboxy-4-(19-carboxy-nonadecanoylamino)butanoyl]-[Arg4,Lys7,Gln18, Tyr28,Trp30,Leu31]hPYY(4-36) (Compound 7);
N{alpha-4}-(3-Methylbutanoyl)-N{Epsilon-7}-[2-[2-[2-[[(4S)-4-carboxy-4-(17-carboxy-heptadecanoylamino)butanoyl]amino]ethoxy]ethoxy]acetyl]-[Arg4,Lys7, Gln18,Tyr28, Trp30,Leu31]hPYY(4-36) (Compound 8);
N{alpha-4}-(3-Methylbutanoyl)-N{Epsilon-7}-[(4S)-4-carboxy-4-(16-sulfohexadecanoyl-amino)butanoyl]-[Arg4,Lys7,Gln18,Tyr28,Trp30,Leu31]hPYY(4-36) (Compound 9);
N{alpha-4}-(3-Methylbutanoyl)-N{Epsilon-7}-6-[[(4S)-4-carboxy-4-(19-carboxy-nonadecanoylamino)butanoyl]amino]hexanoyl-[Arg4,Lys7,Gln18,Tyr28, Trp30, Leu31]hPYY(4-36) (Compound 10);
N{alpha-4}-(3-Methylbutanoyl)-N{Epsilon-7}-[(4S)-4-carboxy-4-[[(4S)-4-carboxy-4-(17-carboxyheptadecanoylamino)butanoyl]amino]butanoyl]-[Arg4,Lys7, Pro9,Gln18, Tyr28,Trp30,Leu31]hPYY(4-36) (Compound 11);
N{alpha-4}-(3-Methylbutanoyl)-N{Epsilon-7}-[(4S)-4-carboxy-4-[[(4S)-4-carboxy-4-(19-carboxynonadecanoylamino)butanoyl]amino]butanoyl]-[Arg4,Lys7, Pro9,Gln18, Tyr28,Trp30,Leu31]hPYY(4-36) (Compound 12);
N{alpha-4}-(3-Methylbutanoyl)-N{Epsilon-7}-[2-[2-[2-[[2-[2-[2-[[(4S)-4-carboxy-4-(17-carboxyheptadecanoylamino)butanoyl]amino]ethoxy]ethoxy]acetyl]amino]-ethoxy]ethoxy]acetyl]-[Arg4,Lys7, Ser9, Gln18,Tyr28,Trp30,Leu31]hPYY(4-36) (Compound 13);
N{alpha-4}-(3-Methylbutanoyl)-N{Epsilon-7}-[2-[2-[2-[[2-[2-[2-[[(4S)-4-carboxy-4-(17-carboxyheptadecanoylamino)butanoyl]amino]ethoxy]ethoxy]acetyl]amino]-ethoxy]ethoxy]acetyl]-[Arg4,Lys7,Thr9, Gln18,Tyr28,Trp30,Leu31]hPYY(4-36) (Compound 14);
N{alpha-4}-(3-Methylbutanoyl)-N{Epsilon-7}-[(4S)-4-carboxy-4-(17-carboxy-heptadecanoylamino)butanoyl]-[Arg4,Lys7, Thr13,Gln18,Tyr28,Trp30,Leu31]hPYY(4-36) (Compound 15);
N{alpha-4}-(3-Methylbutanoyl)-N{Epsilon-7}-[2-[2-[2-[[2-[2-[2-[[(4S)-4-carboxy-4-(17-carboxyheptadecanoylamino)butanoyl]amino]ethoxy]ethoxy]acetyl]amino]-ethoxy]ethoxy]acetyl]-[Arg4,Lys7,Thr13, Gln18,Tyr28,Trp30,Leu31]hPYY(4-36) (Compound 16);
N{alpha-4}-(3-Methylbutanoyl)-N{Epsilon-7}-[(4S)-4-carboxy-4-(17-carboxy-heptadecanoylamino)butanoyl]-[Arg4,Lys7,Gln18,Ala24,Tyr28,Trp30,Leu31]hPYY(4-36) (Compound 17);
N{alpha-4}-(3-Methylbutanoyl)-N{Epsilon-7}-[(4S)-4-carboxy-4-(17-carboxy-heptadecanoylamino)butanoyl]-[Arg4,Lys7,Gln18,Ile24,Tyr28,Trp30,Leu31]hPYY(4-36) (Compound 18);
N{alpha-4}-(3-Methylbutanoyl)-N{Epsilon-7}-6-[[(4S)-4-carboxy-4-(19-carboxy-nonadecanoylamino)butanoyl]amino]hexanoyl-[Arg4,Lys7,Gln18,Ile24, Tyr28,Trp30, Leu31]hPYY(4-36) (Compound 19);
N{alpha-4}-(3-Methylbutanoyl)-N{Epsilon-7}-6-[[(4S)-4-carboxy-4-(17-carboxy-heptadecanoylamino)butanoyl]amino]hexanoyl-[Arg4,Lys7, Gln 18,Ile24, Tyr28,Trp30,Leu31]hPYY(4-36) (Compound 20);
N{alpha-4}-}-(3-Methylbutanoyl)-N{Epsilon-7}-[2-[2-[2-[[2-[2-[2-[[(4S)-4-carboxy-4-(17-carboxy-heptadecanoylamino)butanoyl]amino]ethoxy]ethoxy]acetyl]amino]ethoxy]ethoxy]acetyl]-[Arg4,Lys7,Pro9,Gln18, Tyr28,Trp30,Leu31]hPYY(4-36) (Compound 21);
N{Alpha-4}-acetyl,N{Epsilon-7}-[(4S)-4-carboxy-4-(17-carboxyheptadecanoylamino)-butanoyl]-[Arg4, Lys7,Gln18,Ile24,Tyr28,Trp30,Leu31]hPYY(4-36) (Compound 22);
N{Epsilon-7}-[(4S)-4-carboxy-4-[[(4S)-4-carboxy-4-(17-carboxyheptadecanoylamino)-butanoyl]amino]butanoyl]-[Arg4,Lys7,Gln18,Ile22,Trp30,Leu31]hPYY(3-36) (Compound 23);
N{Epsilon-7}-[2-[2-[2-[[2-[2-[2-[[(4S)-4-carboxy-4-(17-carboxyheptadecanoylamino)-butanoyl]amino]ethoxy]ethoxy]acetyl]amino]ethoxy]ethoxy]acetyl]-[Arg4, Lys7, Gin 8, Ile22,Trp30,Leu31]hPYY(3-36) (Compound 24);

N{alpha-4}-(3-Methylbutanoyl)-N{Epsilon-7}-[(4S)-4-carboxy-4-(17-carboxy-heptadecanoylamino)butanoyl]-[Arg4,Lys7,Gln18,Ile22,Trp30,Leu31]hPYY (4-36) (Compound 25);

N{alpha-4}-(3-Methylbutanoyl)-N{Epsilon-7}-[2-[2-[2-[[2-[2-[2-[[(4S)-4-carboxy-4-(17-carboxyheptadecanoylamino)butanoyl]amino]ethoxy]ethoxy]acetyl]amino]-ethoxy]ethoxy]acetyl]-[Arg4,Lys7,Gln18,Ile22,Trp30,Leu31]hPYY(4-36) (Compound 26);

N{alpha-4}-(3-Methylbutanoyl)-N{Epsilon-7}-[(4S)-4-carboxy-4-(17-carboxy-heptadecanoylamino)butanoyl]-[Arg4,Lys7,Pro9,Gln18,Ile22,Trp30,Leu31]hPYY(4-36) (Compound 27);

N{alpha-4}-(3-Methylbutanoyl)-N{Epsilon-7}-[2-[2-[2-[[2-[2-[2-[[(4S)-4-carboxy-4-[[(4S)-4-carboxy-4-(17-carboxyheptadecanoylamino)butanoyl]amino]butanoyl]amino]-ethoxy]ethoxy]acetyl]amino]ethoxy]ethoxy]acetyl]-[Arg4,Lys7,Gln18,Ile22,Trp30, Leu31]hPYY(4-36) (Compound 28);

N{alpha-4}-(3-Methylbutanoyl)-N{Epsilon-7}-[(4S)-4-carboxy-4-[[(4S)-4-carboxy-4-(17-carboxyheptadecanoylamino)butanoyl]amino]butanoyl]-[Arg4,Lys7,Gln18,Ile22, Tyr28,Trp30,Leu31]hPYY(4-36) (Compound 29);

N{alpha-4}-(3-Methylbutanoyl)-N{Epsilon-7}-[2-[2-[2-[[2-[2-[2-[[(4S)-4-carboxy-4-[[(4S)-4-carboxy-4-(17-carboxyheptadecanoylamino)butanoyl]amino]butanoyl]amino]-ethoxy]ethoxy]acetyl]amino]ethoxy]ethoxy]acetyl]-[Arg4,Lys7,Gln18,Ile22,Tyr28, Trp30,Leu31]hPYY(4-36) (Compound 30);

N{alpha-4}-(3-Methylbutanoyl)-N{Epsilon-7}-[2-[2-[2-[[2-[2-[2-[[(4S)-4-carboxy-4-(17-carboxyheptadecanoylamino)butanoyl]amino]ethoxy]ethoxy]acetyl]-amino]ethoxy]ethoxy]acetyl]-[Arg4,Lys7,Gln18,Ile22,Tyr28,Trp30,Leu31]hPYY(4-36) (Compound 31);

N{alpha-4}-(3-Methylbutanoyl)-N{Epsilon-7}-6-[[(4S)-4-carboxy-4-(17-carboxy-heptadecanoylamino)butanoyl]amino]hexanoyl-[Arg4,Lys7,Gln18,Ile22,Tyr28, Trp30,Leu31]hPYY(4-36) (Compound 32);

N{alpha-4}-(3-Methylbutanoyl)-N{Epsilon-7}-[(4S)-4-carboxy-4-[[(4S)-4-carboxy-4-(19-carboxynonadecanoylamino)butanoyl]amino]butanoyl]-[Arg4,Lys7,Gln18, Ile22,Tyr28,Trp30,Leu31]hPYY(4-36) (Compound 33);

N{alpha-4}-(3-Methylbutanoyl)-N{Epsilon-7}-[(4S)-4-carboxy-4-(17-carboxy-heptadecanoylamino)butanoyl]-[Arg4,Lys7,Gln18,Ile22,Ala24,Tyr28,Trp30,Leu31]hPYY(4-36) (Compound 34);

N{alpha-4}-(3-Methylbutanoyl)-N{Epsilon-7}-[(4S)-4-carboxy-4-(17-carboxy-heptadecanoylamino)butanoyl]-[Arg4,Lys7, Gln18,Gln22,Tyr28,Trp30,Leu31]hPYY(4-36) (Compound 35);

N{alpha-4}-(3-Methylbutanoyl)-N{Epsilon-7}-[2-[2-[2-[[2-[2-[2-[[(4S)-4-carboxy-4-(17-carboxyheptadecanoylamino)butanoyl]amino]ethoxy]ethoxy]acetyl]-amino]ethoxy]ethoxy]acetyl]-[Arg4,Lys7,Gln18,Gln22,Tyr28,Trp30,Leu31]hPYY(4-36) (Compound 36);

N{alpha-4}-(3-Methylbutanoyl)-N{Epsilon-7}-[2-[2-[2-[[2-[2-[2-[[(4S)-4-carboxy-4-[[(4S)-4-carboxy-4-(17-carboxyheptadecanoylamino)butanoyl]amino]butanoyl]amino]-ethoxy]ethoxy]acetyl]amino]ethoxy]ethoxy]acetyl]-[Arg4,Lys7,Gln18,Gln22,Tyr28, Trp30,Leu31]hPYY(4-36) (Compound 37);

N{alpha-4}-(3-Methylbutanoyl)-N{Epsilon-7}-[2-[2-[2-[[2-[2-[2-[[(4S)-4-carboxy-4-(17-carboxyheptadecanoylamino)butanoyl]amino]ethoxy]ethoxy]acetyl]amino]-ethoxy]ethoxy]acetyl]-[Arg4,Lys7,Gln18,Val22,Tyr28,Trp30,Leu31]hPYY(4-36) (Compound 38);

N{alpha-4}-(3-Methylbutanoyl)-N{Epsilon-7}-[2-[2-[2-[[2-[2-[2-[[(4S)-4-carboxy-4-[[(4S)-4-carboxy-4-(17-carboxyheptadecanoylamino)butanoyl]amino]butanoyl]-amino]ethoxy]ethoxy]acetyl]amino]ethoxy]ethoxy]acetyl]-[Arg4,Lys7,Gln18,Val22, Tyr28,Trp30,Leu31]hPYY(4-36) (Compound 39);

N{alpha-4}-(3-Methylbutanoyl)-N{Epsilon-7}-[(4S)-4-carboxy-4-(17-carboxy-heptadecanoylamino)butanoyl]-[Arg4,Lys7,Gln18,Val22,Tyr28,Trp30,Leu31]hPYY(4-36) (Compound 40);

N{alpha-4}-}-(3-Methylbutanoyl)-(N{Epsilon-7}-[(4S)-4-carboxy-4-[[(4S)-4-carboxy-4-(17-carboxy-heptadecanoylamino)butanoyl]amino]butanoyl]-[Arg4,Lys7, Gln18,Val22, Tyr28,Trp30,Leu31]hPYY(4-36) (Compound 41);

N{alpha-4}-(3-Methylbutanoyl)-N{Epsilon-7}-[(4S)-4-carboxy-4-(17-carboxy-heptadecanoylamino)butanoyl]-[Arg4,Lys7,Thr9, Gln18,Tyr28,Trp30,Leu31]hPYY(4-36) (Compound 42);

N{alpha-4}-(3-Methylbutanoyl)-N{Epsilon-7}-[(4S)-4-carboxy-4-(17-carboxy-heptadecanoylamino)butanoyl]-[Arg4,Lys7,Thr9,Gln18,Gln22,Tyr28,Trp30, Leu31]hPYY(4-36) (Compound 43);

N{alpha-4}-(3-Methylbutanoyl)-N{Epsilon-7}-[(4S)-4-carboxy-4-(17-carboxy-heptadecanoylamino)butanoyl]-[Arg4,Lys7,Thr9,Gln18,Val22,Tyr28,Trp30, Leu31]hPYY(4-36) (Compound 44);

N{alpha-4}-(3-Methylbutanoyl)-N{Epsilon-7}-[(4S)-4-carboxy-4-(17-carboxy-heptadecanoylamino)butanoyl]-[Arg4,Lys7,Thr13,Gln18,Gln22,Tyr28, Trp30, Leu31]hPYY(4-36) (Compound 45);

N{alpha-4}-(3-Methylbutanoyl)-N{Epsilon-7}-[2-[2-[2-[[2-[2-[2-[[(4S)-4-carboxy-4-(17-carboxyheptadecanoylamino)butanoyl]amino]ethoxy]ethoxy]acetyl]-amino]-ethoxy]ethoxy]acetyl]-[Arg4,Lys7,Thr13, Gln18,Val22,Tyr28,Trp30,Leu31]hPYY(4-36) (Compound 46);

N{alpha-4}-(3-Methylbutanoyl)-N{Epsilon-7}-[(4S)-4-carboxy-4-(17-carboxy-heptadecanoylamino)butanoyl]-[Arg4,Lys7,Thr13,Gln18,Val22,Tyr28, Trp30, Leu31]hPYY(4-36) (Compound 47);

N{alpha-4}-(3-Methylbutanoyl)-N{Epsilon-7}-[(4S)-4-carboxy-4-(19-carboxy-nonadecanoylamino)butanoyl]-[Arg4,Lys7,Gln18, Tyr28,Trp30,Leu31]hPYY (4-36) (Compound 48);

N{alpha-4}-(3-Methylbutanoyl)-N{Epsilon-7}-[(4S)-4-carboxy-4-(17-carboxy-heptadecanoylamino)butanoyl]-[Arg4,Lys7,Gln18,Ile22,Tyr28,Trp30,Leu31]hPYY(4-36) (Compound 49);

N{alpha-4}-(3-Methylbutanoyl)-N{Epsilon-10}-[(4S)-4-carboxy-4-[[2-[2-[2-[[(4S)-4-carboxy-4-(17-carboxy-heptadecanoylamino)butanoyl]amino]ethoxy]ethoxy]-acetyl]amino]butanoyl]-[Arg4,Lys10, Gln18, Glu22, Tyr28,Trp30,Leu31]-PYY(4-36) (Compound 50);

N{alpha-4}-(3-Methylbutanoyl)-N{Epsilon-10}-[2-[2-[2-[[2-[2-[2-[[(4S)-4-carboxy-4-(17-carboxyheptadecanoylamino)butanoyl]amino]ethoxy]ethoxy]acetyl]-amino]ethoxy]ethoxy]acetyl]-[Arg4,Lys10,Gln18, Glu22,Tyr28,Trp30,Leu31]-PYY(4-36) (Compound 51);

N{alpha-4}-(3-Methylbutanoyl)-N{Epsilon-10}-[2-[2-[2-[[2-[2-[2-[[(4S)-4-carboxy-4-(17-carboxyheptadecanoylamino)butanoyl]amino]ethoxy]ethoxy]acetyl]

amino]-ethoxy]ethoxy]acetyl]-[Arg4,Lys10,Gln18, Glu23, Tyr28,Trp30,Leu31]-PYY(4-36) (Compound 52);

N{alpha-4}-(3-Methylbutanoyl)-N{Epsilon-10}-[(4S)-4-carboxy-4-[[2-[2-[2-[[(4S)-4-carboxy-4-(17-carboxyheptadecanoylamino)butanoyl]amino]ethoxy]ethoxy]-acetyl]amino]butanoyl]-[Arg4,Lys10,Gln18,Glu23, Tyr28,Trp30,Leu31]-PYY(4-36) (Compound 53);

N{alpha-4}-(3-Methylbutanoyl)-N{Epsilon-10}-[(4S)-4-carboxy-4-[[2-[2-[2-[[(4S)-4-carboxy-4-(17-carboxyheptadecanoylamino)butanoyl]amino]ethoxy]ethoxy]-acetyl]amino]butanoyl]-[Arg4,Pro9,Lys10,Gln18, Glu22,Tyr28,Trp30,Leu31]-PYY(4-36) (Compound 54);

N{alpha-4}-(3-Methylbutanoyl)-N{Epsilon-7}-[(4S)-4-carboxy-4-(16-sulfohexadecanoylamino)butanoyl]-[Arg4,Lys7,Gln18, Tyr28,Trp30,Leu31]-PYY(4-36) (Compound 55);

N{alpha-4}-(3-Methylbutanoyl)-N{Epsilon-10}-[(4S)-4-carboxy-4-[[2-[2-[2-[[(4S)-4-carboxy-4-(17-carboxyheptadecanoylamino)butanoyl]amino]ethoxy]ethoxy]-acetyl]amino]butanoyl]-[Arg4,Pro9,Lys10,Gln18, Tyr28,Trp30,Leu31]-PYY(4-36) (Compound 56);

N{alpha-4}-(3-Methylbutanoyl)-N{Epsilon-7}-[2-[2-[2-[[(4S)-4-carboxy-4-(17-carboxyheptadecanoylamino) butanoyl]amino]ethoxy]ethoxy]acetyl]-[Arg4,Lys7, Gln18,Val22,Tyr28,Trp30,Leu31]-PYY(4-36) (Compound 57);

N{alpha-4}-(3-Methylbutanoyl)-N{Epsilon-7}-[2-[2-[2-[[(4S)-4-carboxy-4-(15-carboxypentadecanoylamino) butanoyl]amino]ethoxy]ethoxy]acetyl]-[Arg4,Lys7, Gln18,Tyr28,Trp30,Leu31]-PYY(4-36) (Compound 58);

N{alpha-4}-(3-Methylbutanoyl)-N{Epsilon-10}-[(4S)-4-carboxy-4-[[2-[2-[2-[[(4S)-4-carboxy-4-(17-carboxyheptadecanoylamino)butanoyl]amino]ethoxy]ethoxy]-acetyl]amino]butanoyl]-[Arg4,Lys10,Gln18,Tyr28, Trp30,Leu31]-PYY-(4-36) (Compound 59);

N{alpha-4}-(3-Methylbutanoyl)-N{Epsilon-7}-[2-[2-[2-[[(4S)-4-carboxy-4-(17-carboxyheptadecanoylamino) butanoyl]amino]ethoxy]ethoxy]acetyl]-[Arg4,Lys7, Gln18,Ala24,Tyr28,Trp30,Leu31]-PYY(4-36) (Compound 60);

N{alpha-4}-(3-Methylbutanoyl)-N{Epsilon-7}-[2-[2-[2-[[2-[2-[2-[[(4S)-4-carboxy-4-(15-carboxypentadecanoylamino)butanoyl]amino]ethoxy]ethoxy]acetyl]-amino]ethoxy]ethoxy]acetyl]-[Arg4,Lys7,Pro9,Gln18, Tyr28,Trp30,Leu31]-PYY-(4-36) (Compound 61);

N{alpha-4}-(3-Methylbutanoyl)-N{Epsilon-7}-[2-[2-[2-[[(4S)-4-carboxy-4-(13-carboxytridecanoylamino)butanoyl]amino]ethoxy]ethoxy]acetyl]-[Arg4,Lys7, Gln18,Tyr28,Trp30,Leu31]-PYY(4-36) (Compound 62);

N{alpha-4}-(3-Methylbutanoyl)-N{Epsilon-7}-[2-[2-[2-[[2-[2-[2-[[(4S)-4-carboxy-4-(15-carboxypentadecanoylamino)butanoyl]amino]ethoxy]ethoxy]acetyl]-amino]ethoxy]ethoxy]acetyl]-[Arg4,Lys7,Gln18, Tyr28,Trp30,Leu31]-PYY(3-36) (Compound 63);

N{alpha-4}-(3-Methylbutanoyl)-N{Epsilon-7}-[2-[2-[2-[[2-[2-[2-[[2-[2-[2-[[(4S)-4-carboxy-4-(17-carboxyheptadecanoylamino)butanoyl]amino]-ethoxy]ethoxy]acetyl]amino]ethoxy]ethoxy]acetyl]amino]ethoxy]ethoxy]acetyl]amino]ethoxy]ethoxy]acetyl]-[Arg4,Lys7,Pro9,Gln18,Tyr28,Trp30,Leu31]-PYY(4-36) (Compound 65);

N{alpha-4}-(3-Methylbutanoyl)-N{Epsilon-7}-[2-[2-[2-[[2-[2-[2-[[(4S)-4-carboxy-4-(16-sulfohexadecanoylamino)butanoyl]amino]ethoxy]ethoxy]acetyl]-amino]ethxy]ethoxy]acetyl]-[Arg4,Lys7,Pro9,Gln18,Tyr28, Trp30,Leu31]-PYY(4-36) (Compound 66);

N{alpha-4}-(3-Methylbutanoyl)-N{Epsilon-7}-[2-[2-[2-[[(4S)-4-carboxy-4-(16-sulfohexadecanoylamino)butanoyl]amino]ethoxy]ethoxy]acetyl]-[Arg4,Lys7, Gln18,Tyr28,Trp30,Leu31]-PYY(4-36) (Compound 67);

N{alpha-4}-(3-Methylbutanoyl)-N{Epsilon-7}-[2-[2-[2-[[2-[2-[2-[[(4S)-4-carboxy-4-(16-sulfohexadecanoylamino)butanoyl]amino]ethoxy]ethoxy]acetyl]-amino]ethoxy]ethoxy]acetyl]-[Arg4,Lys7,Gln18,Tyr28, Trp30,Leu31]-PYY(4-36) (Compound 68);

N{alpha-4}-(3-Methylbutanoyl)-N{Epsilon-10}-[(4S)-4-carboxy-4-[[2-[2-[2-[[(4S)-4-carboxy-4-(16-sulfohexadecanoylamino)butanoyl]amino]ethoxy]-ethoxy]acetyl]amino]butanoyl]-[Arg4,Pro9,Lys10,Gln18, Tyr28,Trp30,Leu31]-PYY-(4-36) (Compound 69);

N{alpha-4}-(3-Methylbutanoyl)-N{Epsilon-7}-[(4S)-4-carboxy-4-(13-carboxytridecanoylamino)butanoyl]-[Arg4,Lys7,Pro9,Gln18,Tyr28,Trp30,Leu31]-PYY-(4-36) (Compound 70); and N{alpha-4}-(3-Methylbutanoyl)-N{Epsilon-7}-[2-[2-[2-[[(4S)-4-carboxy-4-(13-carboxytridecanoylamino)butanoyl]amino]ethoxy]ethoxy]acetyl]-[Arg4,Lys7,Pro9, Gln18,Tyr28,Trp30,Leu31]-PYY-(4-36) (Compound 71).

11. A pharmaceutical composition comprising a PYY compound according to claim 1, and at least one pharmaceutically acceptable excipient.

12. A method for the treatment and/or prevention of Type 1 diabetes, Type 2 diabetes, eating disorders, diabetic complications, cardiovascular diseases and/or sleep apnoea; and/or for improving lipid parameters, improving β-cell function, and/or for delaying or preventing diabetic disease progression comprising administering to a subject in need of such treatment a pharmaceutically effective amount of a PYY compound according to claim 1.

13. A method for the treatment and/or prevention of Type 1 diabetes, Type 2 diabetes, diabetic complications, cardiovascular diseases and/or sleep apnoea; and/or for improving lipid parameters, improving β-cell function, and/or for delaying or preventing diabetic disease progression comprising: administering to a subject in need of such treatment a pharmaceutically effective amount of a pharmaceutical composition comprising a PYY compound according to claim 11.

14. A method for the treatment and/or prevention of eating disorders, treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, osteoarthritis and/or urine incontinence comprising: administering to a subject in need of such treatment a pharmaceutically effective amount of a PYY compound according to claim 1.

15. A method for the treatment and/or prevention of eating disorders, treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, osteoarthritis and/or urine incontinence comprising: administering to a subject in need of such treatment a pharmaceutically effective amount of a pharmaceutical composition comprising a PYY compound according to claim 11.

16. A pharmaceutical composition comprising a PYY compound according to claim 10, and at least one pharmaceutically acceptable excipient.

17. A method for the treatment and/or prevention of Type 1 diabetes, Type 2 diabetes, diabetic complications, cardiovascular diseases and/or sleep apnoea; and/or for improving lipid parameters, improving β-cell function, and/or for delaying or preventing diabetic disease progression comprising: administering to a subject in need of such treatment a pharmaceutically effective amount of a pharmaceutical composition comprising a PYY compound according to claim 10.

18. A method for the treatment and/or prevention of eating disorders, treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, osteoarthritis and/or urine incontinence comprising: administering to a subject in need of such treatment a pharmaceutically effective amount of a pharmaceutical composition comprising a PYY compound according to claim 10.

19. A PYY compound according to claim 1 having a maximum of 10 amino acid modifications as compared to hPYY(3-36) (SEQ ID NO:2), wherein the PYY compound comprises
   i) lysine at the position corresponding to position 7 of hPYY(1-36) (SEQ ID NO:1);
   ii) tryptophan at the position corresponding to position 30 of hPYY(1-36) (SEQ ID NO:1);
   iii) leucine at the position corresponding to position 31 of hPYY(1-36) (SEQ ID NO:1);
   iv) tyrosine at the position corresponding to position 28 of hPYY(1-36) (SEQ ID NO:1); and
   v) a modifying group attached to the epsilon amino group of said lysine at the position corresponding to position 7 of hPYY(1-36) (SEQ ID NO:1),
   wherein said modifying group is defined by A-[B]<sub>r</sub>—C—,
   A— is Chem. 1

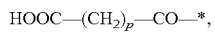

and wherein p is an integer in the range of 14-18;
   B— is Chem. 3

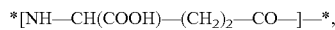

r is an integer in the range of 1-3; and
   C— is selected from Chem. 5

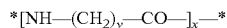

wherein v is an integer in the range of 4-6, and x is an integer in the range of 1-3;
   wherein * denotes the points of attachment, and wherein A, B, and C are interconnected via amide bonds and in the sequence indicated via said point of attachments; or a pharmaceutically acceptable salt, amide, or ester of said PYY compound.

20. A PYY compound N{alpha-4}-(3-Methylbutanoyl)-N{Epsilon-7}-6-[[(4S)-4-carboxy-4-(17-carboxy-heptadecanoylamino)butanoyl]amino]hexanoyl-[Arg4,Lys7,Pro9,Gln18,Tyr28,Trp30,Leu31]hPYY(4-36) (Compound 4).

21. A PYY compound N{alpha-4}-(3-Methylbutanoyl)-N{Epsilon-7}-6-[[(4S)-4-carboxy-4-(17-carboxy-heptadecanoylamino)butanoyl]amino]hexanoyl-[Arg4,Lys7,Gln18,Ile24,Tyr28,Trp30,Leu31]hPYY(4-36) (Compound 20).

22. A PYY compound N{alpha-4}-(3-Methylbutanoyl)-N{Epsilon-7}-6-[[(4S)-4-carboxy-4-(17-carboxy-heptadecanoylamino)butanoyl]amino]hexanoyl-[Arg4,Lys7,Gln 18,Ile 22,Tyr28,Trp30,Leu31]hPYY(4-36) (Compound 32).

23. A pharmaceutical composition comprising the PYY compound according to claim 19, and at least one pharmaceutically acceptable excipient.

24. A method for the treatment and/or prevention of Type 1 diabetes, Type 2 diabetes, diabetic complications, cardiovascular diseases and/or sleep apnoea; and/or for improving lipid parameters, improving β-cell function, and/or for delaying or preventing diabetic disease progression comprising: administering to a subject in need of such treatment a pharmaceutically effective amount of a pharmaceutical composition comprising the PYY compound according to claim 19.

25. A method for the treatment and/or prevention of eating disorders, treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, osteoarthritis and/or urine incontinence comprising: administering to a subject in need of such treatment a pharmaceutically effective amount of a pharmaceutical composition comprising the PYY compound according to claim 19.

26. A pharmaceutical composition comprising the PYY compound according to claim 20, and at least one pharmaceutically acceptable excipient.

27. A pharmaceutical composition comprising the PYY compound according to claim 21, and at least one pharmaceutically acceptable excipient.

28. A pharmaceutical composition comprising the PYY compound according to claim 22, and at least one pharmaceutically acceptable excipient.

29. A method for the treatment and/or prevention of Type 1 diabetes, Type 2 diabetes, diabetic complications, cardiovascular diseases and/or sleep apnoea; and/or for improving lipid parameters, improving β-cell function, and/or for delaying or preventing diabetic disease progression comprising: administering to a subject in need of such treatment a pharmaceutically effective amount of a pharmaceutical composition comprising the PYY compound according to claim 20.

30. A method for the treatment and/or prevention of Type 1 diabetes, Type 2 diabetes, diabetic complications, cardiovascular diseases and/or sleep apnoea; and/or for improving lipid parameters, improving β-cell function, and/or for delaying or preventing diabetic disease progression comprising: administering to a subject in need of such treatment a pharmaceutically effective amount of a pharmaceutical composition comprising the PYY compound according to claim 21.

31. A method for the treatment and/or prevention of Type 1 diabetes, Type 2 diabetes, diabetic complications, cardiovascular diseases and/or sleep apnoea; and/or for improving lipid parameters, improving β-cell function, and/or for delaying or preventing diabetic disease progression comprising: administering to a subject in need of such treatment a pharmaceutically effective amount of a pharmaceutical composition comprising the PYY compound according to claim 22.

32. A method for the treatment and/or prevention of eating disorders, treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, osteoarthritis and/or urine incontinence comprising: administering to a subject in need of such treatment a pharmaceutically effective amount of a pharmaceutical composition comprising the PYY compound according to claim 20.

33. A method for the treatment and/or prevention of eating disorders, treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, osteoarthritis and/or urine incontinence comprising: administering to a subject in need of such treatment a pharmaceutically effective amount of a pharmaceutical composition comprising the PYY compound according to claim 21.

34. A method for the treatment and/or prevention of eating disorders, treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, osteoarthritis and/or urine incontinence comprising: administering to a subject in need of such treatment a pharmaceutically effective amount of a pharmaceutical composition comprising the PYY compound according to claim 22.

* * * * *

UNITED STATES PATENT AND TRADEMARK OFFICE
CERTIFICATE OF CORRECTION

PATENT NO. : 10,005,824 B2  
APPLICATION NO. : 15/635456  
DATED : June 26, 2018  
INVENTOR(S) : Soeren Oestergaard et al.

Page 1 of 1

It is certified that error appears in the above-identified patent and that said Letters Patent is hereby corrected as shown below:

In the Claims

At Column 144, Claim number 10, Line number 66, please amend as follows:  
"…Lys7,Gln18,Ile22,Trp30,Leu31]hPYY(3-36)…"

Signed and Sealed this  
Sixteenth Day of October, 2018

Andrei Iancu  
*Director of the United States Patent and Trademark Office*

SEQUENCE LISTING

```
<160> NUMBER OF SEQ ID NOS: 29

<210> SEQ ID NO 1
<211> LENGTH: 36
<212> TYPE: PRT
<213> ORGANISM: HOMO SAPIENS

<400> SEQUENCE: 1

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 2
<211> LENGTH: 34
<212> TYPE: PRT
<213> ORGANISM: HOMO SAPIENS

<400> SEQUENCE: 2

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 3
<211> LENGTH: 34
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (34)..(34)
<223> OTHER INFORMATION: AMIDATION
```

```
<400> SEQUENCE: 3

Ile Arg Pro Glu Lys Pro Gly Glu Asp Ala Ser Pro Glu Glu Leu Gln
1               5                   10                  15

Arg Tyr Tyr Ala Ser Leu Arg His Tyr Tyr Asn Trp Leu Thr Arg Gln
                20                  25                  30

Arg Tyr

<210> SEQ ID NO 4
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (33)..(33)
<223> OTHER INFORMATION: AMIDATION

<400> SEQUENCE: 4

Arg Pro Glu Lys Pro Gly Glu Asp Ala Ser Pro Glu Glu Leu Gln Arg
1               5                   10                  15

Tyr Tyr Ala Ser Leu Arg His Tyr Tyr Asn Trp Leu Thr Arg Gln Arg
                20                  25                  30

Tyr

<210> SEQ ID NO 5
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (33)..(33)
<223> OTHER INFORMATION: AMIDATION

<400> SEQUENCE: 5

Arg Pro Glu Lys Pro Pro Glu Asp Ala Ser Pro Glu Glu Leu Gln Arg
1               5                   10                  15

Tyr Tyr Ala Ser Leu Arg His Tyr Tyr Asn Trp Leu Thr Arg Gln Arg
                20                  25                  30

Tyr

<210> SEQ ID NO 6
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (33)..(33)
<223> OTHER INFORMATION: AMIDATION

<400> SEQUENCE: 6

Arg Pro Glu Lys Pro Ser Glu Asp Ala Ser Pro Glu Glu Leu Gln Arg
1               5                   10                  15

Tyr Tyr Ala Ser Leu Arg His Tyr Tyr Asn Trp Leu Thr Arg Gln Arg
                20                  25                  30

Tyr

<210> SEQ ID NO 7
<211> LENGTH: 33
```

-continued

```
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (33)..(33)
<223> OTHER INFORMATION: AMIDATION

<400> SEQUENCE: 7

Arg Pro Glu Lys Pro Thr Glu Asp Ala Ser Pro Glu Glu Leu Gln Arg
1               5                   10                  15

Tyr Tyr Ala Ser Leu Arg His Tyr Tyr Asn Trp Leu Thr Arg Gln Arg
            20                  25                  30

Tyr

<210> SEQ ID NO 8
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (33)..(33)
<223> OTHER INFORMATION: AMIDATION

<400> SEQUENCE: 8

Arg Pro Glu Lys Pro Gly Glu Asp Ala Thr Pro Glu Glu Leu Gln Arg
1               5                   10                  15

Tyr Tyr Ala Ser Leu Arg His Tyr Tyr Asn Trp Leu Thr Arg Gln Arg
            20                  25                  30

Tyr

<210> SEQ ID NO 9
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (33)..(33)
<223> OTHER INFORMATION: AMIDATION

<400> SEQUENCE: 9

Arg Pro Glu Lys Pro Gly Glu Asp Ala Ser Pro Glu Glu Leu Gln Arg
1               5                   10                  15

Tyr Tyr Ala Ser Ala Arg His Tyr Tyr Asn Trp Leu Thr Arg Gln Arg
            20                  25                  30

Tyr

<210> SEQ ID NO 10
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (33)..(33)
<223> OTHER INFORMATION: AMIDATION

<400> SEQUENCE: 10

Arg Pro Glu Lys Pro Gly Glu Asp Ala Ser Pro Glu Glu Leu Gln Arg
1               5                   10                  15
```

```
Tyr Tyr Ala Ser Ile Arg His Tyr Tyr Asn Trp Leu Thr Arg Gln Arg
            20                  25                  30

Tyr

<210> SEQ ID NO 11
<211> LENGTH: 34
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (34)..(34)
<223> OTHER INFORMATION: AMIDATION

<400> SEQUENCE: 11

Glx Arg Pro Glu Lys Pro Gly Glu Asp Ala Ser Pro Glu Glu Leu Gln
1               5                   10                  15

Arg Tyr Tyr Ala Ser Ile Arg His Tyr Tyr Asn Trp Leu Thr Arg Gln
            20                  25                  30

Arg Tyr

<210> SEQ ID NO 12
<211> LENGTH: 34
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (34)..(34)
<223> OTHER INFORMATION: AMIDATION

<400> SEQUENCE: 12

Ile Arg Pro Glu Lys Pro Gly Glu Asp Ala Ser Pro Glu Glu Leu Gln
1               5                   10                  15

Arg Tyr Tyr Ile Ser Leu Arg His Tyr Leu Asn Trp Leu Thr Arg Gln
            20                  25                  30

Arg Tyr

<210> SEQ ID NO 13
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (33)..(33)
<223> OTHER INFORMATION: AMIDATION

<400> SEQUENCE: 13

Arg Pro Glu Lys Pro Gly Glu Asp Ala Ser Pro Glu Glu Leu Gln Arg
1               5                   10                  15

Tyr Tyr Ile Ser Leu Arg His Tyr Leu Asn Trp Leu Thr Arg Gln Arg
            20                  25                  30

Tyr

<210> SEQ ID NO 14
<211> LENGTH: 33
<212> TYPE: PRT
<213> ORGANISM: ARTIFICIAL
<220> FEATURE:
<223> OTHER INFORMATION: Artificial protein based on human PYY
```

```
<220> FEATURE:
<221> NAME/KEY: MISC_FEATURE
<222> LOCATION: (33)..(33)
<223> OTHER INFORMATION: AMIDATION

<400> SEQUENCE: 14

Arg Pro Glu Lys Pro Glu Asp Ala Ser Pro Glu Glu Leu Gln Arg
1               5                   10                  15

Tyr Tyr Ile Ser Leu Arg His Tyr Leu Asn Trp Leu Thr Arg Gln Arg
            20                  25                  30

Tyr

<210> SEQ ID NO 15
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (33)..(33)
<223> OTHER INFORMATION: AMIDATION

<400> SEQUENCE: 15

Arg Pro Glu Lys Pro Gly Glu Asp Ala Ser Pro Glu Glu Leu Gln Arg
1               5                   10                  15

Tyr Tyr Ile Ser Leu Arg His Tyr Tyr Asn Trp Leu Thr Arg Gln Arg
            20                  25                  30

Tyr

<210> SEQ ID NO 16
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (33)..(33)
<223> OTHER INFORMATION: AMIDATION

<400> SEQUENCE: 16

Arg Pro Glu Lys Pro Gly Glu Asp Ala Ser Pro Glu Glu Leu Gln Arg
1               5                   10                  15

Tyr Tyr Ile Ser Ala Arg His Tyr Tyr Asn Trp Leu Thr Arg Gln Arg
            20                  25                  30

Tyr

<210> SEQ ID NO 17
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (33)..(33)
<223> OTHER INFORMATION: AMIDATION

<400> SEQUENCE: 17

Arg Pro Glu Lys Pro Gly Glu Asp Ala Ser Pro Glu Glu Leu Gln Arg
1               5                   10                  15

Tyr Tyr Gln Ser Leu Arg His Tyr Tyr Asn Trp Leu Thr Arg Gln Arg
            20                  25                  30
```

Tyr

```
<210> SEQ ID NO 18
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (33)..(33)
<223> OTHER INFORMATION: AMIDATION

<400> SEQUENCE: 18
```

Arg Pro Glu Lys Pro Gly Glu Asp Ala Ser Pro Glu Glu Leu Gln Arg
1               5                   10                  15

Tyr Tyr Val Ser Leu Arg His Tyr Tyr Asn Trp Leu Thr Arg Gln Arg
            20                  25                  30

Tyr

```
<210> SEQ ID NO 19
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (33)..(33)
<223> OTHER INFORMATION: AMIDATION

<400> SEQUENCE: 19
```

Arg Pro Glu Lys Pro Thr Glu Asp Ala Ser Pro Glu Glu Leu Gln Arg
1               5                   10                  15

Tyr Tyr Gln Ser Leu Arg His Tyr Tyr Asn Trp Leu Thr Arg Gln Arg
            20                  25                  30

Tyr

```
<210> SEQ ID NO 20
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (33)..(33)
<223> OTHER INFORMATION: AMIDATION

<400> SEQUENCE: 20
```

Arg Pro Glu Lys Pro Thr Glu Asp Ala Ser Pro Glu Glu Leu Gln Arg
1               5                   10                  15

Tyr Tyr Val Ser Leu Arg His Tyr Tyr Asn Trp Leu Thr Arg Gln Arg
            20                  25                  30

Tyr

```
<210> SEQ ID NO 21
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (33)..(33)
<223> OTHER INFORMATION: AMIDATION
```

<400> SEQUENCE: 21

Arg Pro Glu Lys Pro Gly Glu Asp Ala Thr Pro Glu Glu Leu Gln Arg
1               5                   10                  15

Tyr Tyr Gln Ser Leu Arg His Tyr Tyr Asn Trp Leu Thr Arg Gln Arg
            20                  25                  30

Tyr

<210> SEQ ID NO 22
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (33)..(33)
<223> OTHER INFORMATION: AMIDATION

<400> SEQUENCE: 22

Arg Pro Glu Lys Pro Gly Glu Asp Ala Thr Pro Glu Glu Leu Gln Arg
1               5                   10                  15

Tyr Tyr Val Ser Leu Arg His Tyr Tyr Asn Trp Leu Thr Arg Gln Arg
            20                  25                  30

Tyr

<210> SEQ ID NO 23
<211> LENGTH: 33
<212> TYPE: PRT
<213> ORGANISM: Artificial Sequence
<220> FEATURE:
<223> OTHER INFORMATION: Artificial protein based on human PYY
<220> FEATURE:
<221> NAME/KEY: MISC_FEATURE
<222> LOCATION: (33)..(33)
<223> OTHER INFORMATION: Amidation

<400> SEQUENCE: 23

Arg Pro Glu Ala Pro Gly Lys Asp Ala Ser Pro Glu Glu Leu Gln Arg
1               5                   10                  15

Tyr Tyr Glu Ser Leu Arg His Tyr Tyr Asn Trp Leu Thr Arg Gln Arg
            20                  25                  30

Tyr

<210> SEQ ID NO 24
<211> LENGTH: 33
<212> TYPE: PRT
<213> ORGANISM: Artificial Sequence
<220> FEATURE:
<223> OTHER INFORMATION: Artificial protein based on human PYY
<220> FEATURE:
<221> NAME/KEY: MISC_FEATURE
<222> LOCATION: (33)..(33)
<223> OTHER INFORMATION: Amidation

<400> SEQUENCE: 24

Arg Pro Glu Ala Pro Gly Lys Asp Ala Ser Pro Glu Glu Leu Gln Arg
1               5                   10                  15

Tyr Tyr Ala Glu Leu Arg His Tyr Tyr Asn Trp Leu Thr Arg Gln Arg
            20                  25                  30

Tyr

<210> SEQ ID NO 25

```
<211> LENGTH: 33
<212> TYPE: PRT
<213> ORGANISM: Artificial Sequence
<220> FEATURE:
<223> OTHER INFORMATION: Artificial protein based on human PYY
<220> FEATURE:
<221> NAME/KEY: MISC_FEATURE
<222> LOCATION: (33)..(33)
<220> FEATURE:
<221> NAME/KEY: MOD_RES
<222> LOCATION: (33)..(33)
<223> OTHER INFORMATION: AMIDATION

<400> SEQUENCE: 25

Arg Pro Glu Ala Pro Pro Lys Asp Ala Ser Pro Glu Glu Leu Gln Arg
1               5                   10                  15

Tyr Tyr Glu Ser Leu Arg His Tyr Tyr Asn Trp Leu Thr Arg Gln Arg
            20                  25                  30

Tyr

<210> SEQ ID NO 26
<211> LENGTH: 33
<212> TYPE: PRT
<213> ORGANISM: Artificial Sequence
<220> FEATURE:
<223> OTHER INFORMATION: Artificial protein based on human PYY
<220> FEATURE:
<221> NAME/KEY: MOD_RES
<222> LOCATION: (33)..(33)
<223> OTHER INFORMATION: AMIDATION

<400> SEQUENCE: 26

Arg Pro Glu Ala Pro Pro Lys Asp Ala Ser Pro Glu Glu Leu Gln Arg
1               5                   10                  15

Tyr Tyr Ala Ser Leu Arg His Tyr Tyr Asn Trp Leu Thr Arg Gln Arg
            20                  25                  30

Tyr

<210> SEQ ID NO 27
<211> LENGTH: 33
<212> TYPE: PRT
<213> ORGANISM: Artificial Sequence
<220> FEATURE:
<223> OTHER INFORMATION: Artificial protein based on human PYY
<220> FEATURE:
<221> NAME/KEY: MOD_RES
<222> LOCATION: (33)..(33)
<223> OTHER INFORMATION: AMIDATION

<400> SEQUENCE: 27

Arg Pro Glu Ala Pro Gly Lys Asp Ala Ser Pro Glu Glu Leu Gln Arg
1               5                   10                  15

Tyr Tyr Ala Ser Leu Arg His Tyr Tyr Asn Trp Leu Thr Arg Gln Arg
            20                  25                  30

Tyr

<210> SEQ ID NO 28
<211> LENGTH: 33
<212> TYPE: PRT
<213> ORGANISM: Artificial Sequence
<220> FEATURE:
<223> OTHER INFORMATION: Artificial protein based on human PYY
<220> FEATURE:
<221> NAME/KEY: MOD_RES
<222> LOCATION: (33)..(33)
<223> OTHER INFORMATION: AMIDATION
```

-continued

```
<400> SEQUENCE: 28

Arg Pro Glu Ala Pro Gly Glu Asp Ala Ser Pro Glu Glu Leu Gln Arg
1               5                   10                  15

Tyr Tyr Ala Ser Leu Arg His Tyr Tyr Asn Trp Leu Thr Arg Gln Arg
            20                  25                  30

Tyr

<210> SEQ ID NO 29
<211> LENGTH: 33
<212> TYPE: PRT
<213> ORGANISM: Artificial Sequence
<220> FEATURE:
<223> OTHER INFORMATION: Artificial protein based on human PYY
<220> FEATURE:
<221> NAME/KEY: MISC_FEATURE
<222> LOCATION: (33)..(33)
<223> OTHER INFORMATION: AMIDATION

<400> SEQUENCE: 29

Arg Pro Glu Ala Pro Gly Glu Asp Ala Ser Pro Glu Glu Leu Gln Arg
1               5                   10                  15

Tyr Tyr Val Ser Leu Arg His Tyr Tyr Asn Trp Leu Thr Arg Gln Arg
            20                  25                  30

Tyr
```